(12) United States Patent
Mizhiritskii et al.

(10) Patent No.: US 8,772,503 B2
(45) Date of Patent: Jul. 8, 2014

(54) PROCESSES FOR THE PREPARATION OF DEFERASIROX, AND DEFERASIROX POLYMORPHS

(75) Inventors: Michael Mizhiritskii, Rehovot (IL); Ehud Marom, Kfar Saba (IL); Shai Rubnov, Tel Aviv (IL)

(73) Assignee: Mapi Pharma Ltd., Ness Ziona (IL)

( * ) Notice: Subject to any disclaimer, the term of this patent is extended or adjusted under 35 U.S.C. 154(b) by 0 days.

(21) Appl. No.: 13/514,155

(22) PCT Filed: Jan. 28, 2010

(86) PCT No.: PCT/IL2010/000074
§ 371 (c)(1),
(2), (4) Date: Jun. 6, 2012

(87) PCT Pub. No.: WO2011/070560
PCT Pub. Date: Jun. 16, 2011

(65) Prior Publication Data
US 2012/0245361 A1 Sep. 27, 2012

Related U.S. Application Data

(60) Provisional application No. 61/267,096, filed on Dec. 7, 2009.

(51) Int. Cl.
*C07D 249/08* (2006.01)
(52) U.S. Cl.
CPC .................................. *C07D 249/08* (2013.01)
USPC ....................................................... 548/265.8
(58) Field of Classification Search
None
See application file for complete search history.

(56) References Cited

U.S. PATENT DOCUMENTS

| | | | |
|---|---|---|---|
| 5,175,315 A | 12/1992 | Holton | |
| 5,318,959 A | 6/1994 | Ozaki et al. | |
| 6,465,504 B1 * | 10/2002 | Lattmann et al. | 514/383 |
| 2001/0037020 A1 | 11/2001 | Holton | |
| 2005/0080120 A1 | 4/2005 | Lattmann et al. | |

FOREIGN PATENT DOCUMENTS

| | | |
|---|---|---|
| EP | 0572142 A2 | 12/1993 |
| GB | 1330265 | 9/1973 |
| WO | 97/49395 A1 | 12/1997 |
| WO | 2008065123 A2 | 6/2008 |
| WO | 2008/094617 A2 | 8/2008 |
| WO | 2009/016359 A1 | 2/2009 |

OTHER PUBLICATIONS

Topuzyan, et al., "Derivatives of α,β-Dehydro Amino Acids: III. Reaction of 4-Arylmethylidene-4,5-dihydro-1,3-oxazol-5-ones with Hexamethyldisilazane", Russian Journal of Organic Chemistry, 2007, vol. 43, No. 6, pp. 868-871.
Vongchan, et al., "Anticoagulant Activities of the Chitosan Polysulfate Synthesized from Marine Crab Shell by Semi-heterogeneous Conditions", ScienceAsia, 2003, vol. 29, pp. 115-120.
Bowser et al., (1983) Cleavage of silicon-nitrogen bonds by acid chlorides: an unusual synthetic route to amides. The Journal of Organic Chemistry 48(22): 4111-4113.
Al-Masoudi, I. A. et al., (2006) 1,2,4-Triazoles: Synthetic approaches and pharmacological importance. Chemistry of Heterocyclic Compounds 42(11):1377-1403.
Du, Da-Ming et al., (2003) Reinvestigation on the Reaction of Salicylic Chloride with Salicylic Amide and X-ray Crystal Structure of a New Macrocyclic Polyester. Chinese J Struct Chem. 22(5):512-516.
McIntyre, J. A. et al., (2004) Deferasirox: treatment of iron overload, iron chelator. Drugs of the Future 29 (4):331-335.
Potts, K. T. (1961) The Chemistry of 1,2,4-Triazoles. Chem Rev 61(2):87-127.
Rigo, B. et al., (1986) Bis (trimethylsilyl) amide as nitrile precursor. Tetrahedron Letters 27(3):347-348.
Sato, N. et al., (2003) An efficient synthesis of cyanoarenes and cyanoheteroarenes via lithiation followed by electrophilic cyanation. Tetrahedron 59:5831-5836.
Steinhauser, S. et al., (2004) Complex formation of ICL670 and related ligands with Fe3 and Fe2. Eur J Inorg Chem.:4177-4192.
International Search Report of PCT/IL10/00074 and Written Opinion mailed Jun. 9, 2010, 13 pages.

* cited by examiner

*Primary Examiner* — Michael Barker
(74) *Attorney, Agent, or Firm* — Rothwell, Figg, Ernst & Manbeck, P.C.

(57) ABSTRACT

The present invention relates to processes for the preparation of deferasirox, an oral iron chelator developed to treat iron overload due to e.g. multiple blood transfusions. The present invention further provides novel deferasirox pseudopolymorphs and a novel amorphous form of deferasirox, processes for their preparation, as well as pharmaceutical compositions comprising same, and use thereof in treating iron overload.

10 Claims, 37 Drawing Sheets

PROCESSES FOR THE PREPARATION OF DEFERASIROX, AND DEFERASIROX POLYMORPHS

CROSS REFERENCE TO RELATED APPLICATION(S)

This application is a 35 U.S.C. §371 National Phase Entry Application from PCT/IL2010/000074 filed Jan. 28, 2010, designating the United States and claiming priority to U.S. Application 61/267,096 filed Dec. 7, 2009, the disclosures of which are incorporated by reference herein in their entirety.

FIELD OF THE INVENTION

The present invention relates to processes for the preparation of deferasirox, an oral iron chelator developed to treat chronic iron overload due to, e.g., multiple blood transfusions. The present invention further provides novel deferasirox pseudopolymorphs and a novel amorphous form of deferasirox, processes for their preparation, as well as pharmaceutical compositions comprising same, and use thereof in treating iron overload.

BACKGROUND OF THE INVENTION

Patients with chronic anemias such as thalassemia or sickle cell anemia often require regular red blood cell transfusions. Repeated transfusions result in toxic, and eventually fatal, accumulation of iron as insoluble ferritin in various tissues of the body. This chronic iron overload occurs due to the body's inability to actively eliminate iron. Chronic iron overload is a serious condition and organ failure can occur due to the resulting iron deposits. When the heart or liver are affected, the condition may be life threatening. Iron overload is treated by administration of iron chelators, which mobilize the iron deposits into soluble complexes that can be excreted from the body. The currently available first-line iron chelator, deferoxamine (Desferal®), requires intravenous or slow subcutaneous infusion over a period of 8-12 h, 5-7 times per week. This has resulted in low patient compliance of the product. Deferoxamine can also cause local and systemic reactions. An orally available iron chelator, deferiprone, also has a short duration of action and may be associated with serious side effects. Novartis therefore embarked on a major research program to identify oral iron chelators, which ultimately led to a completely new class of compounds, the bishydroxyphenyltriazoles. The best compound from this class was found to be deferasirox (ICL-670A), an orally active tridentate compound which is FDA approved and is marketed under the trade name Exjade® for the treatment of transfusion-dependent chronic iron overload (transfusional hemosiderosis) [Drugs of the Future 2004, 29(4): 331-335].

Deferasirox has the chemical name 4-[3,5-Bis(2-hydroxyphenyl)-1H-1,2,4-triazol-1-yl]benzoic acid, and is represented by the following structural Formula (1):

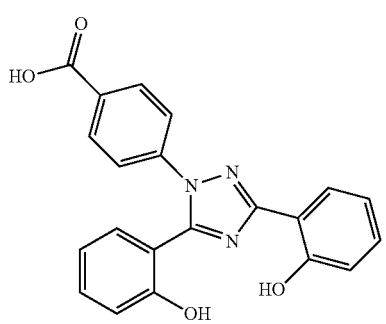

(1)

U.S. Pat. No. 6,465,504 discloses substituted 3,5-diphenyl-1,2,4-triazoles and their use as pharmaceutical metal chelators. This patent describes a process for the preparation of 4-[3,5-Bis(2-hydroxyphenyl)-1H-1,2,4-triazol-1-yl]benzoic acid (deferasirox) (1) that involves the condensation of salicylamide (2) with salicyloyl chloride (3) by heating at 170° C. yielding 2-(2-hydroxyphenyl)-benz[e][1,3]oxazin-4-one (5), which reacts with 4-hydrazinobenzoic acid (6) in refluxing ethanol to give (1) (Scheme 1):

Scheme 1

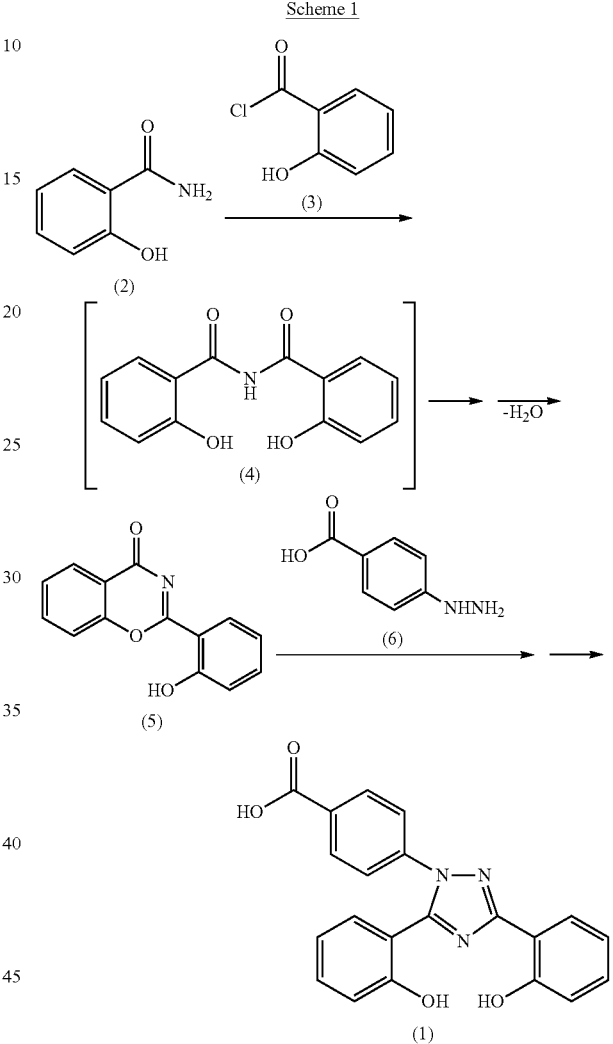

High reaction temperature (170° C.), evolution of corrosive and hazardous HCl gas and low overall yield (<50%) makes this process expensive and not feasible on an industrial scale.

U.S. Appln. Publication No. 2005/080120 provides another method for the preparation of deferasirox analogues. This process is also described in Eur. J. Inorg. Chem. 2004, 4177-4192, and consists of two stages. The first stage, formation of 2-(2-hydroxyphenyl)-benzo-4H-[1,3]-oxazin-4-one, involves a reaction of salicylic acid and salicylamide with thionyl chloride in the presence of pyridine under reflux in xylene or toluene with vigorous stirring over a period of 4 h. An intense evolution of $SO_2$ and HCl was noted. At the end of the addition, the product started to crystallize. Stirring was continued for an additional 30 min, and the solvent was removed by distillation at reduced pressure. The resulting solid residue was suspended in EtOH and acetic acid. The mixture was heated gently and then allowed to cool to 20° C. The precipitate was filtered and recrystallized from 2-methoxyethanol, providing the desired compound with 50-55% yield. The second stage proceeded according to previously mentioned patent (U.S. Pat. No. 6,465,504) and consists of reaction of 2-(2-hydroxy phenyl)-benzo-4H-[1,3]-oxazin-4-one with 4-hydrazinobenzoic acid in boiling ethanol. The reported yield of this stage was 80%.

Although this process is more technological than the one based on molding salicylamide in salicyloyl chloride, the overall yield is still moderate (40-45%). The moderate yield can be attributed to the formation of by-products—a mixture of the linear and cyclic polyesters (for example, (7)) as a result of intermolecular reaction of salicyloyl chloride [Chinese J. Struct. Chem., 2003, 22(5): 512-516] (Scheme 2):

Scheme 3

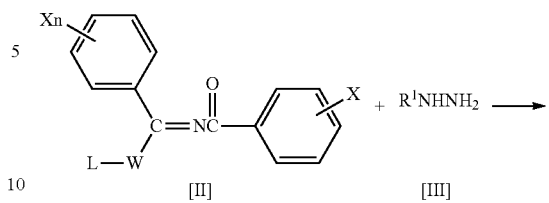

Scheme 2

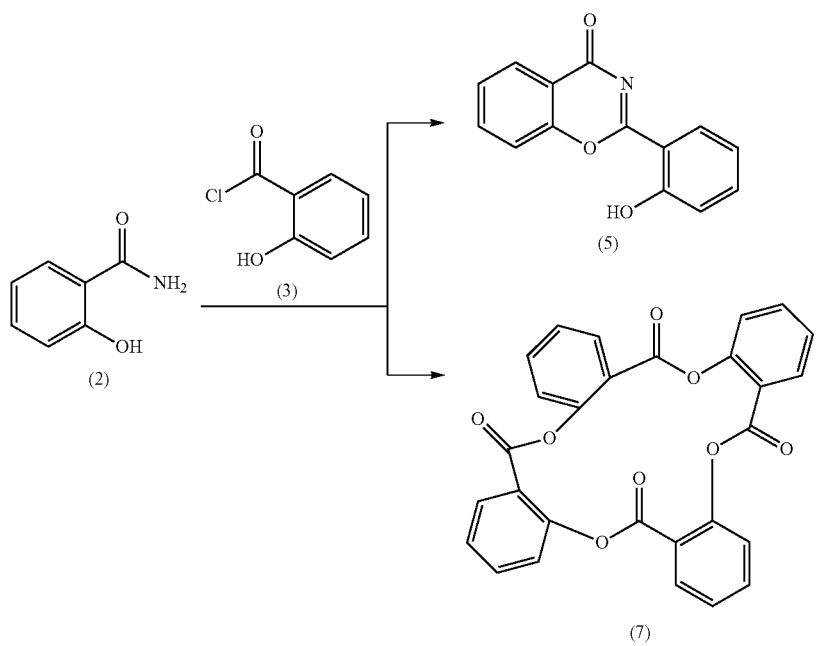

Therefore, there is a need for a process, in which no significant heating is required and the formation of polyesters as well as corrosive and hazardous gases such as HCl is minimized or avoided.

Deferasirox belongs to the family of substituted 1,2,4-triazoles, heterocycles possessing important pharmacological activities such as antifungal and antiviral activities. Methods for the synthesis of 1,2,4-triazoles are well described in literature [See, for example, review "1,2,4-TRIAZOLES: SYNTHETIC APPROACHES AND PHARMACOLOGICAL IMPORTANCE" in Chemistry of Heterocyclic Compounds, 2006, 42(11): 1377-1403], but most of these methods are not suitable for the construction of 1,3,5-substituted 1,2,4-triazoles.

A preparation of substituted 3,5-diphenyl-1,2,4-triazoles [I] structurally close to deferasirox can be found in European Patent No. 0572142, and can be achieved by a reaction between an alkyl N-acyl(thio)imidate derivative, having a general formula [II], and a hydrazine derivative of a general formula [III] in an inert solvent, according to the following scheme:

-continued

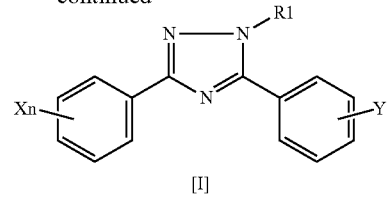

The starting compound of the general formula [II] was prepared by reacting the imine [IV] with the halogen anhydride [V] in the presence of a base according to the following scheme:

Scheme 4

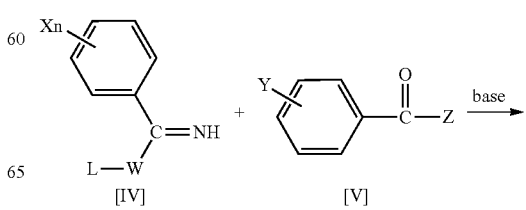

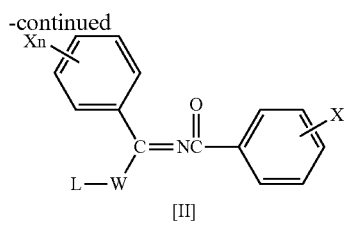

[II]

This process involves usage of more complicated starting materials than those used in deferasirox processes. Such materials are not commercially available and their preparation enlarges the number of steps and needs for intermediate isolation at each step.

Another method presented in the abovementioned patent consists of the reaction of hydrazonoyl chloride [VI] with nitriles via a nitrilium ion (generated from [VI] and aluminum chloride):

Scheme 5

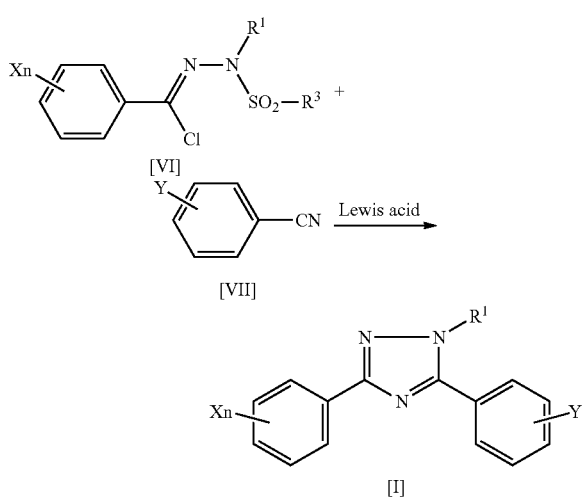

Although this method gives the desired material at a good yield, it is more complicated (high number of steps, commercially unavailable starting materials and intermediates which require further isolation and purification).

Consequently, there is a long-felt need for a process for the preparation deferasirox which not only overcomes the problems in the art processes as mentioned above, but is also safe, cost effective, and industrially feasible.

Polymorphism, the occurrence of different crystal forms, is a property of some molecules and molecular complexes. A single molecule, like deferasirox may give rise to a variety of crystalline forms having distinct crystal structures and physical properties like melting point, x-ray diffraction pattern, infrared absorption fingerprint, and solid state NMR spectrum. One crystalline form may give rise to thermal behavior different from that of another crystalline form. Thermal behavior can be measured in the laboratory by such techniques as capillary melting point, thermogravimetric analysis ("TGA"), and differential scanning calorimetry ("DSC"), which have been used to characterize crystal forms. A new form of a compound may possess physical properties that differ from, and are advantageous over, those of other crystalline or amorphous forms. These include, packing properties such as molar volume, density and hygroscopicity; thermodynamic properties such as melting temperature, vapor pressure and solubility; kinetic properties such as dissolution rate and stability under various storage conditions; surface properties such as surface area, wettability, interfacial tension and shape; mechanical properties such as hardness, tensile strength, compatibility, handling, flow and blend; and better filtration properties. Variations in any one of these properties affect the chemical and pharmaceutical processing of a compound as well as its bioavailability and may often render the new form advantageous for medical use.

Several polymorphs of deferasirox are known in the art. Publication number IPCOM000 146862D describes a crystalline form of deferasirox, designated form I, characterized by X-ray powder diffraction having peaks at about 13.2, 14.1 and 16.6±0.2 degrees 2θ. Form I may be further characterized by X-ray powder diffraction having peaks at about 6.6, 10.0, 10.6, 20.3, 23.1, 25.7 and 26.2±0.2 degrees 2θ and by an X-ray powder diffraction pattern depicted in FIG. 1.

WO 2008/094617, filed by Teva Pharmaceuticals USA, describes three crystalline forms of deferasirox, designated Forms II, III and IV (a THF solvate). WO 2008/065123, filed by Novartis, describes other crystalline forms of deferasirox, designated Forms A, B, C and D, as well as an amorphous form of deferasirox, and deferasirox solvates designated Forms $S_A$ and $S_B$. WO 2009/016359, filed by Pliva Hrvatska D.O.O, describes five crystalline forms of deferasirox, designated Forms I-V, and four amorphous forms designated Forms I-IV.

There still remains an unmet need for advantageous solid state forms of deferasirox having good physiochemical properties, desirable bioavailability, and advantageous pharmaceutical parameters.

SUMMARY OF THE INVENTION

The present invention provides processes for the preparation of deferasirox, which is useful as an oral iron chelator. These processes are referred to hereinafter as "Process A" and "Process B". The present invention further provides novel deferasirox pseudopolymorphs and a novel amorphous form of deferasirox, and processes for their preparation.

Process A:

In one embodiment, the present invention provides a process for preparing a compound of formula I (deferasirox), or its protected analogs, compounds Ia, Ib or Ic, comprising the step of reacting a compound of Formula II:

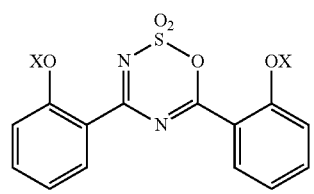

wherein: X is a hydroxyl protecting group, with a compound of Formula III:

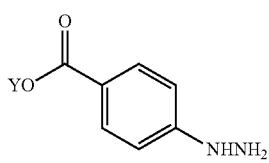

wherein Y is a carboxyl protecting group, in an organic solvent to form the compound of Formula I or Ia, or Ib or Ic,

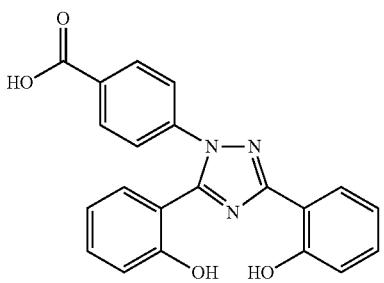

(I)

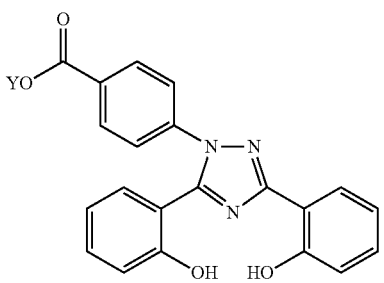

(Ia)

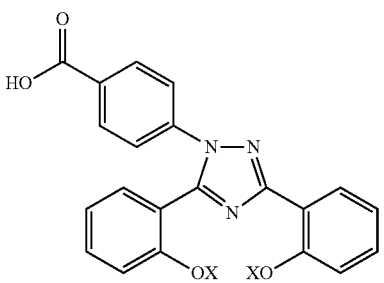

(Ib)

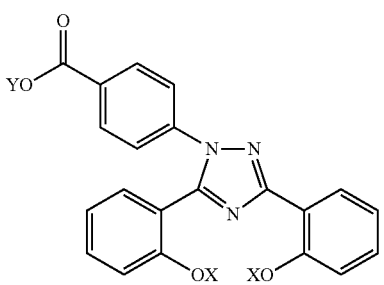

(Ic)

In some embodiments, X is selected from silyl, alkyl and acyl protecting groups. In other embodiments, X is a silyl protecting group, for example trimethylsilyl, triethylsilyl, triisopropylsilyl, tert-butyldiphenylsilyl, tert-butyldimethylsilyl or triphenylsilyl. In a currently preferred embodiment, X is trimethylsilyl. In other embodiments, X is an alkyl protecting group, such as methyl, methoxymethyl (MOM), benzyloxymethyl, methoxyethoxymethyl, 2-(trimethylsilyl)ethoxy-methyl, tetrahydropyranyl, t-butyl or 4-methoxybenzyl. In another embodiment, X is an acyl protecting group, such as —COCH$_3$ (Ac). Each possibility represents a separate embodiment of the invention.

In a currently preferred embodiment, X is methoxymethyl (MOM). In another currently preferred embodiment, X is —COCH$_3$ (Ac).

In some embodiments, Y is selected from silyl, alkyl and aryl carboxy protecting groups. In a currently preferred embodiment, Y is ethyl.

The organic solvent used for the aforementioned reaction can vary, but is generally selected from the group consisting of C1-C4 aliphatic alcohols, C6-C10 aromatic and aliphatic hydrocarbons, C2-C8 aliphatic esters, C4-C8 ethers, C1-C6 halo-substituted alkyl, and C2-C8 aliphatic amides. In some exemplary embodiments, the organic solvent is selected from the group consisting of methanol, ethanol, isopropyl alcohol, n-butanol, t-butyl alcohol, isopropyl alcohol, toluene, benzene, hexanes, cyclohexane, methyl acetate, ethylacetate, t-butylacetate, isopropyl acetate, diisopropyl ether, methyl t-butyl ether, tetrahydrofuran, dioxane, dichloromethane, dichloroethane, chloroform, carbon tetrachloride, tetrachloroethylene, tetrachloroethane, dimethylformamide and dimethylacetamide. Each possibility represents a separate embodiment of the invention.

In some embodiments, compound II is formed by reacting a compound of Formula IV

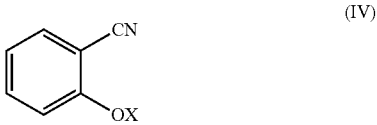

(IV)

with a sulfating reagent, wherein X is a hydroxyl protecting group as described above.

In some embodiments, the sulfating reagent is a sulfur trioxide or a Lewis base complex of sulfur trioxide. For example, the Lewis base complex of sulfur trioxide comprises a Lewis base selected from pyridine, trimethylamine, dimethyl sulfide, sulfolane, triphenylphosphine, triphenylphosphine oxide, trialkylphosphine oxides, trialkylphosphates, dimethylsulfoxide, dimethylformamide, nitromethane, dioxane, and 1,4-oxathiane. In a currently preferred embodiment, the sulfating reagent is trimethylsilyl chloro-sulfonate. In another currently preferred embodiment, the sulfating reagent comprises a sulfur trioxide pyridine complex or a sulfur trioxide dioxane complex. Each possibility represents a separate embodiment of the invention. The sulfur trioxide pyridine complex may, in some embodiments, be generated in situ by reaction of trimethylsilyl chlorosulfonate with pyridine in dioxane.

The molar ratio of the sulfating agent to the compound of formula IV can vary, but is generally about 1:2. The sulfonating reaction is generally performed in a solvent system, preferably an organic solvent or mixture of solvents.

In other embodiments, the present invention provides a process for the preparation of a compound of Formula I (deferasirox), as shown in Scheme 6. The process comprises the steps of:

(a) reacting a compound of Formula IV, wherein X=H with a protecting group reagent XQ wherein Q is a leaving group so as to form a compound of Formula IV, wherein X is a hydroxyl protecting group;

(b) optionally isolating the compound of Formula IV from the reaction mixture and optionally purifying said isolated compound of formula IV;

(c) reacting the compound of Formula IV formed in steps (a) or (b) with a sulfating reagent in the amount of about 1 molar equivalents relative to about 2 molar equivalents of the compound of Formula IV in the presence of an organic solvent to form a compound of Formula II;

(d) optionally isolating the compound of Formula II from the reaction mixture and optionally purifying said isolated compound of formula II;

(e) treating the reaction mixture from step (c) or purified compound from the step (d) with a compound of Formula III in the presence of an organic solvent to form a compound of Formula I, Ia, Ib or Ic; and f) converting a compound of Formula Ia, Ib or Ic to a compound of Formula I.

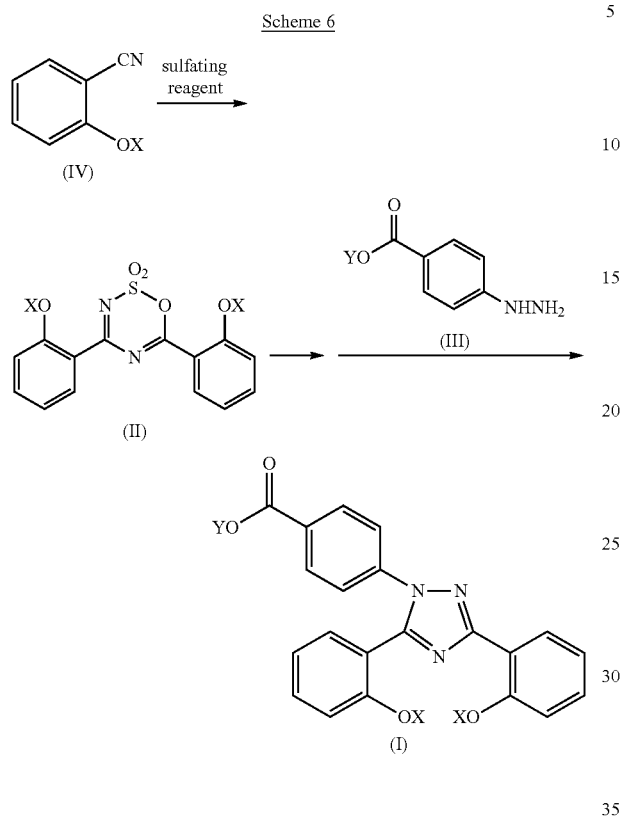

Certain intermediates formed in the process of the present invention are novel and represent separate embodiments of the present invention. Thus, in one embodiment, the present invention is directed to a compound of formula (Ia). In another embodiment, the present invention is directed to a compound of formula (Ib). In another embodiment, the present invention is directed to a compound of formula (Ic). In another embodiment, the present invention is directed to a compound of formula (II).

Process B:

In another embodiment, the applicants have further discovered an additional process for the preparation of deferasirox. This process is exemplified in Scheme 7 below:

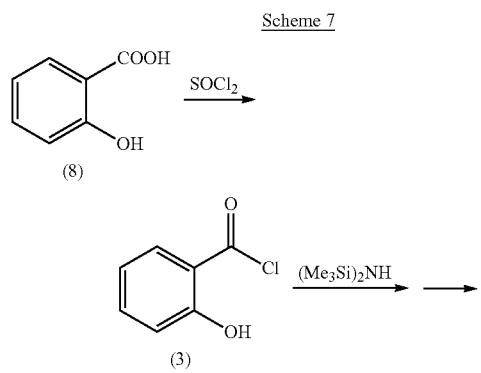

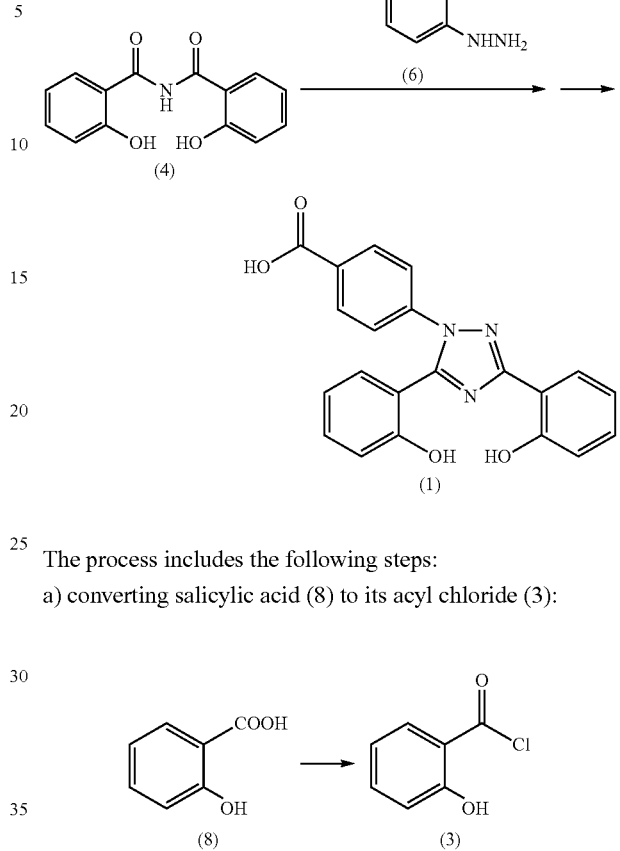

The process includes the following steps:

a) converting salicylic acid (8) to its acyl chloride (3):

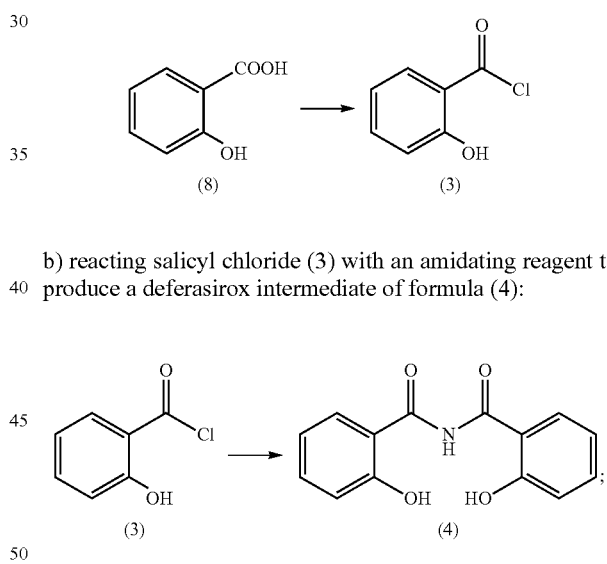

b) reacting salicyl chloride (3) with an amidating reagent to produce a deferasirox intermediate of formula (4):

and c) reacting intermediate (4) with 4-hydrazinobenzoic acid (6) to form deferasirox:

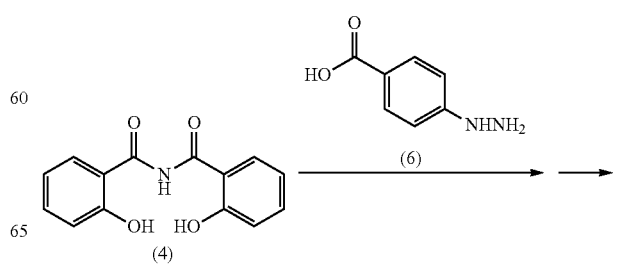

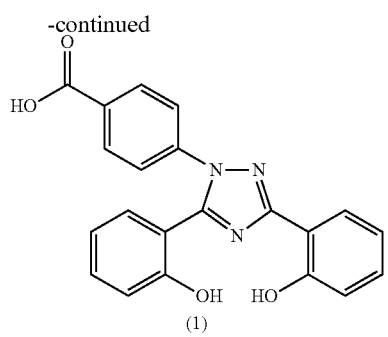

(1)

In some embodiments, the amidating reagent in step (b) is selected from the group consisting of disilazanes of general formula $(R^1R^2R^3Si)_2NH$ and cyclosilazanes of general formula $(R^1R^2SiNH)_n$, wherein n is 3 or 4 and $R^1$, $R^2$ and $R^3$ are each independently alkyl (e.g., C1-C6 alkyl) or aryl. Each possibility represents a separate embodiment of the invention. In a currently preferred embodiment, the amidating reagent is hexamethyldisilazane.

In some embodiments, step (b) is conducted in a solvent. The nature of the solvent can vary, and it is preferably selected from the group consisting of hydrocarbons and their halogenated derivatives, aromatic hydrocarbons and their halogenated derivatives, esters, ethers, carboxylic acid amides such as DMF, acetonitrile, and suitable mixtures of these solvents. Each possibility represents a separate embodiment of the invention. In a currently preferred embodiment, the solvent is toluene.

In some embodiments, in step (b) the reaction between salicyl chloride and the amidating reagent is conducted in the presence of a catalyst. In some embodiments, the catalyst is a tertiary amine such as triethylamine, diisopropylethylamine, N-methylmorpholine, pyridine, lutidine, DBU, DBN, DABCO or picoline, preferably pyridine, or an amide such as DMF and dimethylacetamide. Each possibility represents a separate embodiment of the invention. In one currently preferred embodiment, the catalyst is pyridine. In another currently preferred embodiment, the catalyst is DMF.

Advantageously, step (a) and step (b) of the process of Scheme 7 are combined as a one-pot synthesis. Preferably these steps are conducted in the same solvent, which is preferably toluene.

In other embodiments, step (c) of the process of Scheme 7 is performed in an organic solvent in the presence of acid. The nature of the solvent can vary, and it is preferably selected from the group consisting of alcohols, ethers, DMF, NMP, DMSO, water and mixtures thereof. Each possibility represents a separate embodiment of the invention. In a currently preferred embodiment, the solvent is ethanol.

The acid in step (c) can be an inorganic acid such as hydrochloric acid, hydrobromic, phosphoric or sulfuric acid. Alternatively, the acid can be an organic acid such as formic acid, acetic acid, trifluoroacetic, methanesulfonic or propionic acid. Each possibility represents a separate embodiment of the invention. In a currently preferred embodiment, the acid is trifluoroacetic acid.

Deferasirox Polymorphs

In further embodiments, the present invention provides new polymorphic and pseudo-polymorphic forms of deferasirox, as well as a novel amorphous form of deferasirox, pharmaceutical compositions comprising said compounds, methods for their preparation and use thereof in treating transfusion-dependent chronic iron overload.

The present invention is based in part on the unexpected finding that the new forms disclosed herein possess advantageous physicochemical properties which render their processing as medicaments beneficial. The forms of the present invention have good bioavailability as well as desirable stability characteristics enabling their incorporation into a variety of different formulations particularly suitable for pharmaceutical utility.

According to a first aspect, the present invention provides a crystalline deferasirox hemi-hydrate (Form II) having an X-ray powder diffraction pattern with diffraction peaks at 2-theta values of about 15.6±0.1 and 24.7±0.1.

In one embodiment, the present invention provides a crystalline deferasirox hemi-hydrate (Form II) having an X-ray powder diffraction pattern with diffraction peaks at 2-theta values of about 11.9±0.1, 15.6±0.1, 24.7±0.1 and 25.6±0.1.

In another embodiment, the present invention provides a crystalline deferasirox hemi-hydrate (Form II) having an X-ray powder diffraction pattern with at least 3 diffraction peaks at 2-theta values of about 10.0±0.1, 10.4±0.1, 11.9±0.1, 13.4±0.1, 13.7±0.1, 15.6±0.1, 17.3±0.1, 17.9±0.1, 19.1±0.1, 20.1±0.1, 22.0±0.1, 22.6±0.1, 22.9±0.1, 24.7±0.1, 25.6±0.1, 26.6±0.1, 27.0±0.1, 27.7±0.1, 29.1±0.1, and 32.7±0.1.

In particular embodiments, the present invention provides a crystalline deferasirox hemi-hydrate (Form II) having an X-ray powder diffraction pattern with diffraction peaks at 2-theta values of about 10.0±0.1, 10.4±0.1, 11.9±0.1, 13.4±0.1, 13.7±0.1, 15.6±0.1, 17.3±0.1, 17.9±0.1, 19.1±0.1, 20.1±0.1, 22.0±0.1, 22.6±0.1, 22.9±0.1, 24.7±0.1, 25.6±0.1, 26.6±0.1, 27.0±0.1, 27.7±0.1, 29.1±0.1, and 32.7±0.1.

In other embodiments, the present invention provides a crystalline deferasirox hemi-hydrate (Form II) having an X-ray powder diffraction pattern substantially as shown in FIG. 4. In one embodiment, the crystalline deferasirox hemi-hydrate is further characterized by a DSC profile having endothermic peaks at about 53° C. and about 260° C. In another embodiment, the crystalline deferasirox hemi-hydrate is further characterized by a DSC profile substantially as shown in FIG. 5.

In one embodiment, the crystalline deferasirox hemi-hydrate (Form II) may be prepared by a process comprising the steps of (a) dissolving deferasirox, preferably deferasirox Form I in a solvent selected from DMF and DMSO, wherein the dissolving step is preferably conducted under heat; and adding water as an anti-solvent to precipitate deferasirox Form II.

According to a second aspect, the present invention provides a crystalline deferasirox hemi-DMSO solvate (Form V) having an X-ray powder diffraction pattern with diffraction peaks at 2-theta values of about 25.8±0.1 and 26.2±0.1.

In one embodiment, the present invention provides a crystalline deferasirox hemi-DMSO solvate (Form V) having an X-ray powder diffraction pattern with diffraction peaks at 2-theta values of about 13.3±0.1, 16.7±0.1, 25.8±0.1 and 26.2±0.1

In another embodiment, the present invention provides a crystalline deferasirox hemi-DMSO solvate (Form V) having an X-ray powder diffraction pattern with at least 3 diffraction peaks at 2-theta values of about 6.61±0.1, 10.2±0.1, 10.7±0.1, 13.3±0.1, 14.2±0.1, 15.0±0.1, 15.5±0.1, 16.7±0.1, 17.5±0.1, 17.8±0.1, 19.0.0±0.1, 19.7±0.1, 20.4±0.1, 21.6±0.1, 22.6±0.1, 23.2±0.1, 23.9±0.1, 25.2±0.1, 25.8±0.1, 26.2±0.1, 27.3±0.1, 27.7±0.1, 28.5±0.1, 31.2±0.1, 33.5±0.1, 33.8±0.1, and 34.3±0.1.

In particular embodiments, the present invention provides a crystalline deferasirox hemi-DMSO solvate (Form V) having an X-ray powder diffraction pattern with diffraction peaks at 2-theta values of about 6.6±0.1, 10.2±0.1, 10.7±0.1, 13.3±0.1, 14.2±0.1, 15.0±0.1, 15.5±0.1, 16.7±0.1, 17.5±0.1, 17.8±0.1, 19.0.0±0.1, 19.7±0.1, 20.4±0.1, 21.6±0.1, 22.6±0.1, 23.2±0.1, 23.9±0.1, 25.2±0.1, 25.8±0.1, 26.2±0.1, 27.3±0.1, 27.7±0.1, 28.5±0.1, 31.2±0.1, 33.5±0.1, 33.8±0.1, and 34.3±0.1.

In other embodiments, the present invention provides a crystalline deferasirox hemi-DMSO solvate (Form V) having an X-ray powder diffraction pattern substantially as shown in FIG. 21. In one embodiment, the crystalline deferasirox hemi-DMSO solvate is further characterized by a DSC profile having endothermic peaks at about 89° C. and about 260° C. In another embodiment, the crystalline deferasirox hemi-DMSO solvate is further characterized by a DSC profile substantially as shown in FIG. 22.

In one embodiment, the crystalline deferasirox hemi-DMSO solvate (Form V) may be prepared by a process comprising the steps of (a) dissolving deferasirox, preferably deferasirox Form I in a solvent mixture selected from DMSO:DMF and DMSO:THF, wherein the dissolving step is preferably conducted under heat; and (b) evaporating the solvent to precipitate deferasirox Form V. In a currently preferred embodiment, the ratio of DMSO to DMF or DMSO to THF is about 1:1 v/v.

According to a third aspect, the present invention provides a crystalline deferasirox mono-DMF solvate (Form VI) having an X-ray powder diffraction pattern with diffraction peaks at 2-theta values of about 9.9±0.1 and 16.6±0.1.

In one embodiment, the present invention provides a crystalline deferasirox mono-DMF solvate (Form VI) having an X-ray powder diffraction pattern with diffraction peaks at 2-theta values of about 9.9±0.1, 10.6±0.1, 16.6±0.1 and 20.0±0.1.

In another embodiment, the present invention provides a crystalline deferasirox mono-DMF solvate (Form VI) having an X-ray powder diffraction pattern with at least 3 diffraction peaks at 2-theta values of about 5.3±0.1, 9.9±0.1, 10.3±0.1, 10.6±0.1, 16.0±0.1, 16.6±0.1, 18.8±0.1, 20.0±0.1, 20.7±0.1, 21.4±0.1, 22.7±0.1, 24.0±0.1, 25.7±0.1, 26.8±0.1, 30.1±0.1, 32.3±0.1, 33.6±0.1 and 33.9±0.1.

In particular embodiments, the present invention provides a crystalline deferasirox mono-DMF solvate (Form VI) having an X-ray powder diffraction pattern with diffraction peaks at 2-theta values of about 5.3±0.1, 9.9±0.1, 10.3±0.1, 10.6±0.1, 16.0±0.1, 16.6±0.1, 18.8±0.1, 20.0±0.1, 20.7±0.1, 21.4±0.1, 22.7±0.1, 24.0±0.1, 25.7±0.1, 26.8±0.1, 30.1±0.1, 32.3±0.1, 33.6±0.1 and 33.9101

In other embodiments, the present invention provides a crystalline deferasirox mono-DMF solvate (Form VI) having an X-ray powder diffraction pattern substantially as shown in FIG. 27. In one embodiment, the crystalline deferasirox mono-DMF solvate is further characterized by a DSC profile having endothermic peaks at about 117° C., about 125° C. and about 260° C. In another embodiment, the crystalline deferasirox mono-DMF solvate is further characterized by a DSC profile substantially as shown in FIG. 28.

In one embodiment, the crystalline deferasirox mono-DMF solvate (Form VI) may be prepared by a process comprising the steps of: (a) providing a suspension of deferasirox, preferably deferasirox Form I in a solvent mixture comprising 2-methyl THF:DMF; (b) stirring the suspension; and (c) filtering to provide deferasirox Form VI. In a currently preferred embodiment, the ratio of 2-methyl THF to DMF is about 3:1 v/v.

In yet another aspect, the present invention provides an amorphous form of deferasirox which is characterized by a DSC profile having an exothermic peak at about 140° C. and an endothermic peak at about 260° C. In certain embodiments, the amorphous form of deferasirox is further characterized by an X-ray powder diffraction pattern substantially as shown in FIG. 33. In other embodiments, the amorphous form of deferasirox is further characterized by a DSC profile substantially as shown in FIG. 34. In other embodiments, the amorphous form of deferasirox is further characterized by a TGA profile substantially as shown in FIG. 35.

The amorphous deferasirox may be prepared by a process comprising the steps of: (a) heating a deferasirox, preferably deferasirox Form I to melt; and (b) rapidly cooling the melted deferasirox obtained in step (a), so as to provide amorphous deferasirox.

In other embodiments, the present invention provides processes for preparing a crystalline deferasirox hemi-DMF solvate (Form III), which is characterized by an X-ray powder diffraction pattern with diffraction peaks at 2-theta values of about 9.8±0.1 and 16.5±0.1. In another embodiment, the crystalline deferasirox hemi-DMF solvate (Form III) is further characterized by diffraction peaks at 2-theta values of about 22.4±0.1 and 23.8±0.1. In another embodiment, the crystalline deferasirox hemi-DMF solvate (Form III) is characterized by an X-ray powder diffraction pattern with diffraction peaks at 2-theta values of about 2.9±0.1, 9.1±0.1, 9.8±0.1, 10.1±0.1, 10.5±0.1, 11.6±0.1, 12.5±0.1, 14.4±0.1, 14.8±0.1, 15.4±0.1, 15.8±0.1, 16.5±0.1, 17.5±0.1, 18.0±0.1, 18.7±0.1, 19.8±0.1, 20.5±0.1, 21.4±0.1, 22.4±0.1, 23.1±0.1, 23.8±0.1, 24.3±0.1, 25.0±0.1, 25.6±0.1, 26.6±0.1, 28.0±0.1, 31.1±0.1, 32.1±0.1, 33.5±, 36.0±0.1, and 36.8±0.1. In another embodiment, the crystalline deferasirox hemi-DMF solvate is characterized by an X-ray powder diffraction pattern substantially as shown in FIG. 9. In another embodiment, the crystalline deferasirox hemi-DMF solvate is characterized by a DSC profile substantially as set forth in FIG. 10. In another embodiment, the crystalline deferasirox hemi-DMF solvate is characterized by a DSC profile having endothermic peaks at about 114° C. and about 260° C.

The crystalline deferasirox hemi-DMF solvate (Form III) may be prepared by a process comprising the steps of: (a) providing a suspension of deferasirox, preferably deferasirox Form I in DMF; (b) stirring the suspension; and (c) filtering to provide deferasirox Form III.

Alternatively, the crystalline deferasirox hemi-DMF solvate (Form III) may be prepared by a process comprising the steps of (a) dissolving deferasirox, preferably deferasirox Form I in a solvent mixture selected from DMF:1,4-Dioxane, DMF:THF, DMF:EtOH and DMF: EtOAc, wherein the dissolving step is preferably conducted under heat; and (b) evaporating the solvent to precipitate deferasirox Form III. In a currently preferred embodiment, the ratio of DMF to 1,4-dioxane, THF, EtOH or EtOAc is about 1:1 v/v.

In other embodiments, the present invention provides processes for preparing a crystalline deferasirox mono-THF solvate (Form IV), which is characterized by an X-ray powder diffraction pattern with diffraction peaks at 2-theta values of about 19.8±0.1 and 24.2±0.1. In another embodiment, the deferasirox mono-THF solvate is further characterized diffraction peaks at 2-theta values of about 15.2±0.1 and 20.1±0.1. In another embodiment, the crystalline deferasirox mono-THF solvate (Form IV) is characterized by an X-ray powder diffraction pattern with diffraction peaks at 2-theta values of about 6.8±0.1, 10.0±0.1, 10.6±0.1, 11.8±0.1, 13.5±0.1, 15.2±0.1, 16.6±0.1, 17.7±0.1, 19.2±0.1, 19.8±0.1, 20.1±0.1, 20.8±0.1, 21.9±0.1, 22.4±0.1, 24.2±0.1, 24.7±0.1, 26.0±0.1, 27.4±0.1, 28.3±0.1, 29.4±0.1, 31.1±0.1, 34.4±0.1, 37.6±0.1, 38.4±0.1 and 38.8±0.1. In another embodiment, the crystalline deferasirox mono-THF solvate is characterized by an X-ray powder diffraction pattern substantially as shown in FIG. 15. In another embodiment, the crystalline deferasirox mono-THF solvate is characterized by a DSC profile substantially as set forth in FIG. 16. In another embodiment, the crystalline deferasirox mono-THF solvate is characterized by a DSC profile having endothermic peaks at about 97° C. and about 260° C.

The crystalline deferasirox mono-THF solvate (Form IV) may be prepared by a process comprising the steps of (a) providing a suspension of deferasirox, preferably deferasirox Form I in THF; (b) stirring the suspension; and (c) filtering to provide deferasirox Form IV.

Alternatively, the crystalline deferasirox mono-THF solvate (Form IV) may be prepared by a process comprising the steps of (a) dissolving deferasirox, preferably deferasirox Form I in a solvent mixture selected from THF: MEIN and THF:acetone, wherein the dissolving step is preferably conducted under heat; and (b) evaporating the solvent to precipitate deferasirox Form IV. In a currently preferred embodiment, the ratio of THF to MEK or THF to acetone is about 1:1 v/v.

In yet another embodiment, the present invention provides processes for preparing a crystalline deferasirox Form I characterized by an X-ray diffraction pattern substantially as shown in FIG. 1. The processes comprise the step of drying a deferasirox selected from the group consisting of: the crystalline deferasirox hemi-hydrate (Form II), a crystalline deferasirox hemi-DMSO solvate (Form V), a crystalline deferasirox mono-DMF solvate (Form VI), an amorphous deferasirox and a crystalline deferasirox hemi-DMF solvate (Form III), as those forms are described herein, wherein the drying is conducted at a temperature from about room temperature to about 160° C. In one embodiment, the process is conducted at a temperature of about 120° C. In another embodiment, the drying is conducted at a temperature of about 60° C.

In other embodiments, the present invention provides a pharmaceutical composition comprising as an active ingredient any one of the deferasirox forms of the present invention, i.e., a crystalline deferasirox hemi-hydrate (Form II), a crystalline deferasirox hemi-DMSO solvate (Form V), a crystalline deferasirox mono-DMF solvate (Form VI), or an amorphous deferasirox, and a pharmaceutically acceptable carrier.

In a particular embodiment, the pharmaceutical composition is in the form of a tablet.

In various embodiments, the present invention provides a pharmaceutical composition comprising as an active ingredient any one of the deferasirox forms of the present invention, and a pharmaceutically acceptable carrier for use in treating iron overload.

In some embodiments, the present invention provides a method treating iron overload, comprising administering to a subject in need thereof an effective amount of a composition comprising any one of the deferasirox forms of the present invention, e.g., a crystalline deferasirox hemi-hydrate (Form II), a crystalline deferasirox hemi-DMSO solvate (Form V), a crystalline deferasirox mono-DMF solvate (Form VI), or an amorphous deferasirox.

In additional embodiments, the present invention provides use of any one of the deferasirox forms of the present invention for the preparation of a medicament for treating iron overload. In additional embodiments, the present invention provides use of any one of the deferasirox forms of the present invention for treating iron overload.

In particular embodiments, the iron overload occurs as a consequence of multiple blood transfusions, i.e., is transfusion-dependent chronic iron overload.

In specific embodiments, the subject is a mammal, preferably a human.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

Deferasirox Processes

Figure 1:
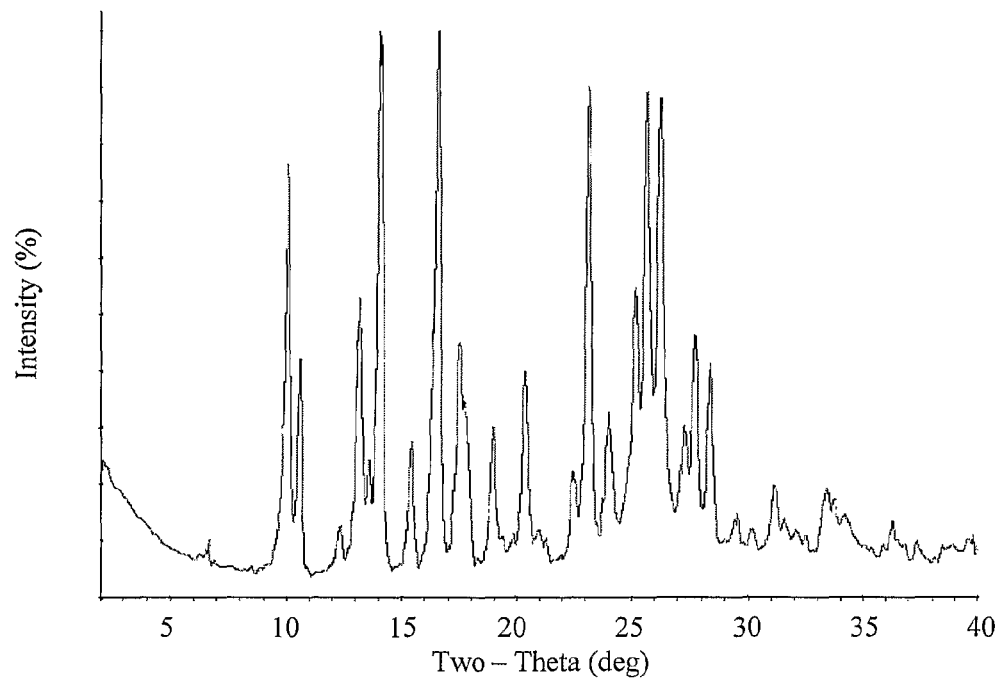
FIG. 1 illustrates a characteristic X-ray diffraction pattern of crystalline Form I of deferasirox.

In some embodiments, the present invention provides synthetic processes for preparing deferasirox, designated herein as Processes A and B.

Process A:

As contemplated herein, Process A comprises the steps of:
(a) reacting a compound of Formula II:

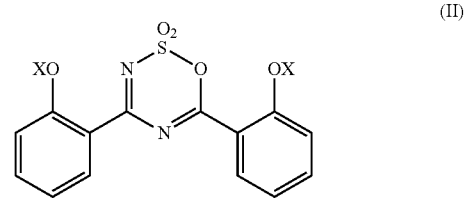

(II)

wherein: X is a hydroxyl protecting group,
with a compound of Formula III,

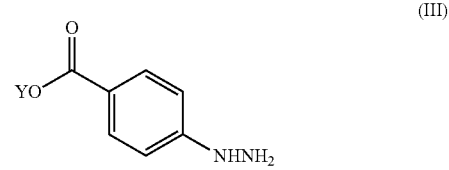

(III)

wherein Y is a carboxyl protecting group, to form a compound of Formula I or Ia, Ib or Ic.

In one embodiment, the compound of formula II is prepared by reacting of compound of Formula IV

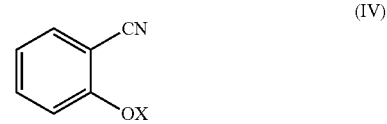

(IV)

wherein X is a hydroxyl protecting group, with a sulfating reagent.

It will be appreciated that the reactions described herein are carried out for a time and under conditions sufficient to produce the desired product, preferably in optimum yield. Reaction conditions are readily determined by a person of skill in the art.

A general outline of some embodiments of Process A of the present invention is provided in Scheme 6 above. As can be seen in Scheme 6, the compound of Formula IV is selectively protected at the phenolic position, and is then reacted with a sulfating agent to afford the compound of Formula II, which is subsequently reacted with a compound of formula (III) to form compound (I), and/or its protected analogs Ia, Ib or Ic. In some embodiments, during the workup of isolating the compound of Formula I from the reaction mixture, the workup conditions are sufficient to remove the protecting groups X and Y of the compound of Formula Ia, Ib and Ic to afford the compound of Formula I. In other embodiments, however, the process of the invention further comprises a step of converting any compound of Formula Ia, Ib or Ic to a compound of formula I, by removal of any remaining hydroxyl and/or carboxy protecting groups.

The hydroxyl protecting group X is added by reacting the compound of Formula IV with a hydroxyl protecting group reagent, which in some embodiments has the structure XQ, where X is a protecting group, and Q is a leaving group that is displaced by the phenolic oxygen atom of the compound of Formula IV (X=H).

Suitable hydroxyl protecting groups include, but are not limited to, silyl protecting groups having the structure —SiRRR; wherein each R is independently, alkyl (e.g., C1-C6 alkyl) or aryl, e.g., phenyl. One currently preferred hydroxyl protecting group is trimethylsilylchloride (TMS), which can be attached to the phenolic hydroxyl of the compound of Formula IV (X=H) by reaction with the hydroxyl protecting group reagent trimethylsilyl chloride or hexamethylsilazane or their mixture.

Other non-limiting examples of suitable hydroxyl protecting groups include alkyl protecting groups such as methyl, methoxymethyl, benzyloxymethyl, methoxyethoxymethyl, 2-(trimethylsilyl)ethoxymethyl, tetrahydropyranyl, t-butyl, 4-methoxybenzyl and analogous groups. One currently preferred hydroxyl protecting group is methoxymethyl (MOM), which can be attached to the phenolic hydroxyl of the compound of Formula IV (X=H) by reaction with dimethoxymethane (methylal). Other suitable hydroxyl protecting groups are acyl groups, such as —COCH$_3$ (Ac).

Other suitable hydroxyl protecting groups and hydroxyl protecting group reagents are disclosed in Greene and Wuts, Protective Groups in Organic Synthesis, 2d ed, John Wiley & Sons, New York, 1991, the disclosure of which is hereby incorporated by reference in its entirety.

Typically, the reaction of the compound of Formula II and the compound of Formula III is performed in a solvent system, preferably an organic solvent that can be a single solvent, or can include a mixture of solvents. A wide variety of suitable solvents can be employed, including ethers (dimethoxymethane, tetrahydrofuran, 1,3-dioxane, 1,4-dioxane, furan, diethyl ether, tetrahydropyran, diisopropyl ether, dibutyl ether, ethylene glycol dimethyl ether, ethylene glycol diethyl ether, diethylene glycol dimethyl ether, diethylene glycol diethyl ether, triethylene glycol dimethyl ether, anisole, and t-butyl methyl ether), dimethylformamide (DMF), dimethylacetamide (DMAC), 1,3-dimethyl-3,4,5,6-tetrahydro-2(1H)-pyrimidinone (DMPU), 1,3-dimethyl-2-imidazolidinone (DMI), N-methylpyrrolidinone (NMP), formamide, N-methylacetamide, N-methylformamide, acetonitrile, dimethyl sulfoxide (DMSO), propionitrile, ethyl formate, methyl acetate, hexachloroacetone, ethyl acetate, sulfolane, N,N-dimethylpropionamide, tetramethylurea, nitrobenzene, or hexamethylphosphoramide, hydrocarbons, halogenated solvents and alcohols.

In some embodiments, the reaction is performed in a solvent system that includes a water miscible solvent and water thus providing the option to perform deprotection and isolation steps in one process stage.

Typically, the compound of Formula II is added to the solvent system at a suitable temperature (for example room temperature), and the solution is then cooled, for example to a temperature less than about 10° C., preferably between about −10° C. and 10° C., for example about 0° C., prior to the addition of the compound of Formula III. The progress of the reaction can be monitored by a variety of techniques, for example by chromatographic techniques such as TLC. Typically, the reaction between the compounds of Formula II and Formula III is completed after about 0.5 hour to about 10 hours. If during this time the reaction is not completed, the reaction mixture may be heated to a temperature between 35° C. and reflux, preferably at 55-60° C. When the reaction is completed, the compound of Formula I, or Ia, Ib, Ic can be isolated from the reaction mixture by standard work-up procedures, for example by filtering the reaction mixture, evaporating the residue, etc. If desired, the product can then be purified by any standard technique, for example by crystallization or flash chromatography over silica. Generally, it is preferable to perform the deprotection step (if such is necessary) prior to the purification. In some embodiments, the deprotection and purification steps are performed as a "one-pot" process. The solvent or mixture of solvents for the purification step can be selected in such a manner that any desired polymorphic form of the compound of Formula I is provided by crystallization or sedimentation from such solvent or mixture of solvents.

Generally, the workup conditions are sufficient to remove the protecting groups X and Y of the compound of Formula Ia, Ib and Ic or to afford the compound of Formula I directly. However, in embodiments where workup conditions are not sufficient to remove the hydroxyl protecting groups X and Y of the compound of Formula Ia, Ib and Ic, the processes of the invention include the further step of removing the protecting groups X and Y. Choice of conditions effective to remove the protecting group will vary depending on the specific protecting group employed, and include for example treatment with acid or base, or a neutral reagent. Removal of the hydroxyl protecting groups is carried out as known to a person of skill in the art.

In some embodiments, the yield of the compound of Formula I is greater than about 55%, 60%, 65%, 75%, 80%, or 85%.

Furthermore, as seen in Scheme 6 above, the compound of Formula II can be prepared by reaction of the compound of Formula IV with a sulfating reagent. Several sulfating reagents are known for sulfation of hydroxyl groups, including aromatic hydroxyl group. In some embodiments, the sulfating reagent is a sulfur trioxide in stabilized form. In some embodiments, the sulfating reagent is complex of sulfur trioxide with a Lewis base. In some embodiments, the sulfating reagent is a complex of sulfur trioxide and an amide, for example, a complex of sulfur trioxide and N,N-dimethylformamide. In some embodiments, the sulfating reagent is a complex of sulfur trioxide and an amine, for example a tertiary amine (including acyclic amines, for example, trimethylamine, triethylamine, dimethylphenylamine and dimethylbenzylamine; cyclic amines, for example, 1-methylpyrrolidine and 1-methylpiperidine; and aromatic amines which have one or more nitrogen atoms as ring-forming atoms of the aromatic ring, for example, 1-methylimidazole, pyridine and pyrimidine). In some embodiments, the sulfating reagent is a sulfur trioxide/pyridine complex. Other complexes of sulfur trioxide and a tertiary amine, for example, sulfur trioxide and trimethylamine complex or sulfur trioxide and triethylamine complex, can also be used as sulfating reagents. In some embodiments, the sulfating reagent is a complex of sulfur trioxide and tertiary phosphines, phosphine oxides and phosphates. In some embodiments, the sulfating reagent is a complex of sulfur trioxide and dimethyl sulfide, sulfolane, dimethylsulfoxide, nitromethane, dioxane, or 1,4-oxathiane.

In some embodiments, the sulfating reagent is trimethylsilyl chlorosulfonate. The reaction of this reagent with pyridine in dioxane generates a sulfur trioxide pyridine complex and liberates trimethylchlorosilane. Reaction of the compound of Formula IV (X=H) with such a mixture provides simultaneous or step-by-step formation of the compound of Formula II (X=SiMe$_3$).

Generally, the sulfating reagent is employed in molar ratio of the sulfating reagent to the compound of Formula IV of about 1:2.

Typically, the reaction of the compound of Formula IV and the sulfating reagent is performed in a solvent system that includes a solvent or mixture of solvents. A wide variety of suitable solvents can be employed, including those describe above, preferably polar aprotic organic solvents, i.e., organic solvents that are not readily deprotonated in the presence of a strongly basic reactant or reagent. In some embodiments, the reaction is performed in a solvent system that includes or consists of dioxine.

The reaction of the compound of Formula IV and the sulfating reagent is generally performed at convenient temperature, for example from about 20° C. to about 60° C. Generally, the reaction temperature can be raised to accelerate the rate of the reaction. In some embodiments, the reaction mixture is heated to reflux in the solvent system of the reaction. Typically, the compound of Formula IV is dissolved in solvent, and the sulfating agent is added slowly. The progress of the reaction can be monitored by a variety of techniques, for example by chromatographic techniques (preferably, TLC). The reaction between the compound of Formula II and the sulfating reagent is generally complete after about 0.5 hour to about 2 days.

The processes described herein can be monitored according to any suitable method known in the art. For example, product formation can be monitored by spectroscopic means, such as nuclear magnetic resonance spectroscopy (e.g., 1H or 13C), infrared spectroscopy, spectrophotometry (e.g., UV-visible), or mass spectrometry, or by chromatography such as high performance liquid chromatography (HPLC) or thin layer chromatography.

The reactions of the processes described herein can be carried out in air or under an inert atmosphere. Typically, reactions containing reagents or products that are substantially reactive with air can be carried out using air-sensitive synthetic techniques that are well known to the skilled artisan.

Upon carrying out preparation of compounds according to the processes described herein, the usual isolation and purification operations such as concentration, filtration, extraction, solid-phase extraction, recrystallization, chromatography, and the like may be used to isolate the desired products.

The deferasirox product of Process A can be in polymorphic, pseudopolymorphic or amorphous forms, or any mixtures thereof.

Process B:

In another embodiment of the present invention, the applicants have discovered an alternative new process (designated herein "Process B"), by which deferasirox may be prepared on an industrial scale from the compound of formula (8) in three steps (Scheme 7 above). The process is described in details in the discussion and examples below.

Salicylic acid, 4-hydrazinobenzoic acid and hexamethyldisilazane, which are used here as raw materials, are commercially available reagents.

In one embodiment, the present invention relates to a process for preparing a deferasirox intermediate (3), which comprises the steps of converting salicylic acid to its acyl chloride by reaction with chlorinating reagent, preferably in the presence of a catalyst in an organic solvent.

Suitable chlorinating agents can be thionyl chloride, oxalyl chloride, phosgene, POCl$_3$, PCl$_3$, PCl$_5$, cyanuric chloride, combination of triorganophosphine, such as triphenylphosphine with carbon tetrachloride and the like. Each possibility represents a separate embodiment of the present invention. In one currently preferred embodiment, the chlorinating agent is thionyl chloride.

The catalyst can be a tertiary amine such as triethylamine, diisopropylethylamine, N-methylmorpholine, pyridine, lutidine, DBU, DBN, DABCO and picoline, preferably pyridine or amide, such as DMF and dimethylacetamide.

The present invention further relates to a process for preparing a deferasirox intermediate (4), which comprises reacting salicyl chloride (3) with amidating reagent.

Examples of the amidating reagents include, but are not limited to disilazanes of general formula $(R^1R^2R^3Si)_2NH$ and cyclosilazanes of general formula $(R^1R^2SiNH)_n$, wherein n=3, 4, and each of $R^1$, $R^2$ and $R^3$ is alkyl (e.g., C1-C6 alkyl) or aryl. Each possibility represents a separate embodiment of the present invention.

In one currently preferred embodiment, the amidating agent is hexamethyldisilazane. The unique role of hexamethylsilazane in this reaction is due to the multifunctional nature of silazanes. These can be amidating reagents and can also serve as a hydrogen chloride acceptors and protecting groups for OH— groups, thus overcoming the problems in the art processes, i.e. formation of polyesters side products as well as corrosive and hazardous HCl gas. Furthermore, the reaction can proceed efficiently at lower temperatures (e.g. 5-10° C.).

In one embodiment of the process of the invention, salicyl chloride reacts with hexamethyldisilazane to form trimethylsilylamide (9) and trimethylchlorosilane. Trimethylchlorosilane reacts with the OH— group of compound (9), forming a protected compound (10) while liberating HCl, which is trapped by hexamethyldisilazane forming the inactive ammonium chloride as an insoluble solid. It is contemplated that protection of the hydroxyl group of compound (9) prevents formation of linear and cyclic polyesters, such as compound (7). Further reaction of protected compound (10) with salicyl chloride (3) gives protected amide (11), which is converted by conventional work-up to the desired amide (4) (Scheme 8):

Scheme 8

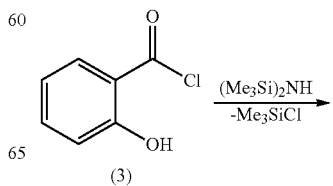

(3)

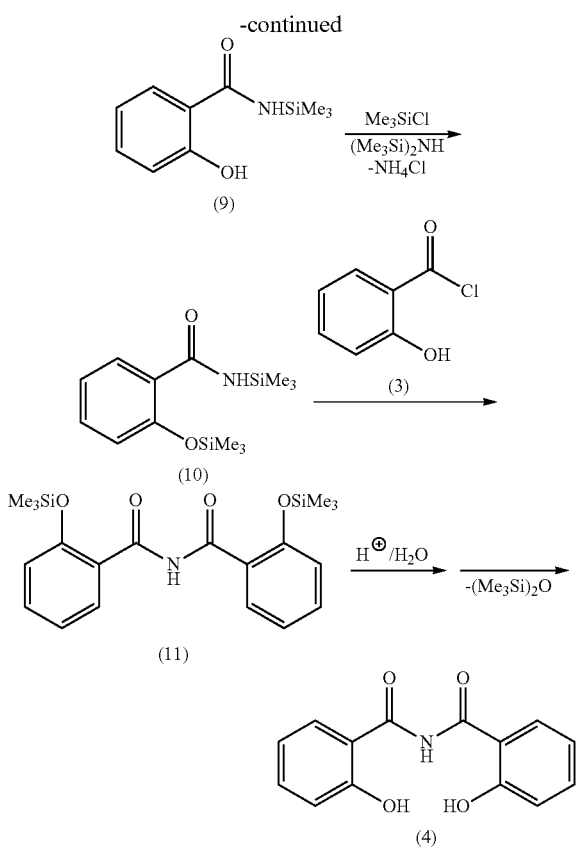

The reaction is conducted in any suitable solvent, which may, for example, be selected from the group consisting of aliphatic hydrocarbons and their halogenated derivatives, aromatic hydrocarbons and their halogenated derivatives, esters, ethers, nitriles, ketones, carboxylic acid amides, as DMF, acetonitrile, and suitable mixtures of these solvents. Each possibility represents a separate embodiment of the present invention. A currently preferred solvent is hexane or toluene.

The reaction may be catalyzed by addition of tertiary amines such as triethylamine, diisopropylethylamine, N-methylmorpholine, pyridine, lutidine, N-ethylpiperidine, DBU, DBN, DABCO and picoline, preferably pyridine or amide, such as DMF and dimethylacetamide.

If required, the reaction may be performed in an inert gas atmosphere such as argon or nitrogen.

Typically, the salicyl chloride is added to the solvent system at a suitable temperature (for example room temperature), and this mixture is added to a solution of an amidating agent such as hexamethyldisilazane in the same solvent. The progress of the reaction can be monitored by a variety of techniques, for example by chromatographic techniques as described above for process A. Typically, the reaction between salicyl chloride and hexamethyldisilazane is completed after about 2 hour to about 12 hours. If during this time the reaction is not completed, the reaction mixture is heated to reflux. The reflux temperature depends on the choice of the solvent used for this reaction. When the reaction is completed, the product (4) can be isolated from the reaction mixture by standard work-up procedures, for example by filtering the reaction mixture followed by evaporation of the filtrate. If desired, the product can then be purified by any standard technique, for example by crystallization or flash chromatography over silica.

The present invention further provides a process for preparing a deferasirox intermediate (4), in which the steps of salicyl chloride preparation and reaction of such chloride with hexamethyldisilazane can be performed as "one-pot" process. In this case the solvent using at the step (a) can be the same as at the step (b), for example, it can be toluene.

The present invention comprises a process for preparing deferasirox which comprises reaction of amide (4) with 4-hydrazinobenzoic acid (6). The conditions for such reaction can be determined by a person of skill in the art. Generally, condensation of hydrazines with diacylamines is well known in the literature [Potts, Chemical Reviews, 1961, 61(2): 87-127]. Such reactions occur in the absence of solvents at high temperatures and are termed Pellizzari reactions [Pellizzari, Gazzita, 1911, 41, II, 20].

The applicants found that the reaction of the amide (4) with 4-hydrazinobenzoic acid (6) can be performed in solvents in the presence of acid yielding the required triazole (1). Suitable solvents to be used in such reaction include, but are not limited to alcohols, ethers, DMF, NMP, DMSO, water or suitable mixtures of these solvents. Each possibility represents a separate embodiment of the present invention. Preferred solvents are alcohols, such as methanol, ethanol, isopropanol or their mixtures with water, more preferable, ethanol.

Suitable acids are inorganic acids, such as hydrochloric acid, hydrobromic, phosphoric or sulfuric acid; or organic acids, such as formic acid, acetic acid, trifluoroacetic, methanesulfonic or propionic acid. Preference is given to organic acids, such as acetic acid, trifluoroacetic, methanesulfonic acids and special preference is given to trifluoroacetic acid.

The product may be isolated from the reaction mixture by ordinary methods, and it can be easily purified in terms of impurities, byproducts, contaminants, and the like by means of separation, for example, crystallization or chromatography.

The solvent or mixture of solvents for the purification step can be selected in such manner that any desired polymorphic form of the compound of Formula I is provided by crystallization or precipitation from such solvent or mixture of solvents.

The deferasirox product of Process B can be in polymorphic, pseudopolymorphic or amorphous forms, or any mixtures thereof.

Chemical Definitions:

An "alkyl" group as used herein refers to any saturated aliphatic hydrocarbon, including straight-chain, branched-chain and cyclic alkyl groups (cycloalkyl). In one embodiment, the alkyl group has 1-12 carbons designated here as $C_1$-$C_{12}$-alkyl. In another embodiment, the alkyl group has 1-6 carbons designated here as $C_1$-$C_6$-alkyl. In another embodiment, the alkyl group has 1-4 carbons designated here as $C_1$-$C_4$-alkyl. The alkyl group may be unsubstituted or substituted by one or more groups including, but not limited to from halogen, hydroxy, alkoxy, aryloxy, carbonyl, amido, alkylamido, dialkylamido, nitro, amino, alkylamino, dialkylamino, carboxyl, thio and thioalkyl.

A "cycloalkyl" group refers to a non-aromatic mono- or multicyclic ring system. In one embodiment, the cycloalkyl group has 3-10 carbon atoms. In another embodiment, the cycloalkyl group has 5-10 carbon atoms. Exemplary monocyclic cycloalkyl groups include cyclopentyl, cyclohexyl, cycloheptyl and the like. An alkylcycloalkyl is an alkyl group as defined herein bonded to a cycloalkyl group as defined herein. The cycloalkyl group can be unsubstituted or substituted with any one or more of the substituents defined above for alkyl.

An "aryl" group refers to an aromatic ring system containing from 6-14 ring carbon atoms. The aryl ring can be a monocyclic, bicyclic, tricyclic and the like. Non-limiting examples of aryl groups are phenyl, naphthyl including 1-naphthyl and 2-naphthyl, and the like. The aryl group can be unsubstituted or substituted through available carbon atoms with one or more groups defined hereinabove for alkyl.

A "silyl" group refers to a group SiRRR, wherein each R is independently, alkyl or aryl as described above.

An "acyl" group refers to a C(=O)R group wherein R is alkyl or aryl as described above.

Deferasirox New Forms

The present invention is directed to novel polymorphic, pseudopolymorphic and amorphous forms of 4-[3,5-Bis(2-hydroxyphenyl)-1H-1,2,4-triazol-1-yl]benzoic acid (deferasirox), which can be represented by the following structural Formula (1):

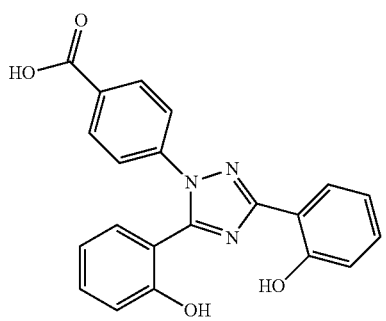

(1)

The present invention is further directed to pharmaceutical compositions comprising the pseudopolymorphic forms, as well as a novel amorphous form of the compound of the present invention and a pharmaceutically acceptable carrier and their use in treating iron overload.

Polymorphs are two or more solid state phases of the same chemical compound that possess different arrangement and/or conformation of the molecules. Pseudopolymorphs are polymorphs which incorporate one or more solvents into the structure. Different polymorphs and pseudopolymorphs of an active pharmaceutical compound can exhibit different physical and chemical properties such as color, stability, processability, dissolution and even bioavailability.

An important physical property of a compound used as an active ingredient of a medicament is the stability at ambient conditions, especially to moisture, and under storage conditions. The identification and characterization of various polymorphs and pseudopolymorphs of a pharmaceutically active compound is therefore of great significance in obtaining medicaments with desired properties including a specific dissolution rate, milling property, bulk density, thermal stability or shelf-life. The deferasirox forms of the present invention possess improved characteristics of hygroscopicity, bulk density and solubility in aqueous media. Furthermore, the deferasirox forms of the present invention have improved chemical and solid state stability. Hence, these forms may be more stable when stored over prolonged periods of time.

Deferasirox Form II:

According to one aspect, the present invention provides a crystalline deferasirox hemi-hydrate (Form II). The crystalline deferasirox Form II contains approximately 2.1% $H_2O$ as indicated by TGA. The crystalline deferasirox Form II is a hemi-hydrate, i.e., it contains approximately 0.5 molecules of $H_2O$ to 1 molecule of deferasirox.

The crystalline deferasirox hemi-hydrate (Form II) is characterized by an X-ray powder diffraction pattern with diffraction peaks at 2-theta values of about 15.6±0.1 and 24.7±0.1. In one embodiment, the crystalline deferasirox hemi-hydrate (Form II) is characterized by diffraction peaks at 2-theta values of about 11.9±0.1, 15.6±0.1, 24.7±0.1 and 25.6±0.1. In another embodiment, the crystalline deferasirox hemi-hydrate (Form II) is characterized by at least 3 X-ray diffraction peaks selected from about 10.0±0.1, 10.4±0.1, 11.9±0.1, 13.4±0.1, 13.7±0.1, 15.6±0.1, 17.3±0.1, 17.9±0.1, 19.1±0.1, 20.1±0.1, 22.0±0.1, 22.6±0.1, 22.9±0.1, 24.7±0.1, 25.6±0.1, 26.6±0.1, 27.0±0.1, 27.7±0.1, 29.1±0.1, and 32.7±0.1 degrees 2-theta. In particular embodiments, the crystalline deferasirox hemi-hydrate (Form II) is characterized by an X-ray powder diffraction pattern with diffraction peaks at 2-theta values of about 10.0±0.1, 10.4±0.1, 11.9±0.1, 13.4±0.1, 13.7±0.1, 15.6±0.1, 17.3±0.1, 17.9±0.1, 19.1±0.1, 20.1±0.1, 22.0±0.1, 22.6±0.1, 22.9±0.1, 24.7±0.1, 25.6±0.1, 26.6±0.1, 27.0±0.1, 27.7±0.1, 29.1±0.1, and 32.7±0.1.

In particular embodiments, the present invention provides a crystalline deferasirox hemi-hydrate (Form II) having an X-ray powder diffraction pattern characterized by diffraction peaks as set forth in Table 1:

TABLE 1

| 2-theta | d-spacing | BG | Height | H % | Area | A % | FWHM | XS | P/N |
|---|---|---|---|---|---|---|---|---|---|
| 9.961 | 8.8730 | 24 | 169 | 25.2 | 75.6 | 35.2 | 0.443 | 203 | 5.6 |
| 10.419 | 8.4834 | 24 | 278 | 41.5 | 85.7 | 39.9 | 0.287 | 349 | 7.6 |
| 11.862 | 7.4544 | 30 | 293 | 43.6 | 77.4 | 36.0 | 0.251 | 420 | 7.7 |
| 13.398 | 6.6031 | 31 | 192 | 28.6 | 78.8 | 36.7 | 0.416 | 219 | 5.8 |
| 13.700 | 6.4585 | 32 | 121 | 18.1 | 96.2 | 44.8 | 0.916 | 91 | 4.1 |
| 15.558 | 5.6911 | 40 | 671 | 100.0 | 214.9 | 100.0 | 0.290 | 346 | 12.2 |
| 17.319 | 5.1160 | 52 | 143 | 21.2 | 55.3 | 25.8 | 0.518 | 171 | 3.8 |
| 17.878 | 4.9573 | 55 | 134 | 20.0 | 31.7 | 14.8 | 0.340 | 282 | 3.4 |
| 19.080 | 4.6478 | 60 | 251 | 37.4 | 89.3 | 41.6 | 0.397 | 234 | 6.0 |
| 20.060 | 4.4228 | 65 | 134 | 19.9 | 36.1 | 16.8 | 0.452 | 201 | 2.9 |
| 21.960 | 4.0443 | 68 | 158 | 23.6 | 43.9 | 20.5 | 0.413 | 224 | 3.6 |
| 22.580 | 3.9346 | 68 | 248 | 36.9 | 88.2 | 41.1 | 0.417 | 221 | 5.7 |
| 22.899 | 3.8806 | 68 | 112 | 16.7 | 94.7 | 44.1 | 1.826 | 45 | 2.1 |
| 24.679 | 3.6044 | 71 | 453 | 67.5 | 152.0 | 70.8 | 0.339 | 286 | 9.0 |
| 25.580 | 3.4795 | 68 | 341 | 50.8 | 151.0 | 70.3 | 0.470 | 194 | 7.4 |
| 26.540 | 3.3558 | 68 | 261 | 39.0 | 116.5 | 54.2 | 0.512 | 176 | 6.0 |
| 26.980 | 3.3021 | 71 | 145 | 21.7 | 41.0 | 19.1 | 0.470 | 194 | 3.1 |
| 27.700 | 3.2178 | 78 | 239 | 35.6 | 56.4 | 26.2 | 0.297 | 341 | 5.2 |
| 29.099 | 3.0662 | 65 | 118 | 17.6 | 53.5 | 24.9 | 0.859 | 100 | 2.4 |
| 32.680 | 2.7380 | 47 | 112 | 16.7 | 43.8 | 20.4 | 0.576 | 156 | 3.1 |

Figure 4:
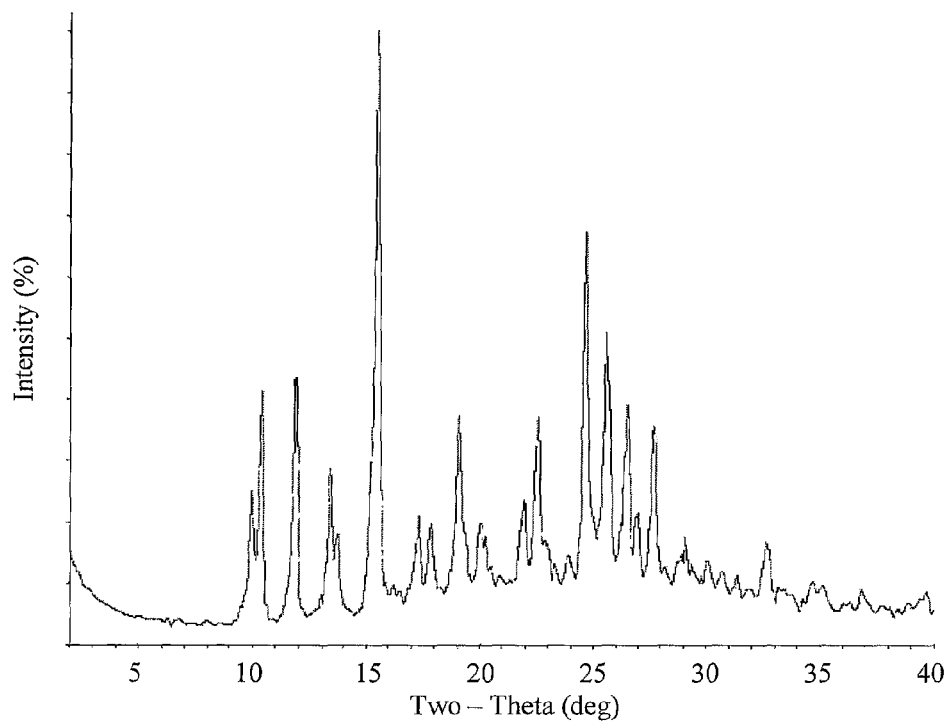
FIG. 4 illustrates a characteristic X-ray diffraction pattern of crystalline Form II of deferasirox (hemi-hydrate).
Figure 5:
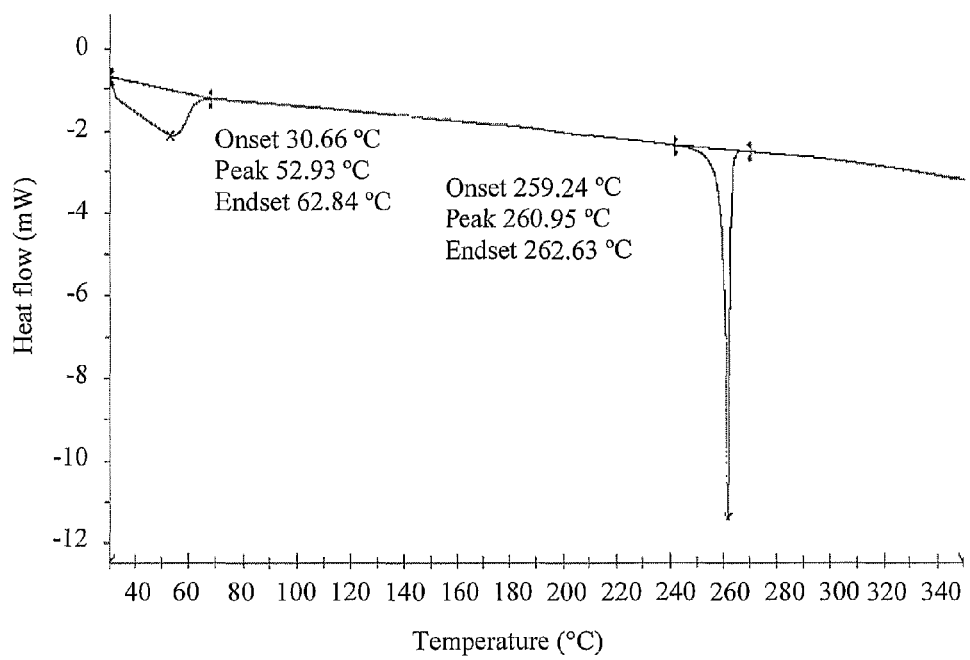
FIG. 5 illustrates a characteristic Differential Scanning calorimetry (DSC) profile of crystalline Form II of deferasirox (hemi-hydrate).
Figure 6:
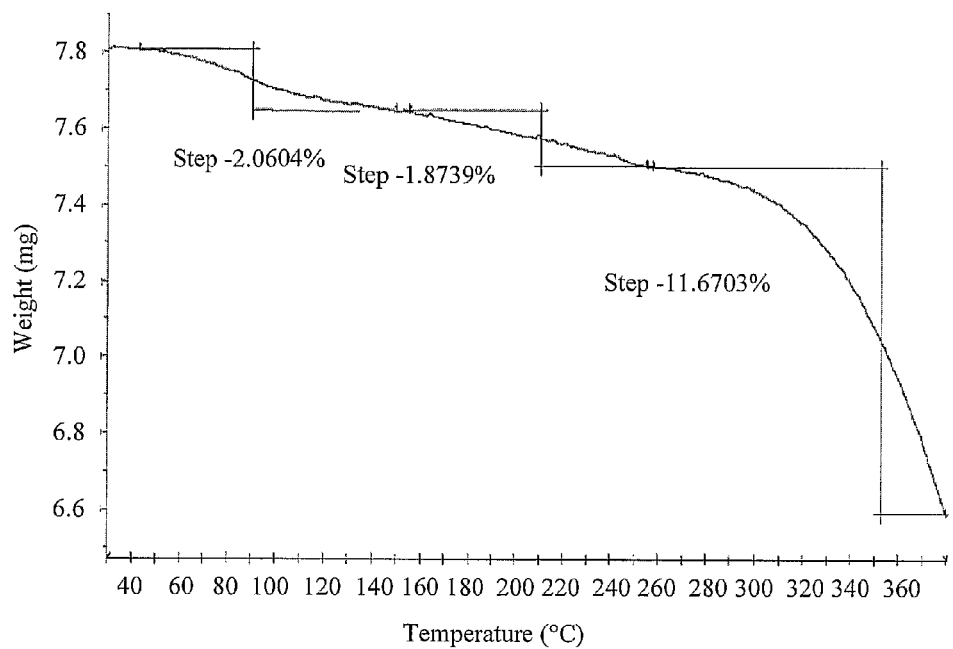
FIG. 6 illustrates a characteristic Thermogravimetric analysis (TGA) profile of crystalline Form II of deferasirox (hemi-hydrate).

Scan: 2.0/40.0/0.02/0.12(sec), Cu (40 kV, 40 mA), I(max) = 671
Peak: 25(pts)/Parabolic Filter, Threshold = 4.0, Cutoff = 3.0%, BG = 3/3.0, Peak-Top = Summit In other embodiments, the crystalline deferasirox hemi-hydrate (Form II) is characterized by an X-ray powder diffraction pattern substantially as shown in FIG. 4. In one embodiment, the crystalline deferasirox hemi-hydrate is further characterized by a DSC profile having endothermic peaks at about 53° C. and about 260° C. In another embodiment, the crystalline deferasirox hemi-hydrate is further characterized by a DSC profile substantially as shown in FIG. 5. In another embodiment, the crystalline deferasirox hemi-hydrate is further characterized by a TGA profile substantially as shown in FIG. 6.

The crystalline deferasirox hemi-hydrate (Form II) converted to Form I after being heated to 60° C. for 1 hr. The XRPD and DSC profiles of Form II before and after the dehydration process are set forth in FIGS. 7 and 8, respectively. Also shown in FIGS. 7 and 8 for comparison are the X-ray diffraction pattern and DSC profile of deferasirox Form I ("DFX-API"), respectively.

In one embodiment, the crystalline deferasirox hemi-hydrate (Form II) may be prepared by a process comprising the steps of (a) dissolving deferasirox, preferably deferasirox Form I in a solvent selected from DMF and DMSO, wherein the dissolving step is preferably conducted under heat; and adding water as an anti-solvent to precipitate deferasirox Form II. Preferably, the dissolving step is conducted at a temperature of about 50° C. to about 100° C., more preferably at a temperature of about 80° C. The solution of deferasirox in DMF or DMSO can be filtered prior to the addition of water.

In one embodiment, the crystalline deferasirox hemi-DMSO solvate (Form V) is characterized by an X-ray powder diffraction pattern with diffraction peaks at 2-theta values of about 25.8±0.1 and 26.2±01. In another embodiment, the crystalline deferasirox hemi-DMSO solvate (Form V) is characterized by an X-ray powder diffraction pattern with diffraction peaks at 2-theta values of about 13.3±0.1, 16.7±0.1, 25.8±0.1 and 26.2±01. In another embodiment, crystalline deferasirox hemi-DMSO solvate (Form V) is characterized by at least 3 X-ray diffraction peaks selected from about 6.6±0.1, 10.2±0.1, 10.7±0.1, 13.3±0.1, 14.2±0.1, 15.0±0.1, 15.5±0.1, 16.7±0.1, 17.5±0.1, 17.8±0.1, 19.0.0±0.1, 19.7±0.1, 20.4±0.1, 21.6±0.1, 22.6±0.1, 23.2±0.1, 23.9±0.1, 25.2±0.1, 25.8±0.1, 26.2±0.1, 27.3±0.1, 27.7±0.1, 28.5±0.1, 31.2±0.1, 33.5±0.1, 33.8±0.1, and 34.3±0.1 degrees 2-theta. In another embodiment, the crystalline deferasirox hemi-DMSO solvate (Form V) is characterized by an X-ray powder diffraction pattern with diffraction peaks at 2-theta values of about 6.6±0.1, 10.2±0.1, 10.7±0.1, 13.3±0.1, 14.2±0.1, 15.0±0.1, 15.5±0.1, 16.7±0.1, 17.5±0.1, 17.8±0.1, 19.0.0±0.1, 19.7±0.1, 20.4±0.1, 21.6±0.1, 22.6±0.1, 23.2±0.1, 23.9±0.1, 25.2±0.1, 25.8±0.1, 26.2±0.1, 27.3±0.1, 27.7±0.1, 28.5±0.1, 31.2±0.1, 33.5±0.1, 33.8±0.1, and 34.3±0.1.

In particular embodiments, the present invention provides a crystalline deferasirox hemi-DMSO solvate (Form V) having an X-ray powder diffraction pattern characterized by diffraction peaks as set forth in Table 2:

TABLE 2

| 2-theta | d-spacing | BG | Height | H % | Area | A % | FWHM | XS | P/N |
|---|---|---|---|---|---|---|---|---|---|
| 6.600 | 13.3814 | 24 | 208 | 39.3 | 47.4 | 11.9 | 0.219 | 513 | 6.4 |
| 10.160 | 8.6997 | 22 | 238 | 44.8 | 88.5 | 22.3 | 0.349 | 271 | 7.0 |
| 10.679 | 8.2779 | 22 | 125 | 23.6 | 28.1 | 7.1 | 0.231 | 473 | 4.6 |
| 13.338 | 6.6327 | 29 | 436 | 82.2 | 155.5 | 39.2 | 0.325 | 296 | 9.7 |
| 14.182 | 6.2400 | 32 | 365 | 68.8 | 109.7 | 27.6 | 0.280 | 361 | 8.7 |
| 15.040 | 5.8857 | 36 | 140 | 26.5 | 41.6 | 10.5 | 0.338 | 283 | 4.4 |
| 15.481 | 5.7191 | 36 | 100 | 18.8 | 17.7 | 4.4 | 0.236 | 461 | 3.2 |
| 16.718 | 5.2988 | 42 | 409 | 77.2 | 134.5 | 33.9 | 0.312 | 314 | 9.1 |
| 17.480 | 5.0693 | 47 | 227 | 42.8 | 99.7 | 25.1 | 0.471 | 191 | 6.0 |
| 17.818 | 4.9740 | 49 | 146 | 27.6 | 77.1 | 19.4 | 0.674 | 128 | 4.0 |
| 18.998 | 4.6675 | 60 | 154 | 29.1 | 45.4 | 11.4 | 0.410 | 225 | 3.8 |
| 19.740 | 4.4937 | 58 | 240 | 45.3 | 92.6 | 23.3 | 0.432 | 212 | 5.9 |
| 20.360 | 4.3583 | 61 | 229 | 43.2 | 80.4 | 20.3 | 0.406 | 228 | 5.6 |
| 21.600 | 4.1108 | 69 | 154 | 29.0 | 46.9 | 11.8 | 0.470 | 192 | 3.4 |
| 22.599 | 3.9313 | 70 | 174 | 32.8 | 28.7 | 7.2 | 0.234 | 471 | 3.9 |
| 23.238 | 3.8247 | 72 | 407 | 76.8 | 97.9 | 24.6 | 0.248 | 433 | 8.3 |
| 23.940 | 3.7141 | 70 | 285 | 53.8 | 101.8 | 25.6 | 0.402 | 232 | 6.4 |
| 25.200 | 3.5311 | 70 | 240 | 45.3 | 173.6 | 43.7 | 0.867 | 99 | 5.5 |
| 25.759 | 3.4557 | 74 | 465 | 87.7 | 379.1 | 100.0 | 0.862 | 99 | 9.1 |
| 26.179 | 3.4013 | 70 | 530 | 100.0 | 278.8 | 70.2 | 0.514 | 175 | 10.0 |
| 27.280 | 3.2664 | 71 | 139 | 26.2 | 24.8 | 6.2 | 0.308 | 325 | 2.9 |
| 27.720 | 3.2156 | 69 | 216 | 40.7 | 74.5 | 18.8 | 0.430 | 215 | 5.0 |
| 28.460 | 3.1336 | 65 | 229 | 43.2 | 69.0 | 17.4 | 0.358 | 270 | 5.4 |
| 31.239 | 2.8609 | 52 | 96 | 18.1 | 33.7 | 8.5 | 0.654 | 135 | 2.2 |
| 33.480 | 2.6744 | 45 | 115 | 21.7 | 82.5 | 20.8 | 1.008 | 86 | 3.2 |
| 33.799 | 2.6498 | 45 | 99 | 18.7 | 59.9 | 15.1 | 0.945 | 92 | 2.7 |
| 34.279 | 2.6138 | 44 | 86 | 16.2 | 59.9 | 15.1 | 1.202 | 71 | 2.3 |

Scan: 2.0/40.0/0.02/0.12(sec), Cu (40 kV, 40 mA), I(max) = 530.
Peak: 27(pts)/Parabolic Filter, Threshold = 4.0, Cutoff = 3.0%, BG = 3/3.0, Peak-Top = Summit Deferasirox Form V:

According to another aspect, the present invention provides a crystalline deferasirox hemi-DMSO solvate (Form V). The crystalline deferasirox Form V contains approximately 7.3% DMSO as indicated by TGA and NMR. The crystalline deferasirox Form V is a hemi-DMSO solvate, i.e., it contains approximately 0.5 molecules of DMSO to 1 molecule of deferasirox.

Figure 21:
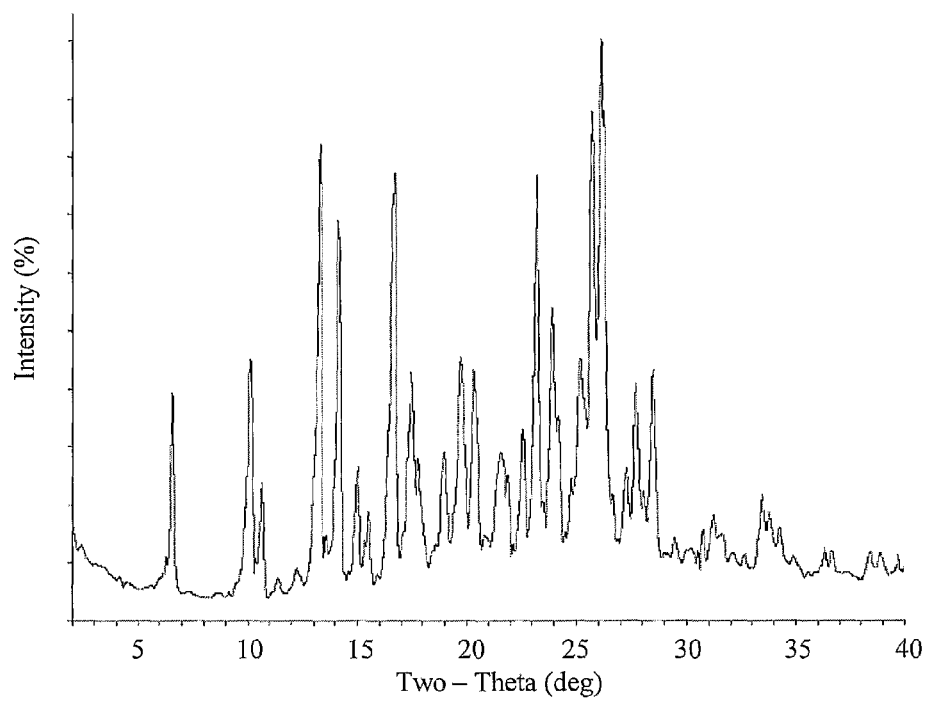
FIG. 21 illustrates a characteristic X-ray diffraction pattern of crystalline Form V of deferasirox (hemi-DMSO solvate).
Figure 22:
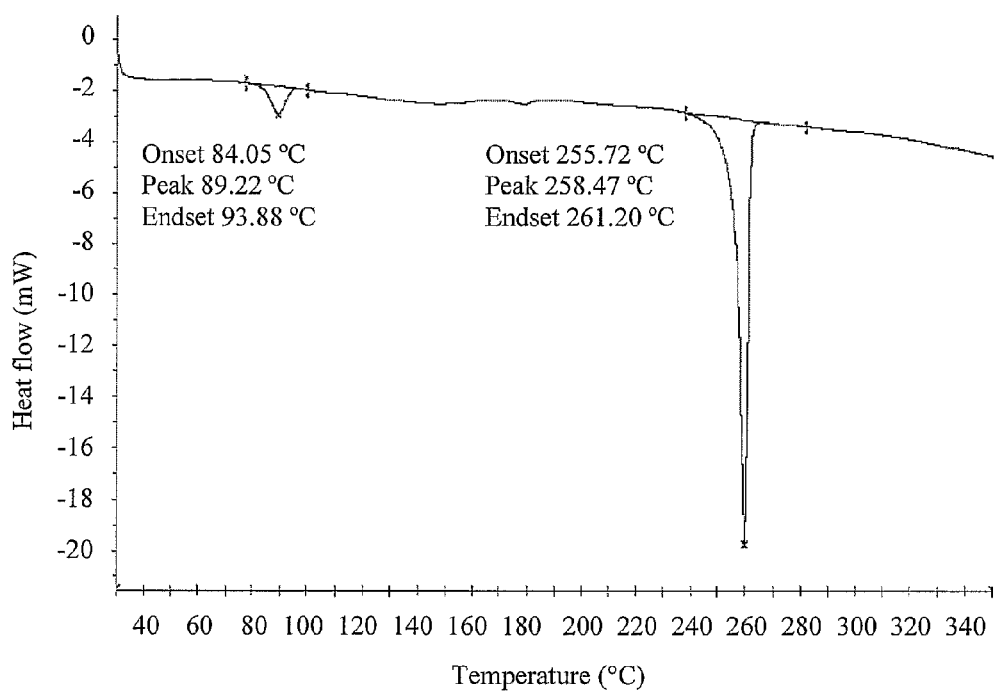
FIG. 22 illustrates a characteristic Differential Scanning calorimetry (DSC) profile of crystalline Form V of deferasirox (hemi-DMSO solvate).
Figure 23:
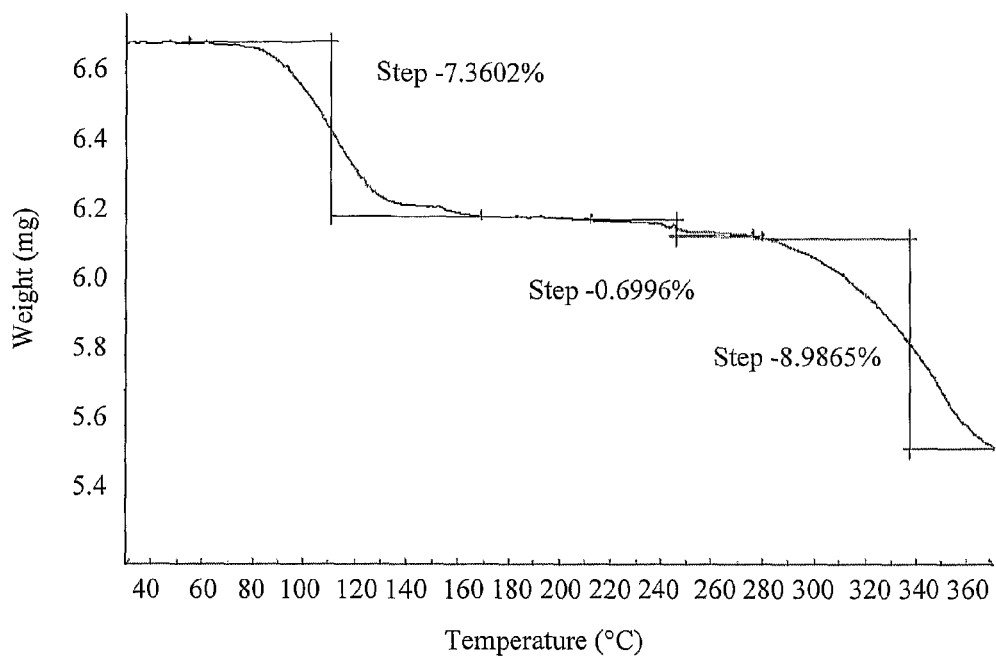
FIG. 23 illustrates a characteristic Thermogravimetric analysis (TGA) profile of crystalline Form V of deferasirox (hemi-DMSO solvate).
Figure 24:
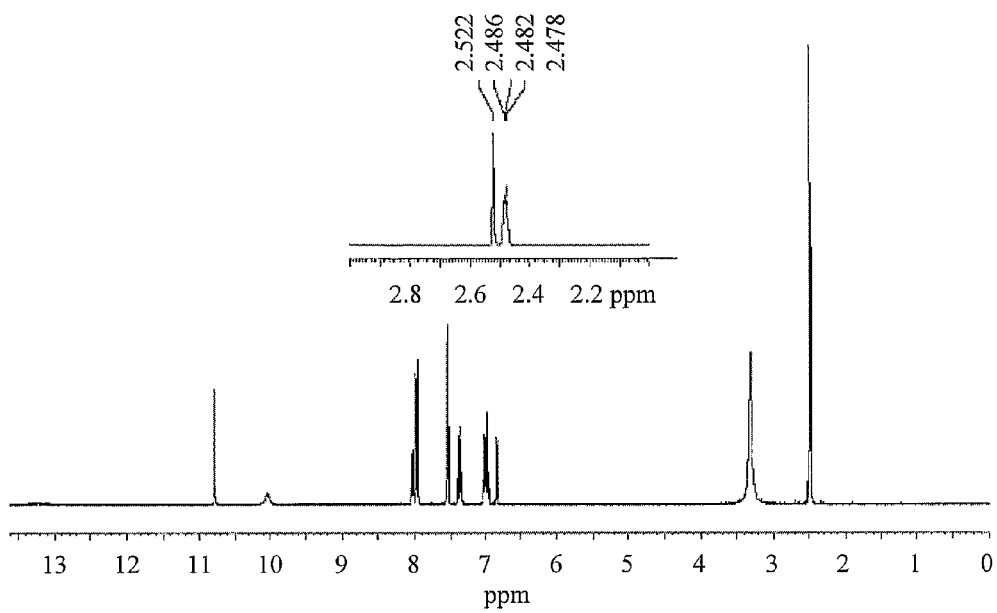
FIG. 24 illustrates a characteristic Nuclear Magnetic Resonance (NMR) profile of crystalline Form V of deferasirox (hemi-DMSO solvate).

In other embodiments, the crystalline deferasirox hemi-DMSO solvate (Form V) is characterized by an X-ray powder diffraction pattern substantially as shown in FIG. 21. In one embodiment, the crystalline deferasirox hemi-DMSO solvate is further characterized by a DSC profile having endothermic peaks at about 89° C. and about 260° C. In another embodiment, the crystalline deferasirox hemi-DMSO solvate is further characterized by a DSC profile substantially as shown in FIG. 22. In another embodiment, the crystalline deferasirox hemi-DMSO solvate is further characterized by a TGA profile substantially as shown in FIG. 23. In another embodiment, the crystalline deferasirox hemi-DMSO solvate is further characterized by NMR spectrum substantially as shown in FIG. 24.

The crystalline deferasirox hemi-DMSO solvate (Form V) converted to Form I after being dried at 120° C. for 1 hr with vacuum. The XRPD and DSC profiles of Form V before and after drying at 120° C. for 1 hr are set forth in FIGS. 25 and 26, respectively. Also shown in FIGS. 25 and 26 for comparison are the X-ray diffraction pattern and DSC profile of deferasirox Form I ("DFX-API"), respectively.

In one embodiment, the crystalline deferasirox hemi-DMSO solvate (Form V) may be prepared by a process comprising the steps of (a) dissolving deferasirox, preferably deferasirox Form I in a solvent mixture selected from DMSO:DMF and DMSO:THF, wherein the dissolving step is preferably conducted under heat; and (b) evaporating the solvent to precipitate deferasirox Form V. In a currently preferred embodiment, the ratio of DMSO to DMF or DMSO to THF is about 1:1 v/v. Preferably, the solvent evaporation step is conducted at a temperature of about 50° C. to about 60° C. The solution of deferasirox in DMSO:DMF or DMSO:THF can be filtered prior to the solvent evaporation step.

Deferasirox Form VI:

According to another aspect, the present invention provides a crystalline deferasirox mono-DMF solvate (Form VI). The crystalline deferasirox Form VI contains approximately 10% DMF as indicated by TGA and NMR. The crystalline deferasirox Form VI is a mono-DMF solvate, i.e., it contains approximately 1 molecule of DMF to 1 molecule of deferasirox.

In one embodiment, the crystalline deferasirox mono-DMF solvate (Form VI) is characterized by an X-ray powder diffraction pattern with diffraction peaks at 2-theta values of about 9.9±0.1 and 16.6±0.1. In another embodiment, the crystalline deferasirox mono-DMF solvate (Form VI) is characterized by an X-ray powder diffraction pattern with diffraction peaks at 2-theta values of about 9.9±0.1, 10.6±0.1, 16.6±0.1 and 20.0±0.1. In another embodiment, the present invention provides a crystalline deferasirox mono-DMF solvate (Form VI) is characterized by at least 3 X-ray diffraction peaks selected from about 5.3±0.1, 9.9±0.1, 10.3±0.1, 10.6±0.1, 16.0±0.1, 16.6±0.1, 18.8±0.1, 20.0±0.1, 20.7±0.1, 21.4±0.1, 22.7±0.1, 24.0±0.1, 25.7±0.1, 26.8±0.1, 30.1±0.1, 32.3±0.1, 33.6±0.1 and 33.9±0.1 degrees 2-theta. In particular embodiments, the crystalline deferasirox mono-DMF solvate (Form VI) is characterized by an X-ray powder diffraction pattern with diffraction peaks at 2-theta values of about 5.3±0.1, 9.9±0.1, 10.3±0.1, 10.6±0.1, 16.0±0.1, 16.6±0.1, 18.8±0.1, 20.0±0.1, 20.7±0.1, 21.4±0.1, 22.7±0.1, 24.0±0.1, 25.7±0.1, 26.8±0.1, 30.1±0.1, 32.3±0.1, 33.6±0.1 and 33.9±0.1.

In particular embodiments, the present invention provides a crystalline deferasirox mono-DMF solvate (Form VI) having an X-ray powder diffraction pattern characterized by diffraction peaks as set forth in Table 3:

TABLE 3

| 2-theta | d-spacing | BG | Height | H % | Area | A % | FWHM | XS | P/N |
|---|---|---|---|---|---|---|---|---|---|
| 5.305 | 16.6455 | 43 | 281 | 6.0 | 33.9 | 4.4 | 0.121 | 2093 | 7.1 |
| 9.940 | 8.8915 | 33 | 4695 | 100.0 | 779.2 | 100.0 | 0.142 | 1215 | 34.0 |
| 10.298 | 8.5831 | 34 | 389 | 8.3 | 110.8 | 14.2 | 0.265 | 389 | 9.0 |
| 10.601 | 8.3385 | 34 | 1755 | 37.4 | 247.0 | 31.7 | 0.122 | 2045 | 20.5 |
| 15.957 | 5.5495 | 46 | 1709 | 36.4 | 306.1 | 39.3 | 0.156 | 963 | 20.1 |
| 16.621 | 5.3293 | 48 | 2823 | 60.1 | 538.1 | 69.1 | 0.165 | 860 | 26.1 |
| 18.840 | 4.7065 | 64 | 357 | 7.6 | 47.7 | 6.1 | 0.138 | 1321 | 7.8 |
| 19.958 | 4.4451 | 62 | 1934 | 41.2 | 358.6 | 46.0 | 0.163 | 887 | 21.3 |
| 20.678 | 4.2920 | 57 | 175 | 3.7 | 40.7 | 5.2 | 0.292 | 344 | 4.5 |
| 21.357 | 4.1570 | 64 | 511 | 10.9 | 263.1 | 33.8 | 0.500 | 179 | 9.9 |
| 22.677 | 3.9180 | 65 | 1051 | 22.4 | 198.2 | 25.4 | 0.171 | 805 | 15.2 |
| 23.961 | 3.7109 | 63 | 132 | 2.8 | 33.7 | 4.3 | 0.414 | 224 | 3.0 |
| 25.659 | 3.4690 | 58 | 296 | 6.3 | 99.8 | 12.8 | 0.357 | 269 | 6.9 |
| 26.761 | 3.3286 | 61 | 220 | 4.7 | 54.6 | 7.0 | 0.293 | 346 | 5.3 |
| 30.140 | 2.9627 | 53 | 177 | 3.8 | 41.9 | 5.4 | 0.289 | 356 | 4.6 |
| 32.262 | 2.7725 | 50 | 323 | 6.9 | 70.5 | 9.1 | 0.220 | 528 | 7.6 |
| 33.639 | 2.6621 | 50 | 144 | 3.1 | 70.2 | 9.0 | 0.635 | 141 | 3.9 |
| 33.860 | 2.6452 | 48 | 177 | 3.8 | 72.8 | 9.3 | 0.482 | 192 | 4.8 |

Figure 27:
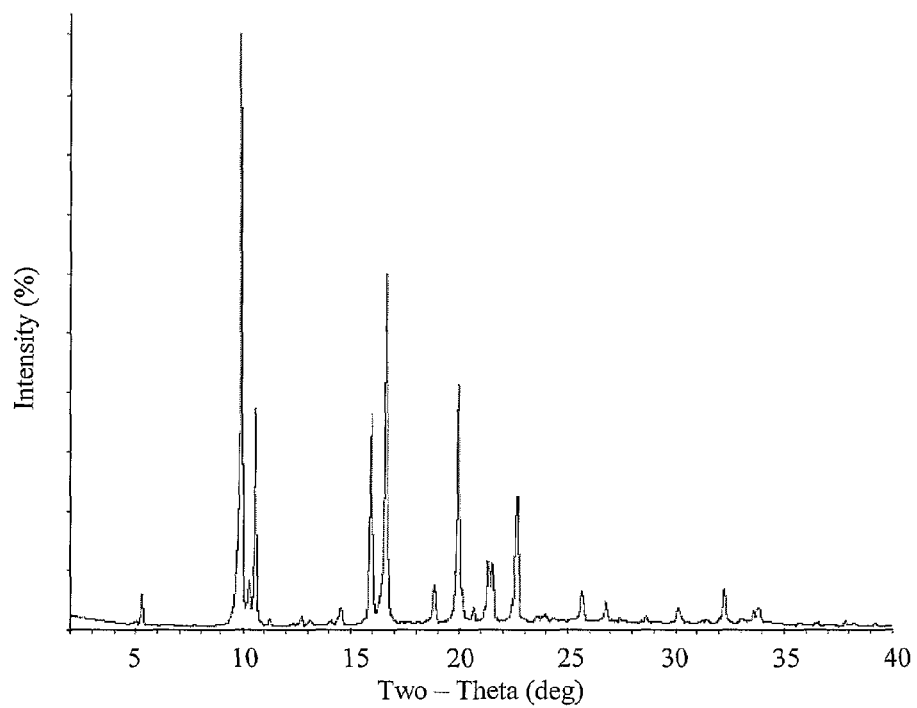
FIG. 27 illustrates a characteristic X-ray diffraction pattern of crystalline Form VI of deferasirox (mono-DMF solvate).
Figure 28:
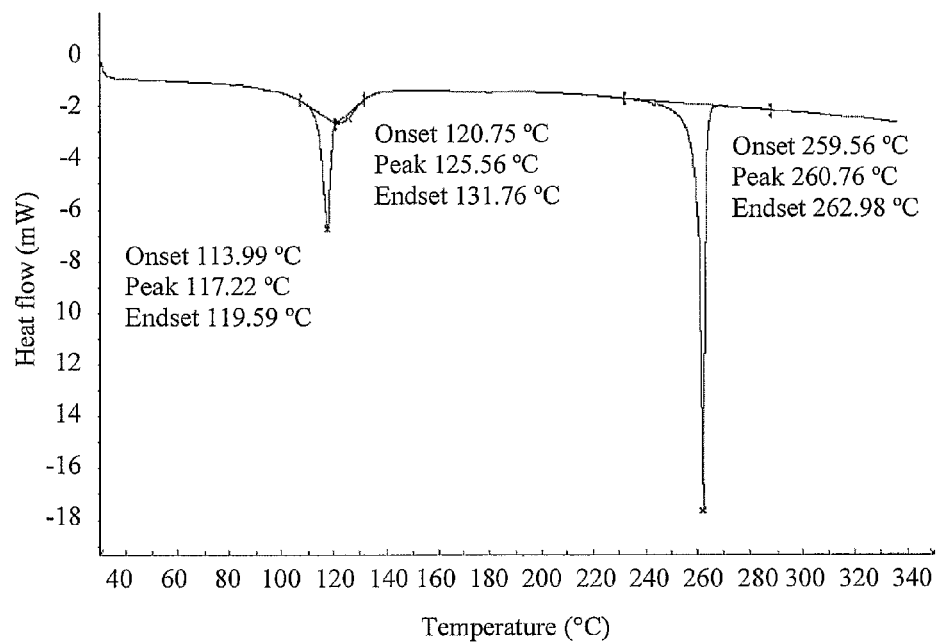
FIG. 28 illustrates a characteristic Differential Scanning calorimetry (DSC) profile of crystalline Form VI of deferasirox (mono-DMF solvate).
Figure 29:
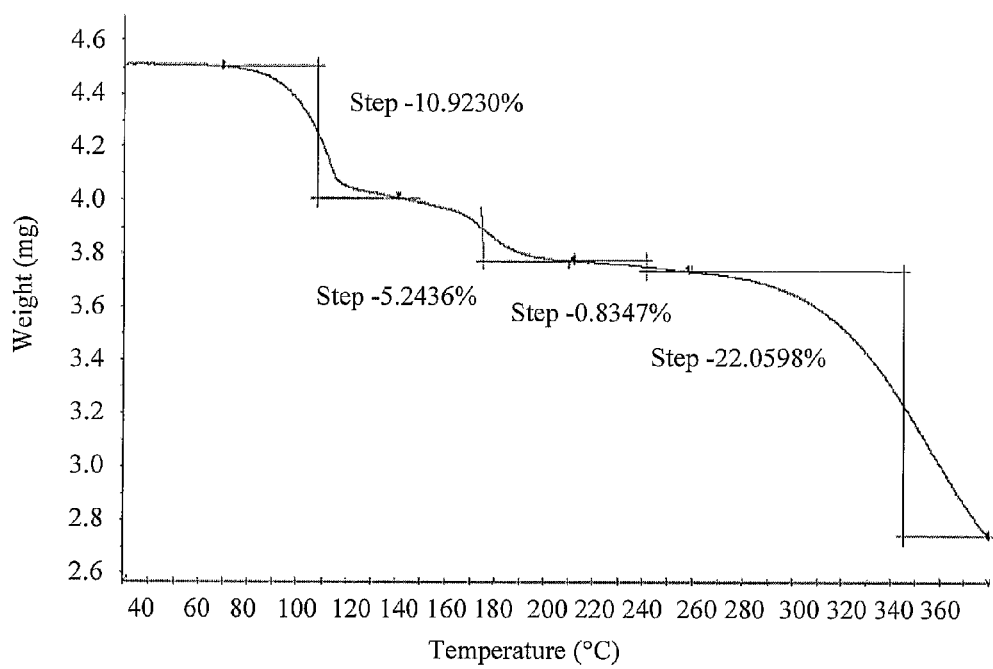
FIG. 29 illustrates a characteristic Thermogravimetric analysis (TGA) profile of crystalline Form VI of deferasirox (mono-DMF solvate).
Figure 30:
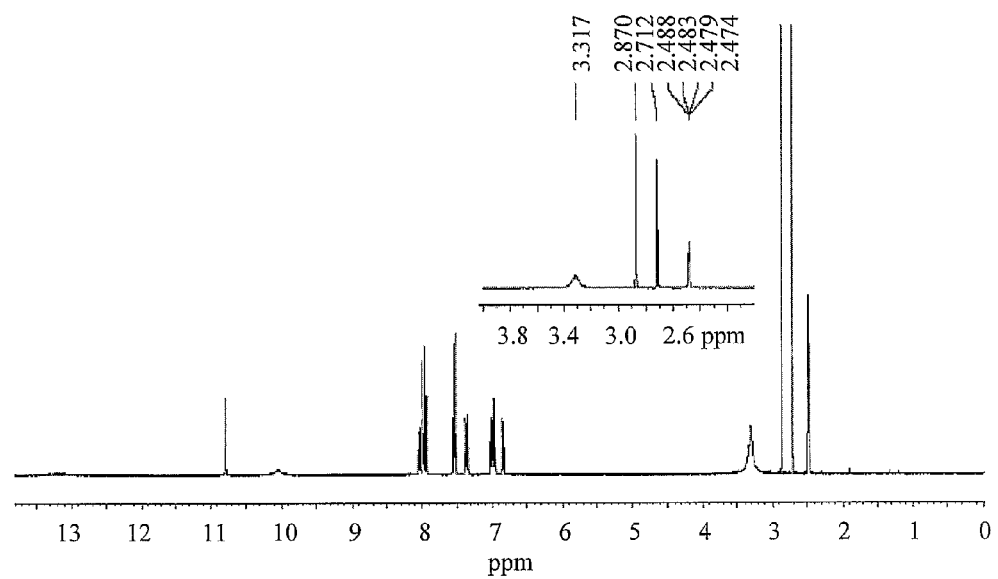
FIG. 30 illustrates a characteristic Nuclear Magnetic Resonance (NMR) profile of crystalline Form VI of deferasirox (mono-DMF solvate).

Scan: 2.0/40.0/0.02/0.12(sec), Cu (40 kV, 40 mA), I(max) = 4695
Peak: 19(pts)/Parabolic Filter, Threshold = 4.0, Cutoff = 3.0%, BG = 3/3.0, Peak-Top = Summit In other embodiments, the crystalline deferasirox mono-DMF solvate (Form VI) is characterized by an X-ray powder diffraction pattern substantially as shown in FIG. 27. In one embodiment, the crystalline deferasirox mono-DMF solvate is further characterized by a DSC profile having endothermic peaks at about 117° C., about 125° C. and about 260° C. In another embodiment, the crystalline deferasirox mono-DMF solvate is further characterized by a DSC profile substantially as shown in FIG. 28. In another embodiment, the crystalline deferasirox mono-DMF solvate is further characterized by a TGA profile substantially as shown in FIG. 29. In another embodiment, the crystalline deferasirox mono-DMF solvate is further characterized by NMR spectrum substantially as shown in FIG. 30.

The crystalline deferasirox mono-DMF solvate (Form VI) converted to Form I after being dried at 120° C. for 1 hr with vacuum. The XRPD and DSC profiles of Form VI before and after drying at 120° C. for 1 hr are set forth in FIGS. 31 and 32, respectively. Also shown in FIGS. 31 and 32 for comparison are the X-ray diffraction pattern and DSC profile of deferasirox Form I ("DFX-API"), respectively.

In one embodiment, the crystalline deferasirox mono-DMF solvate (Form VI) may be prepared by a process comprising the steps of: (a) providing a suspension of deferasirox, preferably deferasirox Form I in a solvent mixture comprising 2-methyl THF:DMF; (b) stirring the suspension; and (c) filtering to provide deferasirox Form VI. In a currently preferred embodiment, the ratio of 2-methyl THF to DMF is about 3:1 v/v. The suspension can be stirred for a variable duration, for example from 1 to 48 hours, more preferably from 12 to 24 hours, and even more preferably for about 24 hours. After the filtering step, the filter cake can be dried at room temperature or with heating for a sufficient period to time, for example 1 to 24 hours, e.g., overnight.

Figure 33:
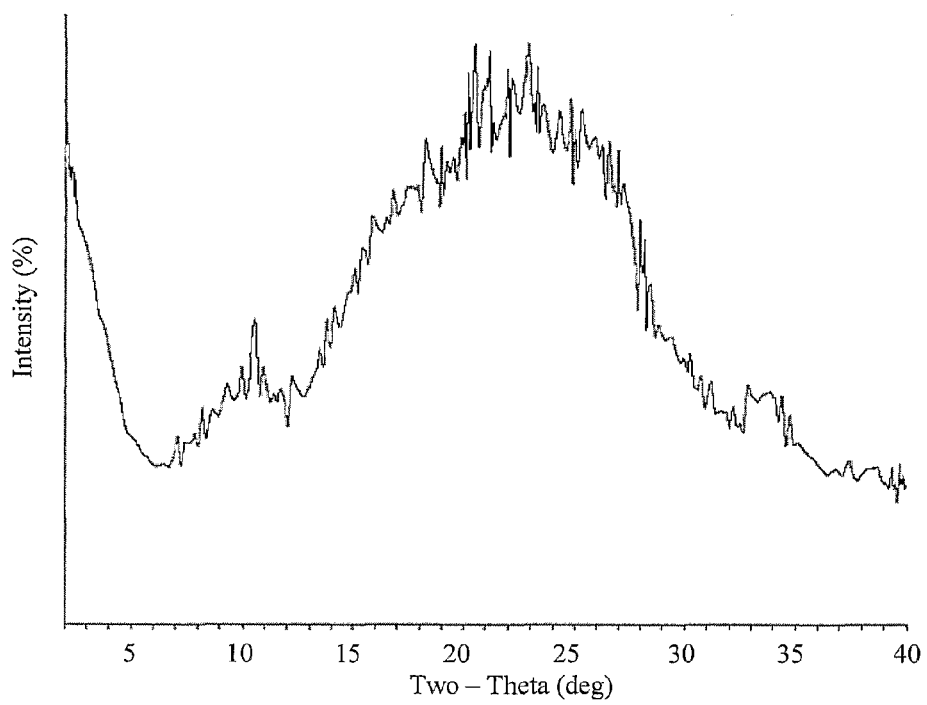
FIG. 33 illustrates a characteristic X-ray diffraction pattern of amorphous deferasirox.
Figure 34:
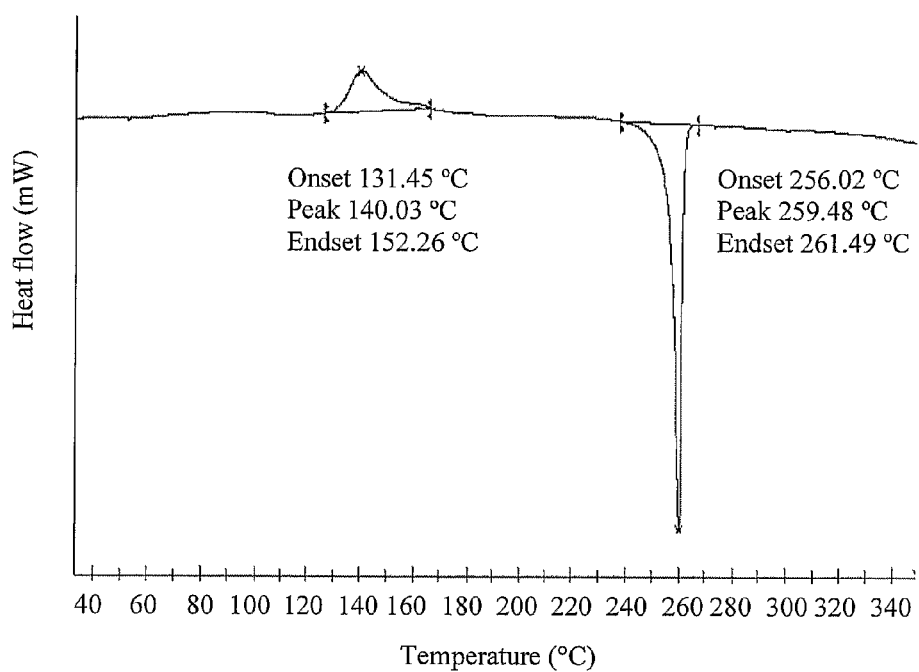
FIG. 34 illustrates a characteristic Differential Scanning calorimetry (DSC) profile of amorphous deferasirox.
Figure 35:
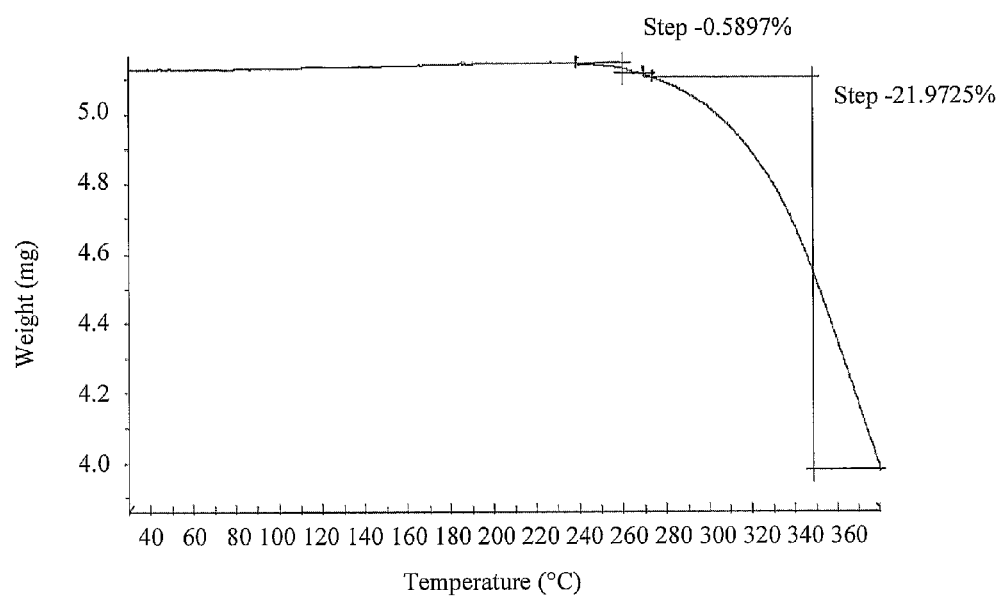
FIG. 35 illustrates a characteristic Thermogravimetric analysis (TGA) profile of amorphous deferasirox.

Amorphous Deferasirox:

According to another aspect, the present invention provides an amorphous deferasirox, which is characterized by a DSC profile having an exothermic peak at about 140° C. and an endothermic peak at about 260° C. In certain embodiments, the amorphous form of deferasirox is further characterized by an X-ray powder diffraction pattern substantially as shown in FIG. 33. In other embodiments, the amorphous form of deferasirox is further characterized by a DSC profile substantially as shown in FIG. 34. In other embodiments, the amorphous form of deferasirox is further characterized by a TGA profile substantially as shown in FIG. 35.

The amorphous deferasirox may be prepared by a process comprising the steps of: (a) heating a deferasirox, preferably deferasirox Form I to melt; and (b) rapidly cooling the melted deferasirox obtained in step (a), so as to provide amorphous deferasirox. Preferably, the heating step is conducted under vacuum and the precipitation method is controlled by rapid cooling.

The amorphous deferasirox converted to Form I after being heated to 160° C. for 5 minutes. This indicated that the exothermic peak in the DSC profile was due to the transformation of the amorphous form to Form I and the endothermic peak was the melting event of Form I. The XRPD and DSC profiles of amorphous deferasirox before and after drying at 160° C. are set forth in FIGS. 36 and 37, respectively. Also shown in FIGS. 36 and 37 for comparison are the X-ray diffraction pattern and DSC profile of deferasirox Form I ("DFX-API"), respectively.

Deferasirox Form III:

The present invention further provides processes for preparing a crystalline deferasirox hemi-DMF solvate (Form III). The crystalline deferasirox Form III contains approximately 12% DMF as indicated by TGA and NMR. The crystalline deferasirox Form III is a hemi-DMF solvate, i.e., it contains approximately 0.5 molecule of DMF to 1 molecule of deferasirox. The hemi-DMF solvate (Form III) is also encompassed by the present invention.

In one embodiment, the deferasirox hemi-DMF solvate (Form III) is characterized by an X-ray powder diffraction pattern with diffraction peaks at 2-theta values of about 9.8±0.1 and 16.5±0.1. In another embodiment, the crystalline deferasirox hemi-DMF solvate (Form III) is further characterized by diffraction peaks at 2-theta values of about 22.4±0.1 and 23.8±0.1. In another embodiment, the crystalline deferasirox hemi-DMF solvate (Form III) is characterized by an X-ray powder diffraction pattern with at least 3 diffraction peaks at 2-theta values of about 2.9±0.1, 9.1±0.1, 9.8±0.1, 10.1±0.1, 10.5±0.1, 11.6±0.1, 12.5±0.1, 14.4±0.1, 14.8±0.1, 15.4±0.1, 15.8±0.1, 16.5±0.1, 17.5±0.1, 18.0±0.1, 18.7±0.1, 19.8±0.1, 20.5±0.1, 21.4±0.1, 22.4±0.1, 23.1±0.1, 23.8±0.1, 24.3±0.1, 25.0±0.1, 25.6±0.1, 26.6±0.1, 28.0±0.1, 31.1±0.1, 32.1±0.1, 33.51, 36.0±0.1, and 36.8±0.1. In another embodiment, the crystalline deferasirox hemi-DMF solvate (Form III) is characterized by an X-ray powder diffraction pattern with diffraction peaks at 2-theta values of about 2.9±0.1, 9.1±0.1, 9.8±0.1, 10.1±0.1, 10.5±0.1, 11.6±0.1, 12.5±0.1, 14.4±0.1, 14.8±0.1, 15.4±0.1, 15.8±0.1, 16.5±0.1, 17.5±0.1, 18.0±0.1, 18.7±0.1, 19.8±0.1, 20.5±0.1, 21.4±0.1, 22.4±0.1, 23.1±0.1, 23.8±0.1, 24.3±0.1, 25.0±0.1, 25.6±0.1, 26.6±0.1, 28.0±0.1, 31.1±0.1, 32.1±0.1, 33.5±, 36.0±0.1, and 36.8e0.1.

In particular embodiments, the crystalline deferasirox hemi-DMF solvate (Form III) is characterized by an X-ray powder diffraction pattern having diffraction peaks as set forth in Table 4:

TABLE 4

| 2-theta | d-spacing | BG | Height | H % | Area | A % | FWHM | XS | P/N |
|---|---|---|---|---|---|---|---|---|---|
| 2.920 | 30.2344 | 40 | 122 | 10.7 | 109.6 | 38.6 | 1.135 | 72 | 3.7 |
| 9.079 | 9.7330 | 35 | 130 | 11.5 | 24.7 | 8.7 | 0.221 | 506 | 4.2 |
| 9.800 | 9.0178 | 36 | 1136 | 100.0 | 266.9 | 93.9 | 0.206 | 566 | 16.3 |
| 10.160 | 8.6996 | 36 | 145 | 12.8 | 44.5 | 15.7 | 0.346 | 274 | 4.5 |
| 10.500 | 8.4182 | 36 | 300 | 26.4 | 50.1 | 17.6 | 0.162 | 891 | 7.6 |
| 11.640 | 7.5964 | 36 | 112 | 9.9 | 10.5 | 3.7 | 0.117 | 2516 | 3.6 |
| 12.520 | 7.0641 | 36 | 161 | 14.2 | 28.7 | 10.1 | 0.197 | 614 | 4.9 |
| 14.440 | 6.1291 | 45 | 154 | 13.5 | 31.0 | 10.9 | 0.242 | 444 | 4.4 |
| 14.757 | 5.9981 | 46 | 92 | 8.1 | 9.8 | 3.5 | 0.185 | 687 | 2.4 |
| 15.440 | 5.7343 | 44 | 90 | 7.9 | 29.8 | 10.5 | 0.556 | 157 | 2.4 |
| 15.821 | 5.5969 | 45 | 390 | 34.3 | 93.4 | 32.9 | 0.230 | 478 | 8.7 |
| 16.519 | 5.3620 | 47 | 1130 | 99.5 | 284.2 | 100.0 | 0.223 | 503 | 16.1 |
| 17.479 | 5.0696 | 50 | 423 | 37.3 | 120.1 | 42.3 | 0.273 | 375 | 9.1 |
| 17.979 | 4.9297 | 50 | 130 | 11.4 | 33.5 | 11.8 | 0.354 | 268 | 3.5 |
| 18.720 | 4.7362 | 53 | 140 | 12.3 | 25.8 | 9.1 | 0.253 | 418 | 3.7 |
| 19.801 | 4.4801 | 54 | 288 | 25.3 | 81.5 | 28.7 | 0.296 | 337 | 6.9 |
| 20.539 | 4.3207 | 56 | 321 | 28.3 | 79.4 | 27.9 | 0.255 | 414 | 7.4 |
| 21.398 | 4.1492 | 60 | 183 | 16.1 | 45.7 | 16.1 | 0.315 | 312 | 4.6 |
| 22.380 | 3.9694 | 72 | 816 | 71.8 | 221.6 | 78.0 | 0.253 | 420 | 13.0 |
| 23.077 | 3.8509 | 82 | 133 | 11.7 | 16.1 | 5.7 | 0.268 | 388 | 2.2 |
| 23.819 | 3.7326 | 67 | 676 | 59.5 | 181.8 | 64.0 | 0.254 | 420 | 11.7 |
| 24.299 | 3.6600 | 66 | 511 | 45.0 | 157.0 | 55.2 | 0.300 | 335 | 9.8 |
| 24.980 | 3.5617 | 76 | 167 | 14.7 | 42.7 | 15.0 | 0.401 | 233 | 3.5 |
| 25.561 | 3.4821 | 74 | 173 | 15.2 | 55.6 | 19.6 | 0.481 | 189 | 3.7 |
| 26.599 | 3.3485 | 74 | 158 | 13.9 | 57.9 | 20.4 | 0.587 | 151 | 3.3 |
| 28.039 | 3.1797 | 59 | 102 | 9.0 | 28.9 | 10.2 | 0.574 | 155 | 2.1 |
| 31.080 | 2.8752 | 48 | 86 | 7.6 | 44.6 | 15.7 | 0.998 | 86 | 2.1 |
| 32.118 | 2.7846 | 48 | 136 | 12.0 | 77.7 | 27.3 | 0.756 | 116 | 3.7 |
| 33.479 | 2.6744 | 46 | 181 | 15.9 | 73.2 | 25.7 | 0.462 | 201 | 5.0 |
| 36.020 | 2.4914 | 39 | 73 | 6.5 | 35.7 | 12.6 | 0.873 | 100 | 2.0 |
| 36.840 | 2.4378 | 37 | 74 | 6.5 | 35.7 | 12.6 | 0.817 | 108 | 2.2 |

Figure 9:
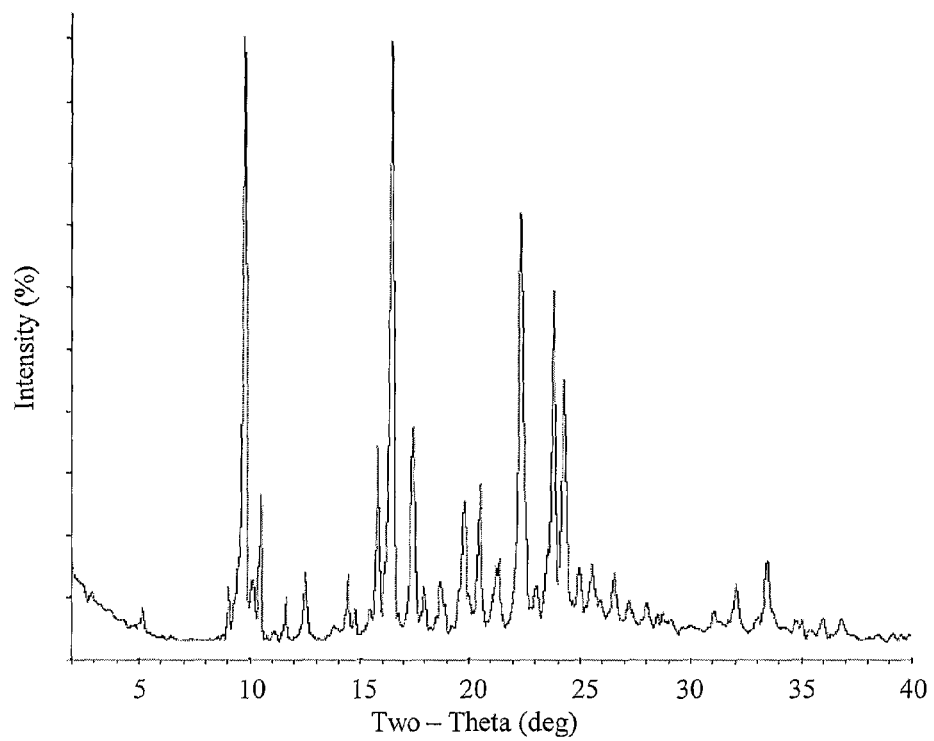
FIG. 9 illustrates a characteristic X-ray diffraction pattern of crystalline Form III of deferasirox (hemi-DMF solvate).

Scan: 2.0/40.0/0.02/0.12(sec), Cu (40 kV, 40 mA), I(max) = 1136
Peak: 21(pts)/Parabolic Filter, Threshold = 4.0, Cutoff = 3.0%, BG = 3/3.0, Peak-Top = Summit In another embodiment, the crystalline deferasirox hemi-DMF solvate is characterized by an X-ray powder diffraction pattern substantially as shown in FIG. 9. In another embodiment, the crystalline deferasirox hemi-DMF solvate is characterized by a DSC profile substantially as set forth in FIG. 10. In another embodiment, the crystalline deferasirox hemi-DMF solvate is characterized by a DSC profile having endothermic peaks at about 114° C. and about 260° C. In another embodiment, the crystalline deferasirox hemi-DMF solvate is characterized by a TGA profile substantially as set forth in FIG. 11. In another embodiment, the crystalline deferasirox hemi-DMF solvate is characterized by a NMR spectrum substantially as set forth in FIG. 12.

The crystalline deferasirox hemi-DMF solvate (Form III) converted to Form I after being dried at 120° C. for 1 hr. The XRPD and DSC profiles of Form III before and after drying at 120° C. for 1 hr are set forth in FIGS. 13 and 14 respectively. Also shown for comparison is the X-ray diffraction pattern of deferasirox Form I.

The crystalline deferasirox hemi-DMF solvate (Form III) may be prepared by a process comprising the steps of: (a) providing a suspension of deferasirox, preferably deferasirox Form I in DMF; (b) stirring the suspension; and (c) filtering to provide deferasirox Form III. The suspension can be stirred for a variable duration, for example from 1 to 48 hours, more preferably from 12 to 24 hours, and even more preferably for about 24 hours. After the filtering step, the filter cake can be dried at room temperature or heated for a sufficient period to time, for example 1 to 24 hours, e.g., overnight.

Alternatively, the crystalline deferasirox hemi-DMF solvate (Form III) may be prepared by a process comprising the steps of (a) dissolving deferasirox, preferably deferasirox Form I in a solvent mixture selected from DMF:1,4-Dioxane, DMF:THF, DMF:EtOH and DMF: EtOAc, wherein the dissolving step is preferably conducted under heat; and (b) evaporating the solvent to precipitate deferasirox Form III. In a currently preferred embodiment, the ratio of DMF to 1,4-dioxane, THF, EtOH or EtOAc is about 1:1 v/v. Preferably, the solvent evaporation step is conducted at a temperature of about 50° C. to about 60° C. The solution of deferasirox in DMF:1,4-Dioxane, DMF:THF, DMF:EtOH or DMF:EtOAc can be filtered prior to the solvent evaporation step.

Deferasirox Form IV:

The present invention further provides processes for preparing a crystalline deferasirox mono-THF solvate (Form IV). The crystalline deferasirox Form IV contains approximately 16% DMSO as indicated by TGA and NMR. The crystalline deferasirox Form IV is a mono-THF solvate, i.e., it contains approximately 1 molecule of THF to 1 molecule of deferasirox. The mono-THF solvate (Form IV) is also encompassed by the present invention.

In one embodiment, the crystalline deferasirox mono-THF solvate (Form IV), which is characterized by an X-ray powder diffraction pattern with diffraction peaks at 2-theta values of about 19.8±0.1 and 24.2±0.1. In another embodiment, the deferasirox mono-THF solvate is further characterized diffraction peaks at 2-theta values of about 15.2±0.1 and 20.1±0.1. In another embodiment, the crystalline deferasirox mono-THF solvate (Form IV) is characterized by an X-ray powder diffraction pattern with at least 3 diffraction peaks at 2-theta values of about 6.8±0.1, 10.0±0.1, 10.6±0.1, 11.8±0.1, 13.5±0.1, 15.2±0.1, 16.6±0.1, 19.2±0.1, 19.8±0.1, 20.1±0.1, 20.8±0.1, 21.9±0.1, 22.4±0.1, 24.2±0.1, 24.7±0.1, 25.6±0.1, 26.0±0.1, 27.4±0.1, 29.4±0.1, 31.1±0.1, 34.4±0.1, 37.6±0.1, 38.4±0.1 and 38.8±0.1. In another embodiment, the crystalline deferasirox mono-THF solvate (Form IV) is characterized by an X-ray powder diffraction pattern with diffraction peaks at 2-theta values of about 6.8±0.1, 10.0±0.1, 10.6±0.1, 11.8±0.1, 13.5±0.1, 15.2±0.1, 16.6±0.1, 17.7±0.1, 19.2±0.1, 19.8±0.1, 20.1±0.1, 20.8±0.1, 21.9±0.1, 22.4±0.1, 24.2±0.1, 24.7±0.1, 25.6±0.1, 26.0±0.1, 27.4±0.1, 28.3±0.1, 29.4±0.1, 31.1±0.1, 34.4±0.1, 37.6±0.1, 38.4±0.1 and 38.8±0.1.

In particular embodiments, the crystalline deferasirox mono-THF solvate (Form VI) is characterized by an X-ray powder diffraction pattern having diffraction peaks as set forth in Table 5:

TABLE 5

| 2-theta | d-spacing | BG | Height | H % | Area | A % | FWHM | XS | P/N |
|---|---|---|---|---|---|---|---|---|---|
| 6.759 | 13.0677 | 27 | 293 | 49.0 | 68.7 | 17.3 | 0.220 | 510 | 7.8 |
| 9.980 | 8.8560 | 20 | 58 | 9.7 | 23.5 | 5.9 | 0.528 | 166 | 2.5 |
| 10.580 | 8.3550 | 20 | 49 | 8.2 | 23.5 | 5.9 | 0.696 | 122 | 2.1 |
| 11.801 | 7.4930 | 21 | 126 | 21.1 | 35.0 | 8.8 | 0.285 | 352 | 4.7 |
| 13.460 | 6.5729 | 25 | 136 | 22.8 | 41.3 | 10.4 | 0.316 | 307 | 4.8 |
| 15.159 | 5.8398 | 29 | 317 | 53.1 | 93.7 | 23.5 | 0.277 | 367 | 8.1 |
| 16.580 | 5.3424 | 33 | 77 | 12.9 | 19.1 | 4.8 | 0.373 | 251 | 2.5 |
| 17.680 | 5.0126 | 41 | 296 | 49.6 | 99.2 | 24.9 | 0.330 | 293 | 7.4 |
| 19.161 | 4.6283 | 59 | 94 | 15.7 | 16.3 | 4.1 | 0.405 | 228 | 1.8 |
| 19.800 | 4.4804 | 51 | 398 | 66.7 | 229.9 | 57.7 | 0.562 | 157 | 8.7 |
| 20.056 | 4.4236 | 51 | 319 | 53.4 | 398.2 | 100.0 | 1.267 | 66 | 7.5 |
| 20.820 | 4.2631 | 56 | 282 | 47.2 | 77.2 | 19.4 | 0.291 | 347 | 6.7 |
| 21.920 | 4.0516 | 62 | 126 | 21.2 | 29.1 | 7.3 | 0.383 | 245 | 2.9 |
| 22.420 | 3.9623 | 67 | 235 | 39.4 | 64.3 | 16.1 | 0.325 | 301 | 5.5 |
| 24.181 | 3.6776 | 77 | 597 | 100.0 | 228.6 | 57.4 | 0.374 | 253 | 10.6 |
| 24.699 | 3.6016 | 74 | 166 | 27.8 | 58.7 | 14.7 | 0.543 | 164 | 3.6 |
| 25.560 | 3.4823 | 81 | 179 | 30.0 | 42.2 | 10.6 | 0.363 | 263 | 3.7 |
| 26.040 | 3.4191 | 79 | 236 | 39.4 | 113.9 | 28.6 | 0.617 | 143 | 5.1 |
| 27.399 | 3.2525 | 70 | 180 | 30.2 | 38.8 | 9.7 | 0.299 | 338 | 4.1 |
| 28.340 | 3.1466 | 65 | 160 | 26.7 | 46.5 | 11.7 | 0.418 | 223 | 3.7 |
| 29.400 | 3.0356 | 56 | 194 | 32.5 | 67.6 | 17.0 | 0.417 | 225 | 4.9 |
| 31.079 | 2.8753 | 50 | 141 | 23.7 | 32.3 | 8.1 | 0.300 | 340 | 3.9 |
| 34.404 | 2.6047 | 48 | 74 | 12.3 | 46.1 | 11.6 | 1.512 | 56 | 1.5 |
| 37.639 | 2.3879 | 39 | 63 | 10.6 | 27.7 | 7.0 | 0.961 | 91 | 1.5 |
| 38.439 | 2.3400 | 36 | 69 | 11.6 | 39.1 | 9.8 | 1.006 | 87 | 2.0 |
| 38.760 | 2.3213 | 35 | 65 | 10.9 | 39.1 | 9.8 | 1.126 | 77 | 1.8 |

Figure 15:
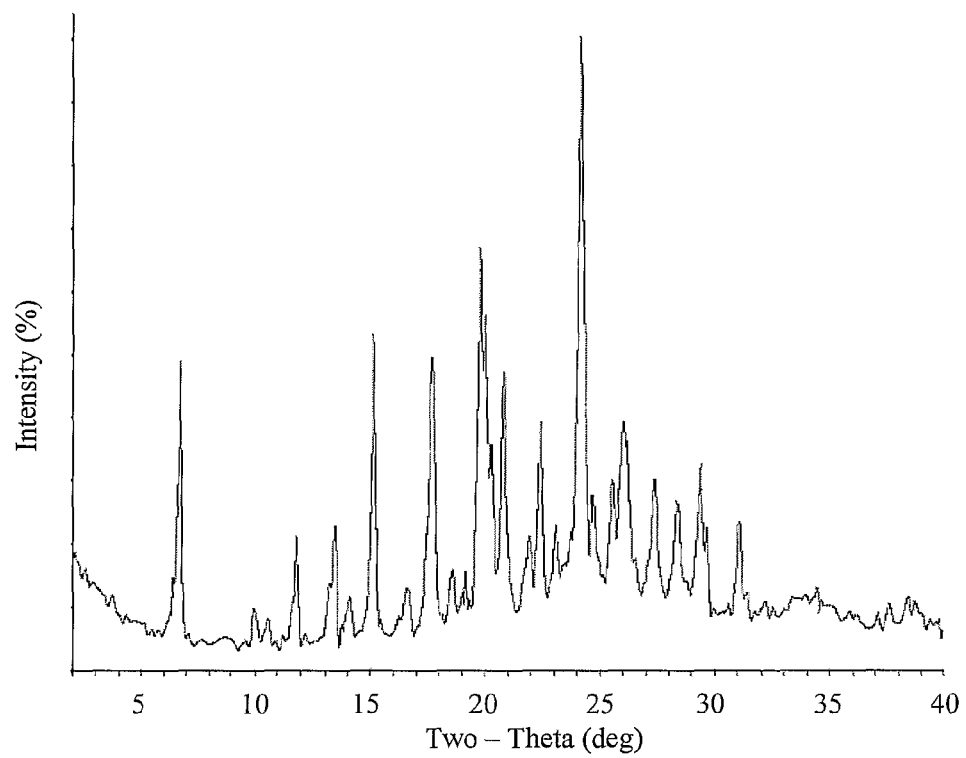
FIG. 15 illustrates a characteristic X-ray diffraction pattern of crystalline Form IV of deferasirox (mono-THF solvate).

Scan: 2.0/40.0/0.02/0.12(sec), Cu (40 kV, 40 mA), I(max) = 597
Peak: 27(pts)/Parabolic Filter, Threshold = 2.0, Cutoff = 4.0%, BG = 1/2.0, Peak-Top = Summit In another embodiment, the crystalline deferasirox mono-THF solvate is characterized by an X-ray powder diffraction pattern substantially as shown in FIG. 15. In another embodiment, the crystalline deferasirox mono-THF solvate is characterized by a DSC profile substantially as set forth in FIG. 16. In another embodiment, the crystalline deferasirox mono-THF solvate is characterized by a DSC profile having endothermic peaks at about 97° C. and about 260° C. In another embodiment, the crystalline deferasirox mono-THF solvate is characterized by a TGA profile substantially as set forth in FIG. 17. In another embodiment, the crystalline deferasirox mono-THF solvate is characterized by a NMR spectrum substantially as set forth in FIG. 18.

The crystalline deferasirox mono-THF solvate (Form IV) converted to Form I after being dried at 120° C. for 1 hr. The XRPD and DSC profiles of Form IV before and after drying at 120° C. for 1 hr are set forth in FIGS. 19 and 20, respectively. Also shown in FIGS. 19 and 20 for comparison are the X-ray diffraction pattern and DSC profile of deferasirox Form I, respectively.

The crystalline deferasirox mono-THF solvate (Form IV) may be prepared by a process comprising the steps of (a) providing a suspension of deferasirox, preferably deferasirox Form I in THF; (b) stirring the suspension; and (c) filtering to provide deferasirox Form IV. The suspension can be stirred for a variable duration, for example from 1 to 48 hours, more preferably from 12 to 24 hours, and even more preferably for about 24 hours. After the filtering step, the filter cake can be dried at room temperature or heated for a sufficient period to time, for example 1 to 24 hours, e.g., overnight.

Alternatively, the crystalline deferasirox mono-THF solvate (Form IV) may be prepared by a process comprising the steps of (a) dissolving deferasirox, preferably deferasirox Form I in a solvent mixture selected from THF:MEK and THF:acetone, wherein the dissolving step is preferably conducted under heat; and (b) evaporating the solvent to precipitate deferasirox Form IV. In a currently preferred embodiment, the ratio of THF to MEK or THF to acetone is about 1:1 v/v. Preferably, the solvent evaporation step is conducted at a temperature of about 50° C. to about 60° C. The solution of deferasirox in THF:MEK or THF:acetone can be filtered prior to the solvent evaporation step.

Figure 2:
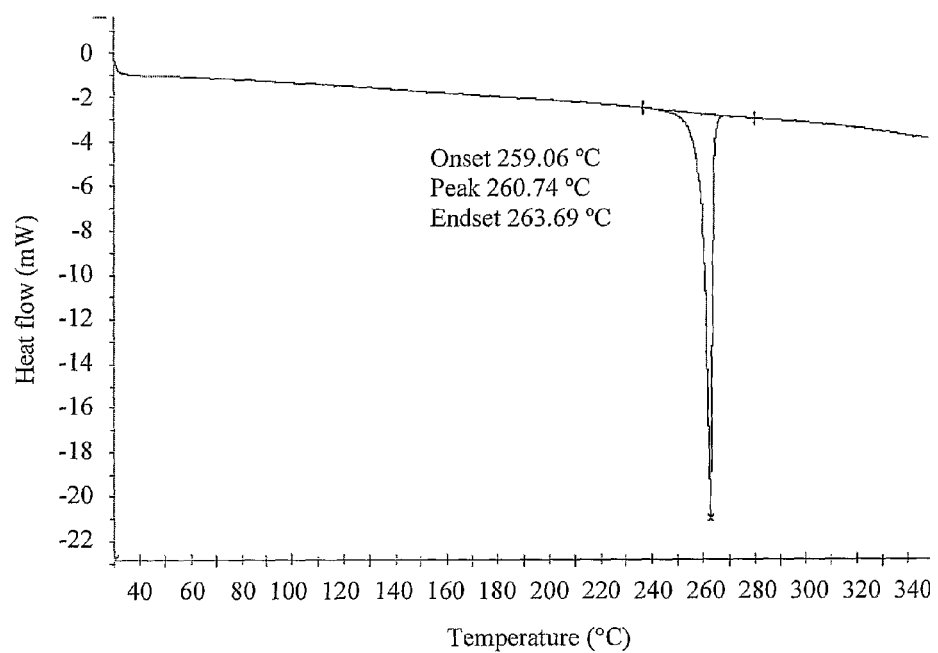
FIG. 2 illustrates a characteristic Differential Scanning calorimetry (DSC) profile of crystalline Form I of deferasirox.
Figure 3:
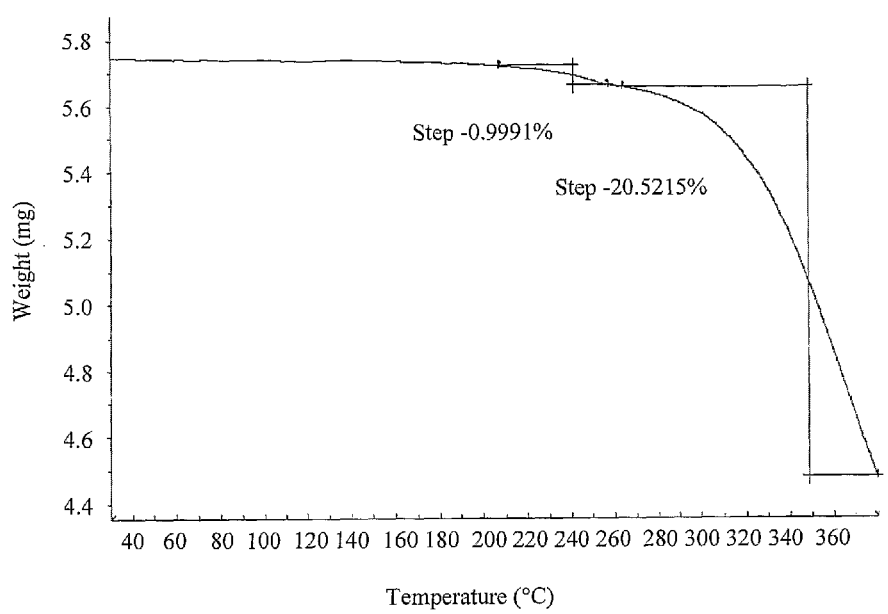
FIG. 3 illustrates a characteristic Thermogravimetric analysis (TGA) profile of crystalline Form I of deferasirox.

Deferasirox Form I:

As noted above, IPCOM000 146862D describes a crystalline form of deferasirox, designated form I. In one embodiment, Form I is characterized by X-ray powder diffraction having peaks at about 13.2, 14.1 and 16.6±0.2 degrees 2θ. Form I may be further characterized by X-ray powder diffraction having peaks at about 6.6, 10.0, 10.6, 20.3, 23.1, 25.7 and 26.2±0.2 degrees 2θ and by an X-ray powder diffraction pattern depicted in FIG. 1. Form I may also be characterized by a DSC profile as set forth in FIG. 2, and a TGA profile as set forth in FIG. 3.

In yet another embodiment, the present invention provides processes for preparing a crystalline deferasirox Form I characterized by an X-ray diffraction pattern substantially as shown in FIG. 1. The processes comprise the step of drying a deferasirox selected from the group consisting of: the crystalline deferasirox hemi-hydrate (Form II), the crystalline deferasirox hemi-DMSO solvate (Form V), the crystalline deferasirox mono-DMF solvate (Form VI), and the amorphous deferasirox and a crystalline deferasirox hemi-DMF solvate (Form III), as those forms are described herein, wherein the drying is conducted at a temperature from about room temperature to about 160° C. In one embodiment, the process is conducted at a temperature of about 120° C. In another embodiment, the drying is conducted at a temperature of about 60° C.

It is noted that the methods set forth herein for the preparation of the novel Forms of deferasirox are exemplary in nature, and may be varied as known to a person of skill in the art. Thus, the crystalline pseudopolymorphic forms of the present invention as well as the novel amorphous form can be prepared by a variety of methods, including for example, crystallization/precipitation or recrystallization from a suitable solvent, sublimation, growth from a melt, solid state transformation from another phase, crystallization/precipitation from a supercritical fluid, and jet spraying. Techniques for crystallization or recrystallization of crystalline forms from a solvent mixture include, for example, evaporation of the solvent, decreasing the temperature of the solvent mixture, crystal seeding a supersaturated solvent mixture of the molecule and/or salt, freeze drying the solvent mixture, and addition of anti-solvents (countersolvents) to the solvent mixture. The term "anti-solvent" as used herein refers to a solvent in which the compound has low solubility. Water is an exemplary and non-limiting example of an anti-solvent to be used in the context of the present invention.

Suitable solvents and anti-solvents for preparing crystals include polar and nonpolar solvents. The choice of solvent or solvents is typically dependent upon one or more factors, including solubility of the compound in such solvent, crystallization technique, and vapor pressure of the solvent. Combinations of solvents may be employed; for example, the compound may be solubilized into a first solvent followed by the addition of an anti-solvent to decrease the solubility of the compound in the solution and to induce crystallization. Suitable solvents include, but are not limited to, polar aprotic solvents and polar protic solvents, and mixtures thereof. Particular examples of suitable polar aprotic solvents include, but are not limited to, acetonitrile (ACN), tetrahydrofuran (THF), 2-methyl THF (2-MeTHF), methyl ethyl ketone (MEK), methyl isobutyl ketone (MIBK), methyl t-butyl ketone (MTBE), dichloromethane ($CH_2Cl_2$), acetone, ethyl acetate (EtOAc), isopropyl acetate (iPrOAc), dimethylformamide (DMF), dimethylsulfoxide (DMSO), N-methylpyrrolidone (NMP), toluene 1,4-dioxane, heptane, and mixtures thereof. Examples of suitable polar protic solvents include, but are note limited to, methanol (MeOH), ethanol (EtOH), isopropanol (IPA), 1-butanol, and mixtures thereof.

Seed crystals may be added to any crystallization mixture to promote crystallization as is known in the art. Alternatively, crystalline forms may be obtained by distillation or solvent addition techniques such as those known to those skilled in the art. Suitable solvents for this purpose include any of those solvents described herein, including protic polar solvents, such as alcohols (for example, methanol, ethanol, and isopropanol), aprotic polar solvents (including those listed above), and ketones (for example, acetone, methyl ethyl ketone, and methyl isobutyl ketone).

Exemplary processes used to prepare each of the polymorphic, pseudopolymorphic and amorphous deferasirox forms of the present invention are provided herein.

Methods for "crystallization from solution" include, but are not limited to, a concentration method, a slow cooling method, a reaction method (diffusion method, electrolysis method), a hydrothermal growth method, a fusing agent method, and so forth. The solution can be a supersaturated solution, optionally heated to temperatures bellow the solvent boiling point. The recovery of the solid state forms can be done for example, by filtering the suspension and drying.

In particular, the deferasirox forms of the present invention can be prepared by the slurry method as is well known in the art. Suspensions of the active ingredient in different solvents or mixture of solvents are prepared and shaken for long intervals (typically 24 hours). The deferasirox forms of the present invention can be prepared using slow or fast precipitation from saturated solutions in different solvents or mixture of solvents which are allowed to evaporate at room temperatures. Alternatively the saturated solutions can be heated followed by their cooling to induce precipitation as is known in the art.

Also encompassed by the present invention are methods of anti-solvent precipitation where an anti-solvent is added to the saturated solution of the active ingredient in different solvents or mixture of solvents to induce precipitation.

Within the scope of the present invention are also high pressure techniques where the active ingredient is compressed using various forces as is known in the art.

Pharmaceutical Compositions and Therapeutic Uses

The novel forms of deferasirox are useful for treating iron overload. The present invention thus provides pharmaceutical compositions comprising as an active ingredient the deferasirox polymorphs and pseudopolymorphs disclosed herein (i.e., Forms I, II, III, IV, V and VI, preferably Form II, Form V or Form VI), or the amorphous deferasirox form disclosed herein, and a pharmaceutically acceptable carrier.

In some embodiments, the present invention provides a pharmaceutical composition comprising as an active ingredient any one of the deferasirox forms of the present invention, e.g., a crystalline deferasirox hemi-hydrate (Form II), a crystalline deferasirox hemi-DMSO solvate (Form V), a crystalline deferasirox mono-DMF solvate (Form VI), or an amorphous deferasirox, and a pharmaceutically acceptable carrier.

The solid state polymorphs of the present invention can be safely administered orally or non-orally (e.g., topical, rectal). The pharmaceutical compositions can be formulated as tablets (including sugar-coated tablets, effervescent tablets and film-coated tablets), powders, granules, capsules (including soft capsules), orally disintegrating tablets, and sustained-release preparations as is well known in the art.

Pharmacologically acceptable carriers that may be used to produce the pharmaceutical composition of the present invention include various organic or inorganic carriers including, but not limited to, excipients, lubricants, binders, disintegrants, water-soluble polymers and basic inorganic salts. The pharmaceutical composition may further include additives such as, but not limited to, preservatives, antioxidants, coloring agents, sweetening agents, souring agents, bubbling agents and flavorings.

Suitable excipients include e.g. lactose, sucrose, D-mannitol, starch, cornstarch, crystalline cellulose, light silicic anhydride and titanium oxide. Suitable lubricants include e.g. magnesium stearate, sucrose fatty acid esters, polyethylene glycol, talc and stearic acid. Suitable binders include e.g. hydroxypropyl cellulose, hydroxypropylmethyl cellulose, crystalline cellulose, a-starch, polyvinylpyrrolidone, gum arabic powder, gelatin, pullulan and low-substitutional hydroxypropyl cellulose. Suitable disintegrants include e.g. crosslinked povidone (any crosslinked 1-ethenyl-2-pyrrolidinone homopolymer including polyvinylpyrrolidone (PVPP) and 1-vinyl-2-pyrrolidinone homopolymer), crosslinked carmellose sodium, carmellose calcium, carboxymethyl starch sodium, low-substituted hydroxypropyl cellulose, cornstarch and the like. Suitable water-soluble polymers include e.g. cellulose derivatives such as hydroxypropyl cellulose, polyvinylpyrrolidone, hydroxypropylmethyl cellulose, methyl cellulose and carboxymethyl cellulose sodium, sodium polyacrylate, polyvinyl alcohol, sodium alginate, guar gum and the like. Suitable basic inorganic salts include e.g. basic inorganic salts of sodium, potassium, magnesium and/or calcium. Particular embodiments include the basic inorganic salts of magnesium and/or calcium. Basic inorganic salts of sodium include, for example, sodium carbonate, sodium hydrogen carbonate, disodiumhydrogenphosphate, etc. Basic inorganic salts of potassium include, for example, potassium carbonate, potassium hydrogen carbonate, etc. Basic inorganic salts of magnesium include, for example, heavy magnesium carbonate, magnesium carbonate, magnesium oxide, magnesium hydroxide, magnesium metasilicate aluminate, magnesium silicate, magnesium aluminate, synthetic hydrotalcite, aluminahydroxidemagnesium and the like. Basic inorganic salts of calcium include, for example, precipitated calcium carbonate, calcium hydroxide, etc.

Suitable preservatives include e.g. sodium benzoate, benzoic acid, and sorbic acid. Suitable antioxidants include e.g. sulfites, ascorbic acid and a-tocopherol. Suitable coloring agents include e.g. food colors such as Food Color Yellow No. 5, Food Color Red No. 2 and Food Color Blue No. 2 and the like. Suitable sweetening agents include e.g. saccharin sodium, dipotassium glycyrrhetinate, aspartame, stevia and thaumatin. Suitable souring agents include e.g. citric acid (citric anhydride), tartaric acid and malic acid. Suitable bubbling agents include e.g. sodium bicarbonate. Suitable flavorings include synthetic substances or naturally occurring substances, including e.g. lemon, lime, orange, menthol and strawberry.

The solid forms of the present invention are particularly suitable for oral administration in the form of tablets, capsules, pills, dragées, powders, granules and the like. A tablet may be made by compression or molding, optionally with one or more excipients as is known in the art. Specifically, molded tablets may be made by molding in a suitable machine a mixture of the powdered active ingredient moistened with an inert liquid diluent.

The tablets and other solid dosage forms of the pharmaceutical compositions described herein may optionally be scored or prepared with coatings and shells, such as enteric coatings and other coatings well known in the art. They may also be formulated so as to provide slow or controlled release of the active ingredient therein using, for example, hydroxypropylmethyl cellulose in varying proportions to provide the desired release profile, other polymer matrices and the like. The active ingredient can also be in micro-encapsulated form, if appropriate, with one or more of the above-described excipients.

The present invention provides a method of treating chronic iron overload due to e.g., multiple blood transfusions, using the deferasirox forms of the present invention.

In various embodiments, the present invention provides a pharmaceutical composition comprising as an active ingredient any one of the deferasirox forms of the present invention, and a pharmaceutically acceptable carrier for use in treating iron overload.

In some embodiments, the present invention provides a method treating chronic iron overload due to, e.g., multiple blood transfusions, comprising administering to a subject in need thereof an effective amount of a composition comprising any one of the deferasirox forms of the present invention, e.g., a crystalline deferasirox hemi-hydrate (Form II), a crystalline deferasirox hemi-DMSO solvate (Form V), a crystalline deferasirox mono-DMF solvate (Form VI), or an amorphous deferasirox.

In additional embodiments, the present invention provides use of any one of the deferasirox forms of the present invention for the preparation of a medicament for treating iron overload. In additional embodiments, the present invention provides use of any one of the deferasirox forms of the present invention for treating iron overload.

The other polymorphic forms described herein (i.e., Form I, Form III (hemi-DMF solvate) or Form IV (mono-THF solvate) can also be used in the pharmaceutical compositions and methods of the present invention.

In specific embodiments, the subject is a mammal, preferably a human. Patient populations who are anticipated to benefit from the treatment methods of the present invention include those who have chronic anemias such as thalassemia or sickle cell anemia, which often require regular red blood cell transfusions. The novel deferasirox forms of the present invention are thus useful in treating transfusion-dependent chronic iron overload, or any other disorders which are characterized by iron overload (e.g. after increased uptake of iron from the gastrointestinal tract). The deferasirox forms of the present invention are also useful in treating disorders which are linked with an excess of other metals, particularly trivalent metals, in the body tissues (e.g. excess of aluminum in dialysis encephalopathy and osteomalacia, as well as in Alzheimer's disease).

"An effective amount", or alternatively "a therapeutically effective amount" as used herein refers to an amount of an agent which is effective, upon single or multiple dose administration to the subject to provide a therapeutic benefit to the subject. In one embodiment, the therapeutic benefit is the treatment of transfusion-dependent chronic iron overload.

The principles of the present invention are demonstrated by means of the following non-limitative examples.

EXAMPLES

The invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

Unless otherwise noted, the materials used in the examples were obtained from readily available commercial suppliers or synthesized by standard methods known to one skilled in the art of chemical synthesis. The work-up treatment in each step can be applied by a typical method, wherein isolation and purification is performed as necessary by selecting or combining conventional methods, such as crystallization, recrystallization, distillation, partitioning, silica gel chromatography, preparative HPLC and the like.

Example 1

Process A o-Trimethylsiloxybenzonitrile (IV, X=SiMe$_3$) was prepared as described in Great Britain patent GB 1330265 or in Tetrahedron Letters, 1986, 27(3): 347-348.

2-(Methoxymethyl)oxybenzonitrile (IV, X=MOM) was prepared according to Tetrahedron, 2003, 59: 5831-5836.

2-Acetoxybenzonitrile (IV, X=Ac) was prepared as described in Bulletin de la Societe Chimique de France, 1958, 185-187.

Typical Preparation of the Compound of Formula II:

Dioxane 17.6 g (0.2 mol) in 75 ml of dichloroethane was treated dropwise at 0-3° C. with 16.0 g (0.2 mol) of sulfur trioxide with cooling and stirring under inert atmosphere to yield a slurry of dioxane-sulfur trioxide complex. Nitrile IV (0.4 mol) in 100 ml of dichloroethane was then added to the reaction mixture and the temperature was allowed to slowly increase to room temperature. Monitoring of the reaction was performed by TLC. After completion of the reaction, the solids were filtered off, washed with dichloroethane and dried in vacuum. Evaporation of the mother liquid generally provides an additional portion of semisolid mass, which crystallized at standing. The yield is 78-95%.

Preparation of Compound I (Deferasirox):

0.2 mol of compound II (X=SiMe$_3$) was added to a solution of 4-hydrazinobenzoic acid ethyl ester (0.3 mol) in 150 ml of ethanol abs. The mixture was stirred at room temperature under TLC monitoring. After completion of the reaction, water was added until some perturbation (i.e. a first sign of precipitation) was observed. The mixture was concentrated to a total volume of 50% under reduced pressure and aqueous 6 M HCl (40 mL) was added. The mixture was stirred until TLC analysis indicated complete deprotection of protecting groups and deferasirox formation. The resulting solid was filtered, washed with mixture ethanol-water and dried for 24 h in vacuum (85% yield). The solid was allowed to stand exposed to the air to form the monohydrate.

Example 2

Process B

Preparation of Salicyloyl Chloride

Salicylic acid (5.0 g, 36.2 mmol) was suspended in dry hexane (40 ml) and thionyl chloride (4.52 g, 38 mmol) was added under nitrogen atmosphere followed by one drop of pyridine. The mixture was refluxed for two hours while stirring. The clear yellow solution was cooled and concentrated in vacuum, giving a dense oil to be used in the next step.

Preparation of 2-hydroxy-N-(2-hydroxybenzoyl) benzamide[(di(salycyl)imide](4)

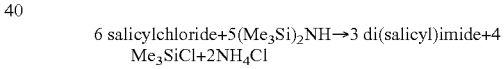

The previously prepared salicyl chloride was dissolved in dry toluene (10 ml) and added dropwise to a solution of hexamethyldisilazane (4.954 g, 30.8 mmol) in dry toluene (20 ml). The mixture was stirred at 0-10° C. under nitrogen atmosphere for 1 hour. The mixture was then filtered and the filtrate concentrated under reduced pressure. Ethanol was added to the residue and the reaction mixture was refluxed. After cooling, the precipitate was filtered and dried in vacuum, giving a white to off-white solid with 50% yield. Separation from mother liquid gave an additional amount of compound (4) with 75% overall yield.

m.p. 197-199°; lit. m.p. 188-190° [J. Chem. Soc., 1958, 23, 893-896]

$^1$H NMR (500 MHz, DMSO-d$_6$): δ: 7.831 (dd, J=7.5, 2 Hz, 1H), 7.745 (td, J=7.5, 1.5 Hz, 1H), 7.388 (s, 1H), 7.286 (s, 1H), 7.184 (s, 1H), 7.077 (d, J=8.5 Hz, 1H), 6.975 (t, J=7.5 Hz 1H).

ESIMS(+): [M+H]=257.9; ESIMS (−): [M−H]=256.1

Preparation of 4-[3,5-Bis(2-hydroxyphenyl)-1,2,4-triazol-1-yl]benzoic acid (deferasirox)

Disalicylimide (4) (3.7 g, 14.32 mmol) and 4-hydrazinobenzoic acid (2.6 g, 17.14 mmol) were suspended in ethanol (50 ml) and refluxed, adding TFA in portions until most of the reagents were dissolved (6% v/v), monitoring the reaction progress by HPLC. After 4 h no more starting material was present. The mixture was cooled and concentrated. After cooling the precipitate was filtered. The solid was recrystallized from ethanol-water, filtered, washed with mixture ethanol-water and dried for 24 h in vacuum to give desired compound with 85% yield.

$^1$H NMR (400 MHz, DMSO-d$_6$): δ: 6.87 (d, J=8.4 Hz, 1H), 7.045-6.97 (m, 3H), 7.24 (m, 2H), 7.405 (qd, J=7.6, 1.6 Hz, 2H), 7.558 (d, J=10 Hz, 3H), 7.98 (d, J=8.4 Hz, 2H), 8.059 (dd, J=7.6, 2 Hz, 1H), 10.059 (s, OH), 10.812 (s, OH).

EI-MS calcd for C$_{21}$H$_{15}$N$_3$O$_4$ MW 373.11. found m/z 373.11

Anal. Calcd for C$_{21}$H$_{15}$N$_3$O$_4$ (373.36): C, 67.56; H, 4.05; N, 11.25. Found: C, 67.48; H, 4.0; N, 10.98.

Example 3

General Preparation Methods of Deferasirox Polymorphs

1. Reagents
Acetonitrile, HPLC grade, Sigma, Lot No. 07278PH
Ethanol, HPLC grade, Sigma, Lot No. 11085CH
DMSO, HPLC grade, Sigma, Lot No. 05737BH
Dichloride methane, Alfa Aesar, HPLC grade, Lot No. C27S008
Methanol, AR, SCRC, Lot No. T20090912
Ethanol Acetate, AR, Yixing Secondary Chemical Company, Lot No. 090607
MIBK, AR, SCRC, Lot No. T20080411
Isopropyl alcohol, AR, Sinopharm Chemical Reagent Co. Ltd, Lot No. T20090813
Acetone, AR, Sinopharm Chemical Reagent Co. Ltd, Lot No. 090104
Toluene, AR, SCRC, Lot No. T20090603
tert-Butyl methyl ether, HPLC grade, Fluka, Lot No. 1359496
THF, AR, Yixing Secondary Chemical, Lot No. 090901
1-Butanol, AR, SCRC, Lot No. T20080818
MEK, AR, SCRC, Lot No. T20090724
iPrOAc, AR, Shanghai Experimental Reagent Company, Lot No. 20080410
2-Me-THF, AR, Shanghai Jiachen Chemical Reagent Co. Ltd, Lot No. 090323
Heptane, HPLC grade, Sigma-Aldrich, Lot No. 05442LH
N-methylpyrrolidone, HPLC grade, Sigma-Aldrich, Lot No. S86863-279
2. Instruments
Sartorius CP 225D Balance
ELGA Water Purification Equipment
Mettler Toledo DSC 1
Mettler Toledo TGA/DSC 1
Rigaku D/MAX 2200 X-ray powder diffractometer
Thermo Nicolet 380 FT-IR
NMR Varian 400
Nikon LV100 Polarized Light Microscopy
3. XRPD, DSC, TGA and Microscope Methods
3.1 XRPD method
Details of XRPD method used in the tests are mentioned below:
  X-ray Generator: Cu, kα, (λ=1.54056 Å).
  Tube Voltage: 40 kV, Tube Current: 40 mA.
  DivSlit: 1 deg.
  DivH.L.Slit: 10 mm
  SctSlit: 1 deg.
  RecSlit: 0.15 mm
  Monochromator: Fixed Monochromator
  Scanning Scope: 2-40 deg.
  Scanning Step: 10 deg/min
3.2 DSC and TGA Methods
Details of DSC method used in the tests are mentioned below:
  Heat from 30° C. to 350° C. at 10° C./min
Details of TGA method used in the tests are mentioned below:
  Heat from 30° C. to 380° C. at 10° C./min
4. Characterization of the Deferasirox Form I
  Form I of deferasirox was characterized by XRPD, DSC (Deferasirox was placed in an aluminum pan with pinhole) and TGA. The results are listed in FIG. 1 to FIG. 3, respectively.
5. General Preparation Methods
  5a. General Method I: Slurry Method
  Suspensions of deferasirox (Form I) in different solvents or mixed solvents were prepared and kept shaking for 24 h. The suspensions were filtered and the filter cake was dried at room temperature overnight, then checked by XRPD. Several crystal forms were found, namely Forms III, IV and VI as set forth in the Examples below.
  5b. General Method II: Solvent Evaporation Method
  Solutions of deferasirox Form I in different solvents were prepared and filtered through 0.22 μm filter into a clean vessel. Solvent was evaporated at 50° C. or 60° C. to form crystals. The formed crystals were checked by XRPD. Several crystal forms were found, namely Forms III, Form IV and Form V as set forth in the Examples below.
  5c. Method III: Anti-Solvent Precipitation
  Deferasirox Form I was dissolved in various solvents at 80° C. to prepare saturated solutions. The solutions were filtered with 0.22 μm microporous film to get clear solution. Then, various amounts of anti-solvent were added (reaction kept at 25° C. or 80° C.) to precipitate out crystals. The formed crystal was analyzed by XRPD as wet cake. Form II was identified by this method, as set forth in the Examples below.
  5d. Method IV: Thermal Heating/Cooling
  Deferasirox Form I was heated to melt under vacuum and the crystallization of the melted compound was controlled by cooling it fast or slowly. The formed crystals were checked by XRPD. Amorphous deferasirox was identified by this method, as set forth in the Examples below.

Example 4

Deferasirox Form II (General Method III)

General method III was performed. Thus, approximately 100 mg of deferasirox Form I was dissolved in DMSO or DMF at 80° C. to prepare saturated solutions. The solutions were filtered with 0.22 μm microporous film to get clear solution. Then, 10 ml of water was added to precipitate out crystals which were identified as deferasirox Form II.

Form II showed two endothermic peaks (~53° C. and ~260° C.) in its DSC profile, and it contained approximately 2.1% H$_2$O as indicated by TGA.

Form II was further dried by heating (e.g. 60° C. for 1 h) after being checked by XRPD, DSC, TGA and NMR. The XRPD and DSC of Form II were rechecked following the dehydration process. Form II converted to Form I upon drying, which indicated that Form II is a hemi-hydrate.

Figure 7:
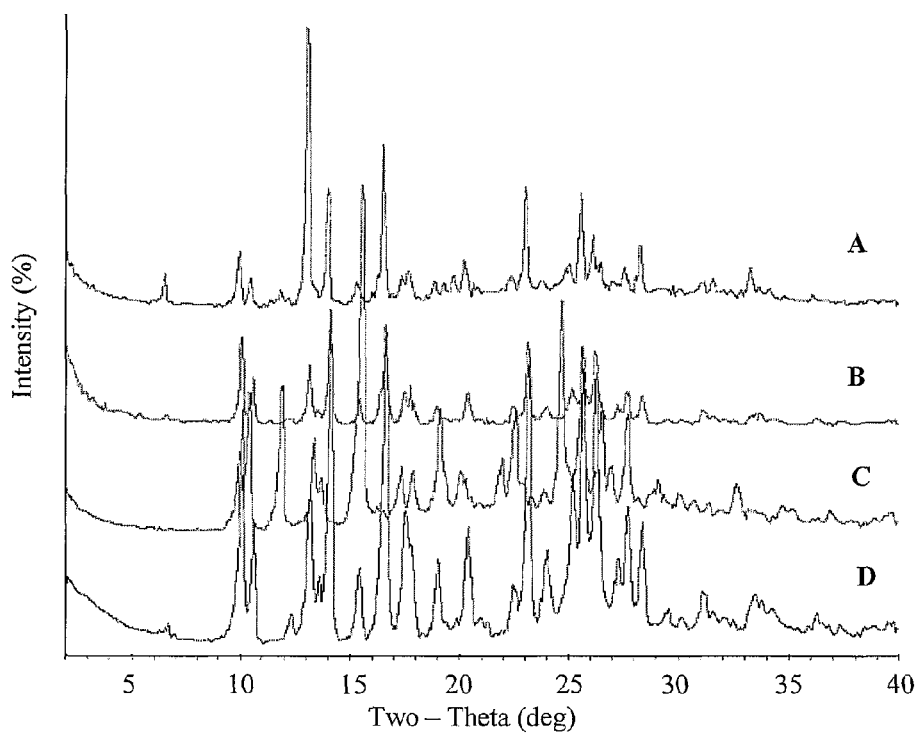
FIG. 7 illustrates a characteristic X-ray diffraction pattern of crystalline Form II of deferasirox (hemi-hydrate), before (7C) and after drying at 60° C. for 1 h (7B). Also shown for comparison are the X-ray diffraction patterns of deferasirox Form I (7D), designated "DFX-API", and deferasirox Form II after drying at 25° C. for 48 h (7A).
Figure 8:
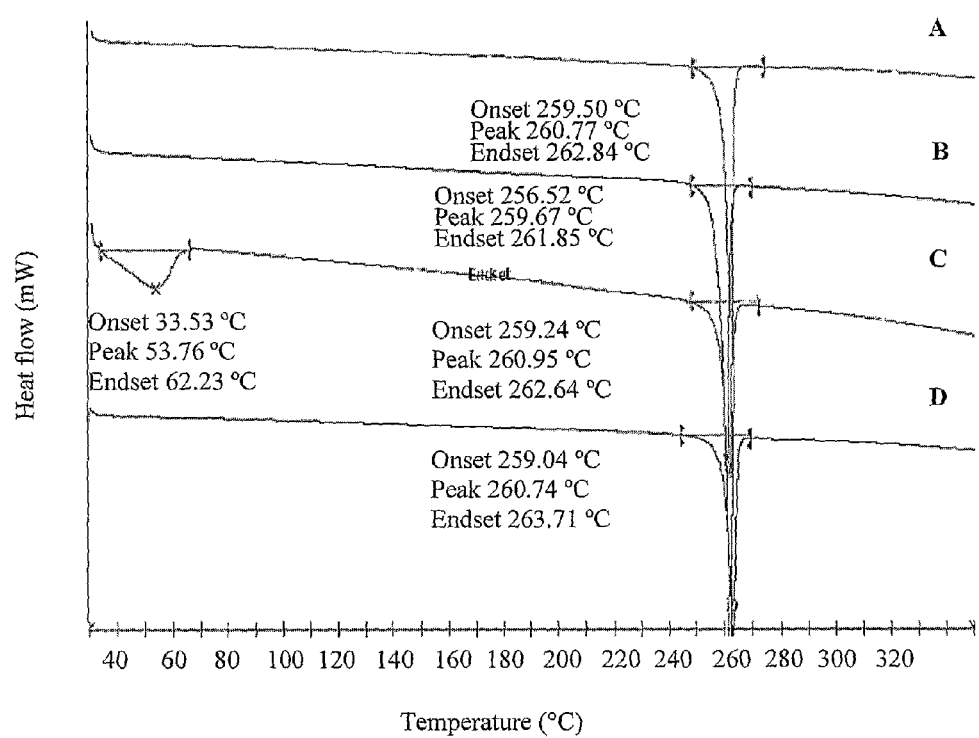
FIG. 8 illustrates a characteristic Differential Scanning calorimetry (DSC) profile of crystalline Form II of deferasirox (hemi-hydrate), before (8C; weight 1.1740 mg) and after drying at 60° C. for 1 h (8B; weight 2.1120 mg). Also shown for comparison are the Differential Scanning calorimetry profiles of deferasirox Form I (8D; weight 4.3050 mg), designated "DFX-API", and deferasirox Form II after drying at 25° C. for 48 h (8A; weight 1.6420 mg).

FIG. 4 illustrates a characteristic X-ray diffraction pattern of crystalline Form II of deferasirox. FIG. 5 illustrates a characteristic DSC profile of crystalline Form II of deferasirox. FIG. 6 illustrates a characteristic TGA profile of crystalline Form II of deferasirox Form II. FIG. 7 illustrates a characteristic X-ray diffraction pattern of crystalline Form II of deferasirox, before and after drying at 60° C. (also shown for comparison is the X-ray diffraction pattern of deferasirox Form I). FIG. 8 illustrates a characteristic DSC profile of crystalline Form II of deferasirox, before and after drying at 60° C. (also shown for comparison is the DSC profile of deferasirox Form I).

Example 5

Deferasirox Form III (General Methods I and II)

General method I was performed. A suspension of deferasirox Form I in DMF was prepared and kept shaking for 24 hours. The suspension was filtered and the filter cake was dried at room temperature overnight, then checked by XRPD.

Alternatively, general method II was performed. A solution of deferasirox Form I in DMF:1,4-dioxane (1:1 v/v), DMF:THF (1:1 v/v), DMF:EtOH (1:1 v/v) or DMF:EtOAc (1:1 v/v) was prepared and filtered through 0.22 μm filter into a clean vessel. Solvent was evaporated at 50° C. or 60° C. to form crystals of deferasirox Form III.

Form III showed two endothermic peaks (~114° C. and ~260° C.) in its DSC profile, and it contained approximately 12% DMF solvent as indicated by TGA and NMR.

Form III was further dried at 120° C. after being checked by XRPD, DSC, TGA and NMR. The XRPD and DSC were rechecked. Form III converted to Form I after being heated to 120° C. under vacuum for 1 hour, which indicated that Form III is a hemi-DMF solvate.

Figure 10:
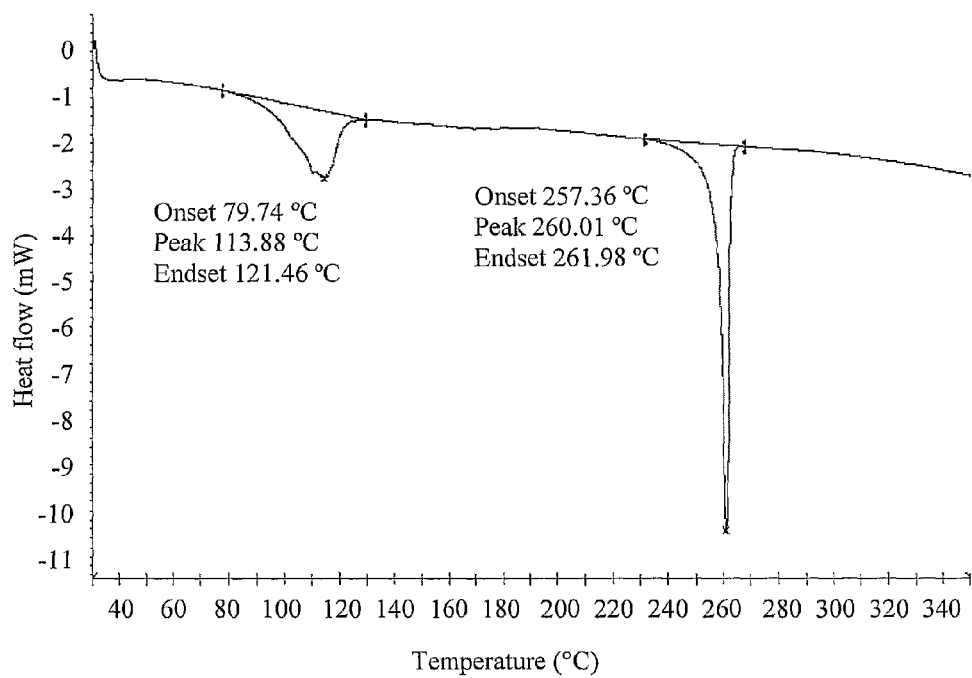
FIG. 10 illustrates a characteristic Differential Scanning calorimetry (DSC) profile of crystalline Form III of deferasirox (hemi-DMF solvate).
Figure 11:
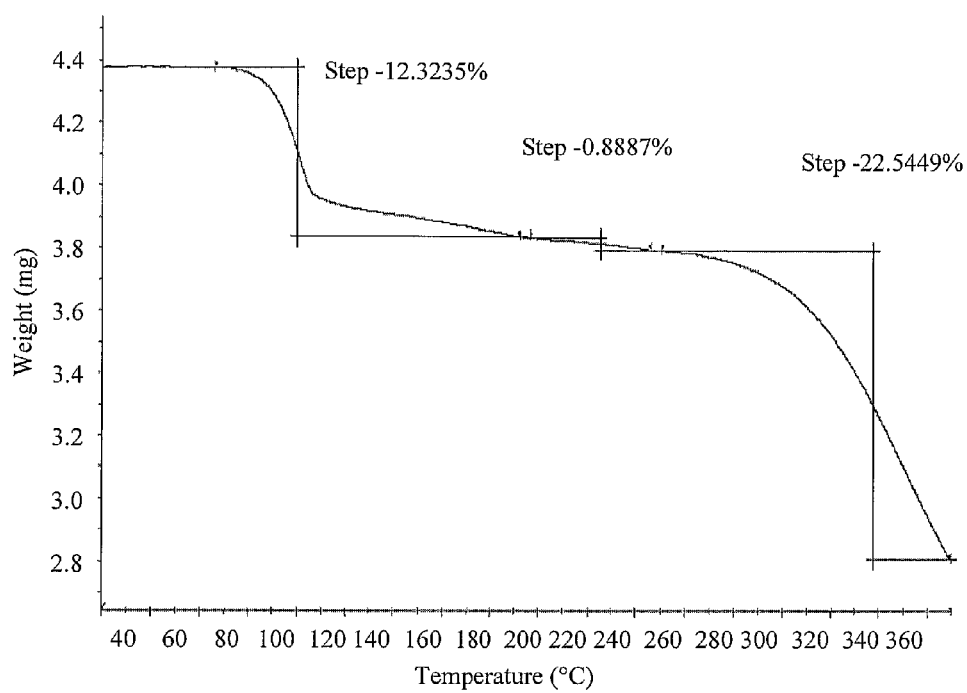
FIG. 11 illustrates a characteristic Thermogravimetric analysis (TGA) profile of crystalline Form III of deferasirox (hemi-DMF solvate).
Figure 12:
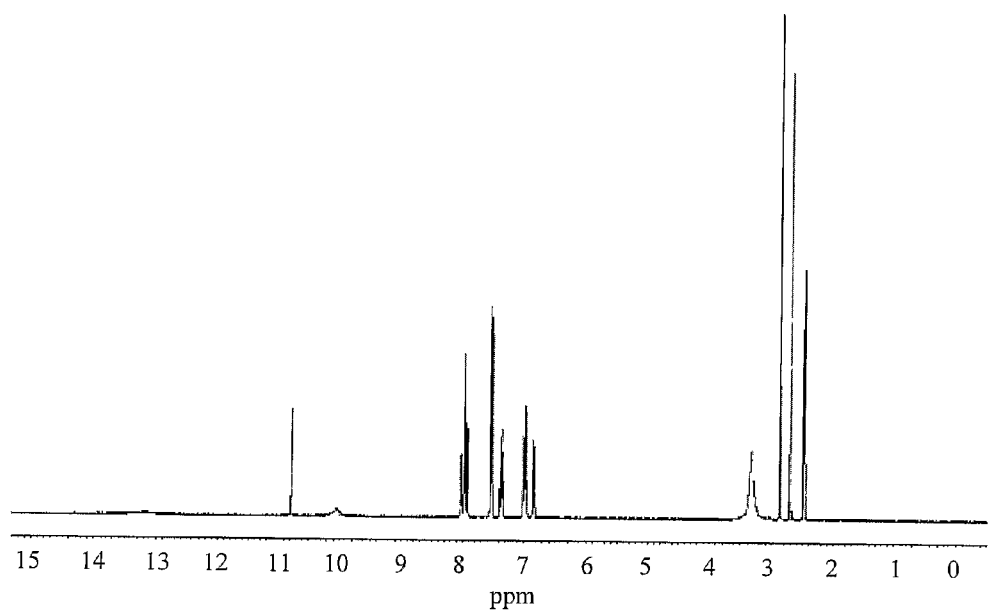
FIG. 12 illustrates a characteristic Nuclear Magnetic Resonance (NMR) profile of crystalline Form III of deferasirox (hemi-DMF solvate).
Figure 13:
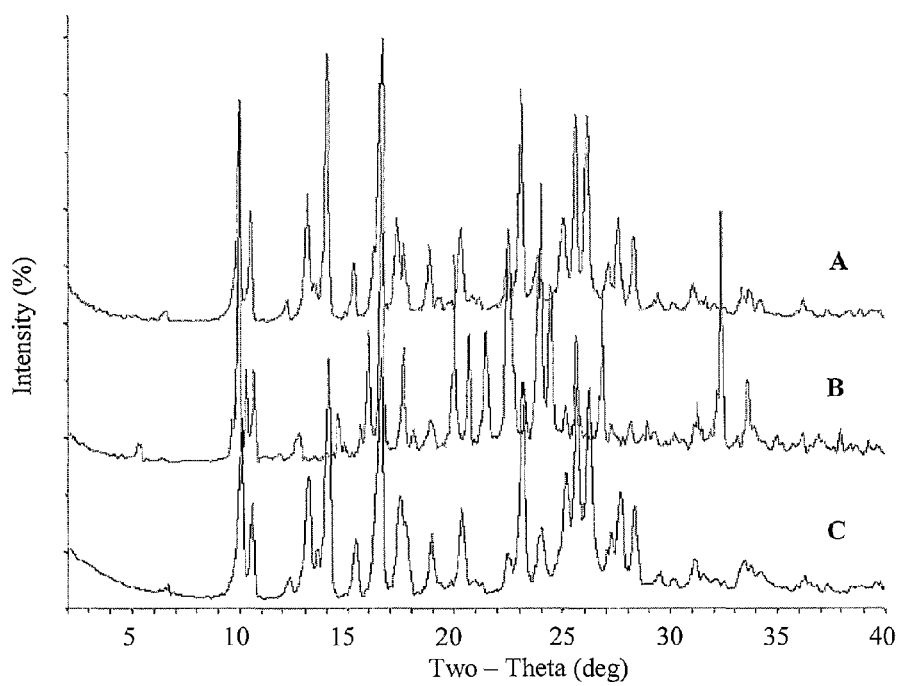
FIG. 13 illustrates a characteristic X-ray diffraction pattern of crystalline Form III of deferasirox (hemi-DMF solvate), before (13B) and after drying at 120° C. for 1 hour (13A). Also shown for comparison is the X-ray diffraction pattern of deferasirox Form I (13C), designated "DFX-API".
Figure 14:
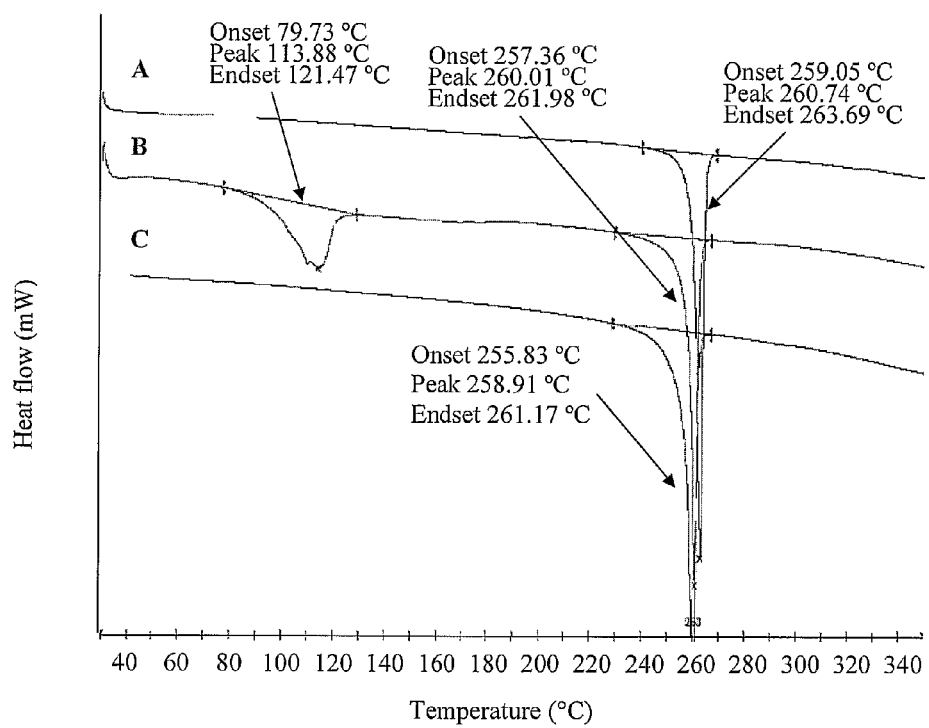
FIG. 14 illustrates a characteristic Differential Scanning calorimetry (DSC) profile of crystalline Form III of deferasirox (hemi-DMF solvate), before (14B; weight 2.3200 mg) and after drying at 120° C. for 1 hour (14C; weight 4.0990 mg). Also shown for comparison is the Differential Scanning calorimetry profile of deferasirox Form I (14A; weight 4.3050 mg), designated "DFX-API".

FIG. 9 illustrates a characteristic X-ray diffraction pattern of crystalline Form III of deferasirox. FIG. 10 illustrates a characteristic DSC profile of crystalline Form III of deferasirox. FIG. 11 illustrates a characteristic TGA profile of crystalline Form III of deferasirox. FIG. 12 illustrates a characteristic NMR profile of crystalline Form III of deferasirox. FIG. 13 illustrates a characteristic X-ray diffraction pattern of crystalline Form III of deferasirox, before and after drying at 120° C. for 1 hour (also shown for comparison is the X-ray diffraction pattern of deferasirox Form I). FIG. 14 illustrates a characteristic DSC profile of crystalline Form III of deferasirox, before and after drying at 120° C. for 1 hour (also shown for comparison is the DSC profile of deferasirox Form I).

Example 6

Deferasirox Form IV (General Methods I and II)

General method I was performed. A suspension of deferasirox Form I in THF was prepared and kept shaking for 24 hours. The suspension was filtered and the filter cake was dried at room temperature overnight, then checked by XRPD.

Alternatively, general method II was performed as described above. A solution of deferasirox Form I in THF:MEK (1:1 v/v) or THF:acetone (1:1 v/v) was prepared and filtered through 0.22 μm filter into a clean vessel. Solvent was evaporated at 50° C. or 60° C. to form crystals of deferasirox Form IV.

Form IV showed two endothermic peaks (~97° C. and ~260° C.) in its DSC profile, and it contained approximately 16% DMSO solvent as indicated by TGA and NMR.

Form IV converted to Form I after being heated to 120° C. with vacuum for 1 h, which indicated that Form IV is a mono-THF solvate.

Figure 16:
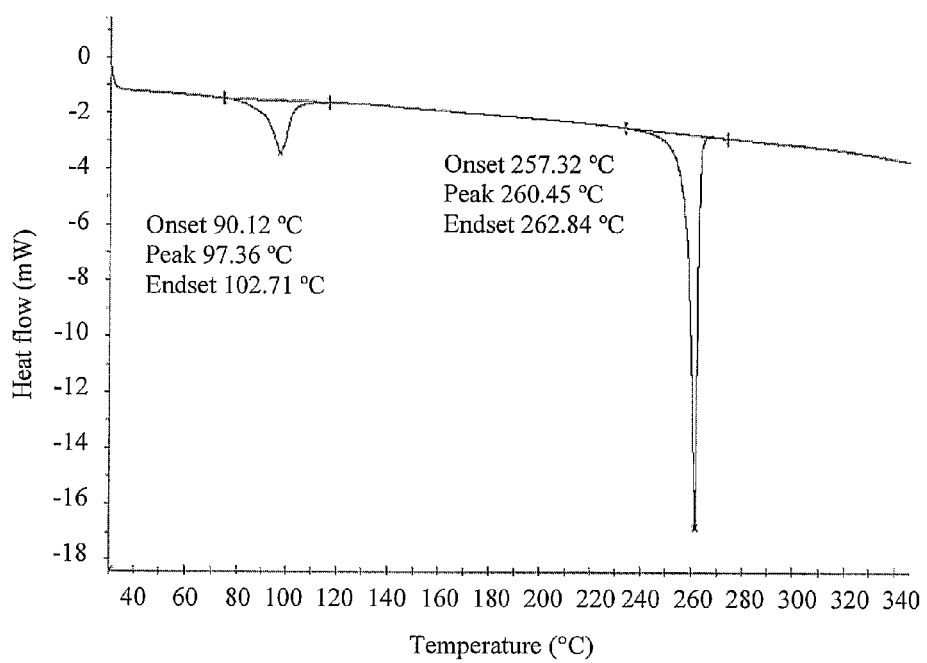
FIG. 16 illustrates a characteristic Differential Scanning calorimetry (DSC) profile of crystalline Form IV of deferasirox (mono-THF solvate).
Figure 17:
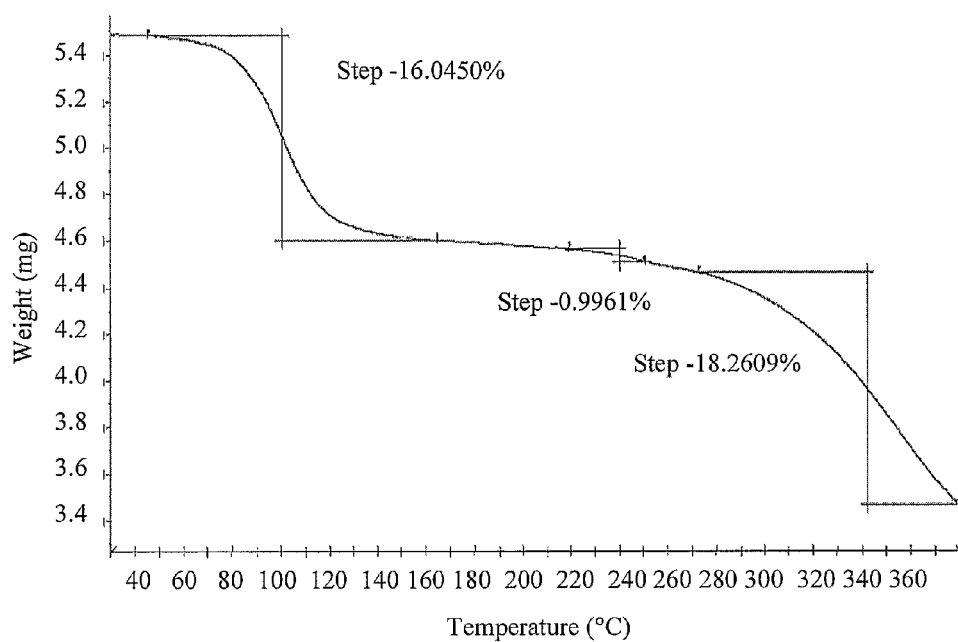
FIG. 17 illustrates a characteristic Thermogravimetric analysis (TGA) profile of crystalline Form IV of deferasirox (mono-THF solvate).
Figure 18:
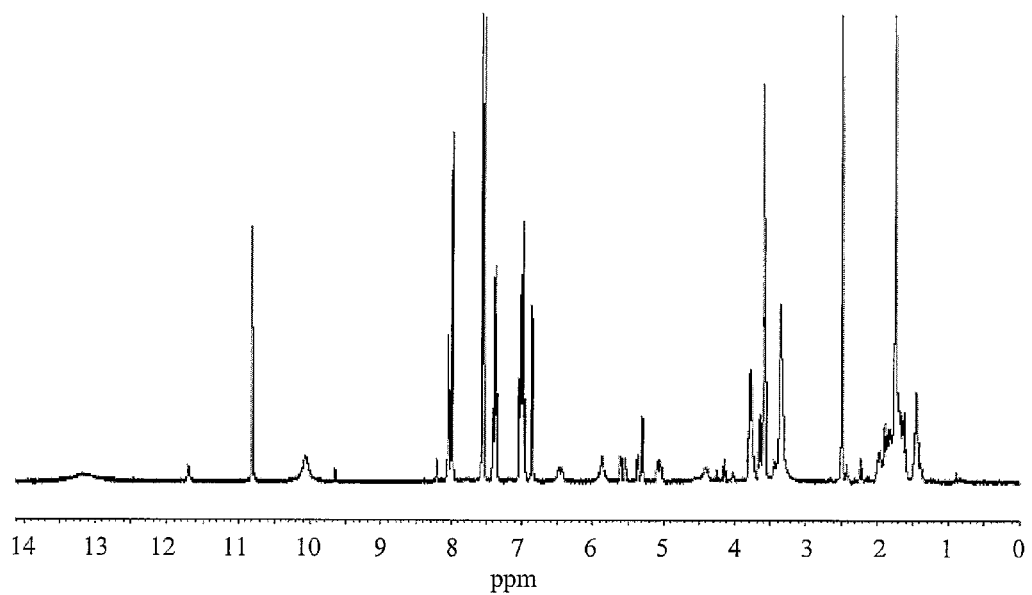
FIG. 18 illustrates a characteristic Nuclear Magnetic Resonance (NMR) profile of crystalline Form IV of deferasirox (mono-THF solvate).
Figure 19:
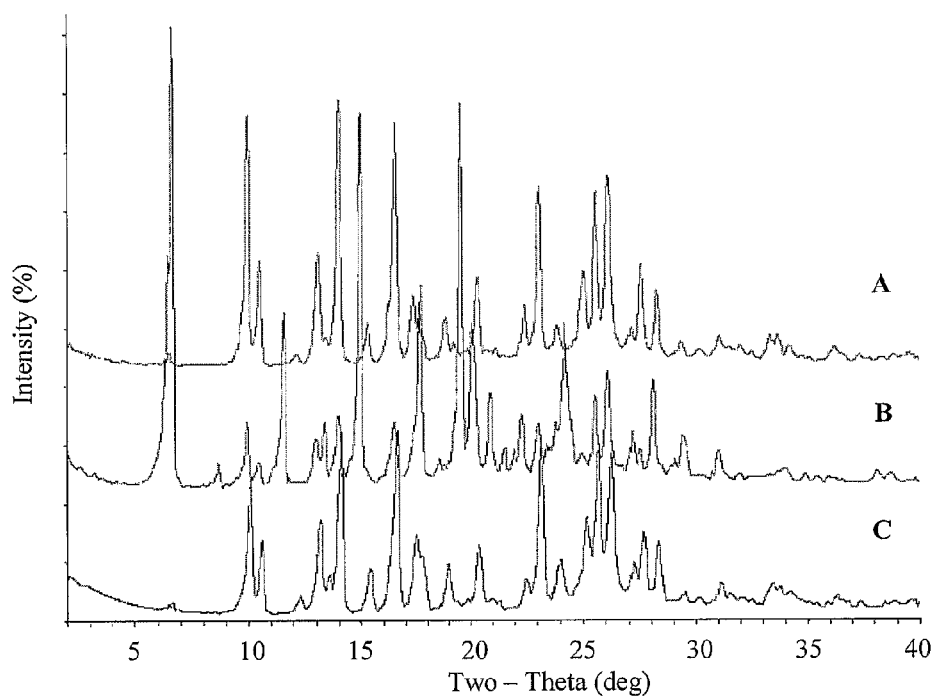
FIG. 19 illustrates a characteristic X-ray diffraction pattern of crystalline Form IV of deferasirox (mono-THF solvate), before (19B) and after drying at 120° C. for 1 hour (19A). Also shown for comparison is the X-ray diffraction pattern of deferasirox Form I (19C), designated "DFX-API".
Figure 20:
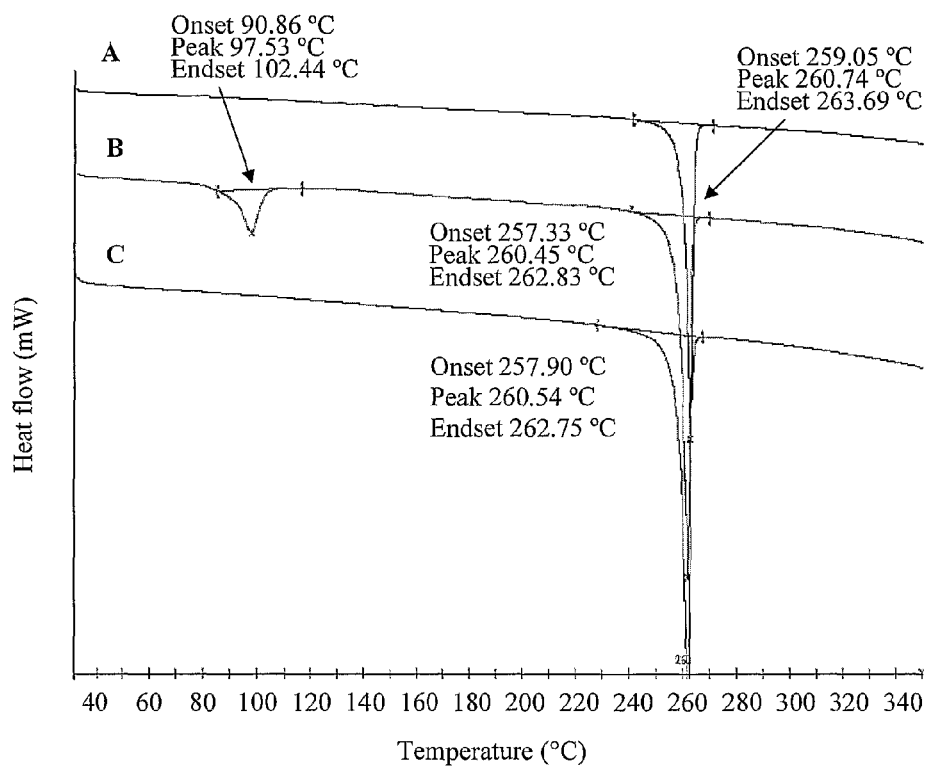
FIG. 20 illustrates a characteristic Differential Scanning calorimetry (DSC) profile of crystalline Form IV of deferasirox (mono-THF solvate), before (20B; weight 2.9030 mg) and after drying at 120° C. for 1 hour (20C; weight 3.0980 mg). Also shown for comparison is the Differential Scanning calorimetry profile of deferasirox Form I (20A; weight 4.3050 mg), designated "DFX-API".

FIG. 15 illustrates a characteristic X-ray diffraction pattern of crystalline Form IV of deferasirox. FIG. 16 illustrates a characteristic DSC profile of crystalline Form IV of deferasirox. FIG. 17 illustrates a characteristic TGA profile of crystalline Form IV of deferasirox. FIG. 18 illustrates a characteristic NMR profile of crystalline Form IV of deferasirox. FIG. 19 illustrates a characteristic X-ray diffraction pattern of crystalline Form IV of deferasirox, before and after drying at 120° C. for 1 hour (also shown for comparison is the X-ray diffraction pattern of deferasirox Form I). FIG. 20 illustrates a characteristic DSC profile of crystalline Form IV of deferasirox, before and after drying at 120° C. for 1 hour (also shown for comparison is the DSC profile of deferasirox Form I).

Example 7

Deferasirox Form V (General Method II)

General method II was performed. A solution of deferasirox Form I in DMSO:THF (1:1 v/v) or DMSO:DMF (1:1 v/v) was prepared and filtered through 0.22 μm filter into a clean vessel. Solvent was evaporated at 50° C. or 60° C. to form crystals of deferasirox Form V.

Form V showed two endothermic peaks (~89° C. and ~260° C.) in its DSC profile, and it contained approximately 7.3% DMSO solvent as indicated by TGA and NMR.

Form V converted to Form I after being heated to 120° C. with vacuum for 1 h, which indicated that Form V is a hemi-DMSO solvate.

Figure 25:
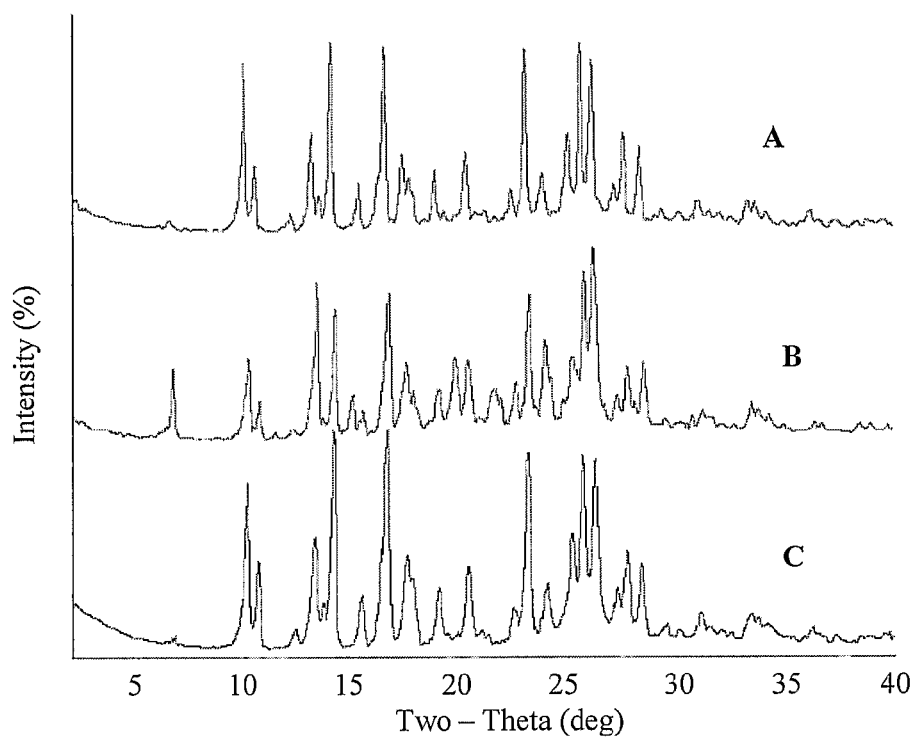
FIG. 25 illustrates a characteristic X-ray diffraction pattern of crystalline Form V of deferasirox (hemi-DMSO solvate), before (25B) and after drying at 120° C. for 1 hour (25A). Also shown for comparison is the X-ray diffraction pattern of deferasirox Form I (25C), designated "DFX-API".
Figure 26:
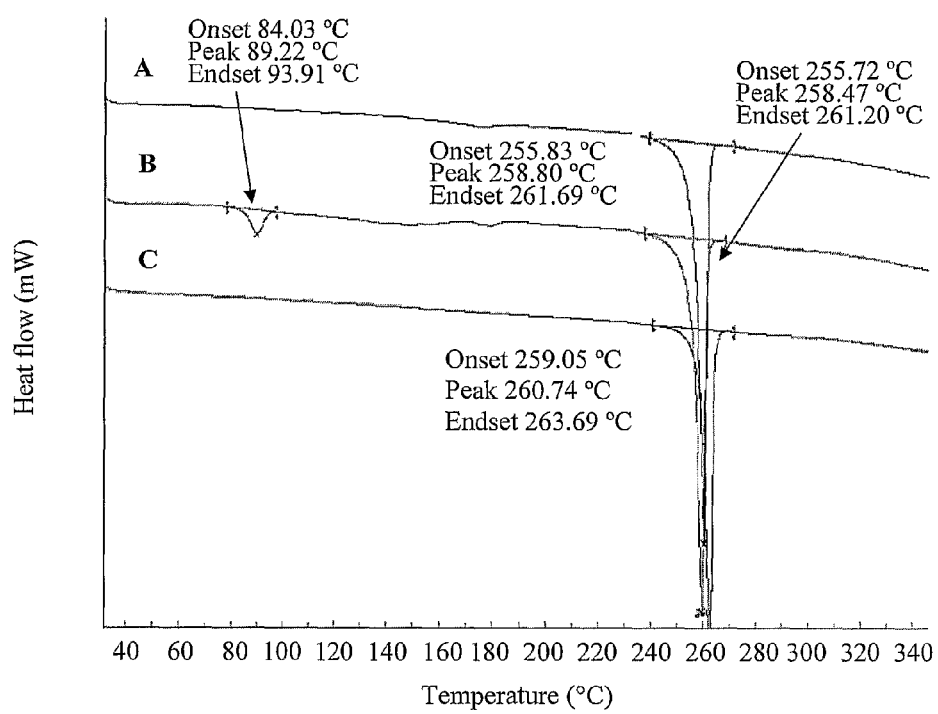
FIG. 26 illustrates a characteristic Differential Scanning calorimetry (DSC) profile of crystalline Form V of deferasirox (hemi-DMSO solvate), before (26B; weight 3.9140 mg) and after drying at 120° C. for 1 hour (26A; weight 4.6780 mg). Also shown for comparison is the Differential Scanning calorimetry profile of deferasirox Form I (26C; weight 4.3050 mg), designated "DFX-API".

FIG. 21 illustrates a characteristic X-ray diffraction pattern of crystalline Form V of deferasirox. FIG. 22 illustrates a characteristic DSC profile of crystalline Form V of deferasirox. FIG. 23 illustrates a characteristic TGA profile of crystalline Form V of deferasirox. FIG. 24 illustrates a characteristic NMR profile of crystalline Form V of deferasirox. FIG. 25 illustrates a characteristic X-ray diffraction pattern of crystalline Form V of deferasirox, before and after drying at 120° C. for 1 hour (also shown for comparison is the X-ray diffraction pattern of deferasirox Form I). FIG. 26 illustrates a characteristic DSC profile of crystalline Form V of deferasirox, before and after drying at 120° C. for 1 hour (also shown for comparison is the DSC profile of deferasirox Form I).

Example 8

Deferasirox Form VI (General Method I)

General method I was performed. A suspension of deferasirox Form I in 2-Me-THF:DMF (3:1 v/v) was prepared and kept shaking for 24 hours. The suspension was filtered and the filter cake was dried at room temperature overnight, then checked by XRPD. Crystals of deferasirox Form VI were identified.

Form VI showed three endothermic peaks (~117° C., ~125° C. and ~260° C.) in its DSC profile, and it contained approximately 10% DMF as indicated by TGA and NMR.

Form VI converted to Form I after being heated to 120° C. with vacuum for 1 h, which indicated that Form VI is a mono-DMF solvate.

Figure 31:
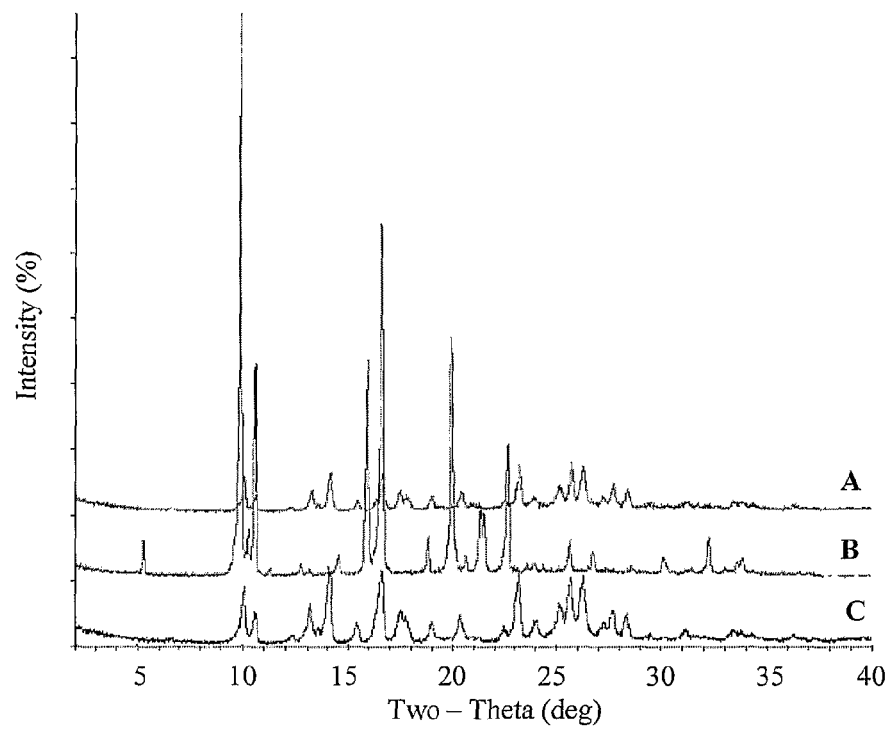
FIG. 31 illustrates a characteristic X-ray diffraction pattern of crystalline Form VI of deferasirox (mono-DMF solvate), before (31B) and after drying at 120° C. for 1 hour (31A). Also shown for comparison is the X-ray diffraction pattern of deferasirox Form I (31C), designated "DFX-API".
Figure 32:
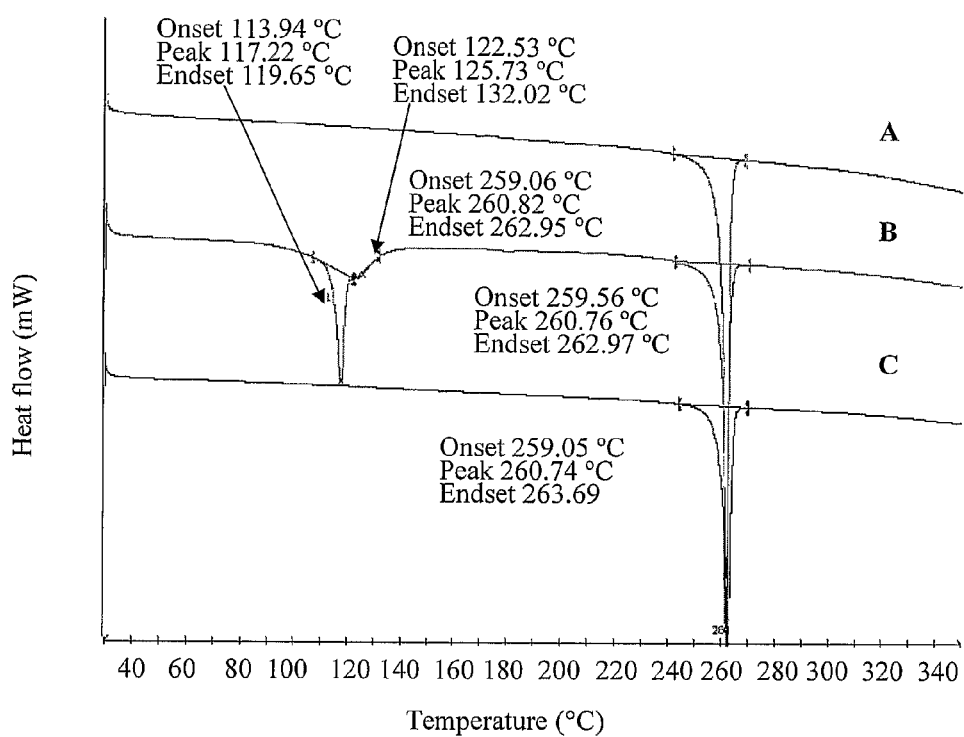
FIG. 32 illustrates a characteristic Differential Scanning calorimetry (DSC) profile of crystalline Form VI of deferasirox (mono-DMF solvate), before (32B; weight 2.5670 mg) and after drying at 120° C. for 1 hour (32A; weight 2.2030 mg). Also shown for comparison is the Differential Scanning calorimetry profile of deferasirox Form I (32C; weight 4.3050 mg), designated "DFX-API".

FIG. 27 illustrates a characteristic X-ray diffraction pattern of crystalline Form VI of deferasirox. FIG. 28 illustrates a characteristic DSC profile of crystalline Form VI of deferasirox. FIG. 29 illustrates a characteristic TGA profile of crystalline Form VI of deferasirox. FIG. 30 illustrates a characteristic NMR profile of crystalline Form VI of deferasirox. FIG. 31 illustrates a characteristic X-ray diffraction pattern of crystalline Form VI of deferasirox, before and after drying at 120° C. for 1 hour (also shown for comparison is the X-ray diffraction pattern of deferasirox Form I). FIG. 32 illustrates a characteristic DSC profile of crystalline Form VI of deferasirox, before and after drying at 120° C. for 1 hour (also shown for comparison is the DSC profile of deferasirox Form I).

Example 9

Amorphous Deferasirox (General Method IV)

General method IV was performed. Deferasirox Form I was heated to melt under vacuum and the crystallization of the melted compound was controlled by fast cooling. The formed crystals were checked by XRPD and found to be amorphous deferasirox.

Amorphous form showed a distinctive DSC profile comprised of one exothermic peak (~140° C.) and one endothermic peak (~260° C.). Amorphous deferasirox was heated to 160° C. under vacuum and kept at this temperature for 5 min. The formed crystal was rechecked by XRPD and DSC. Amorphous transformed into Form I during the heating process, which indicated that the exothermic peak in the DSC profile was due to the transformation of amorphous to Form I and the endothermic peak was the melting event of Form I.

Figure 36:
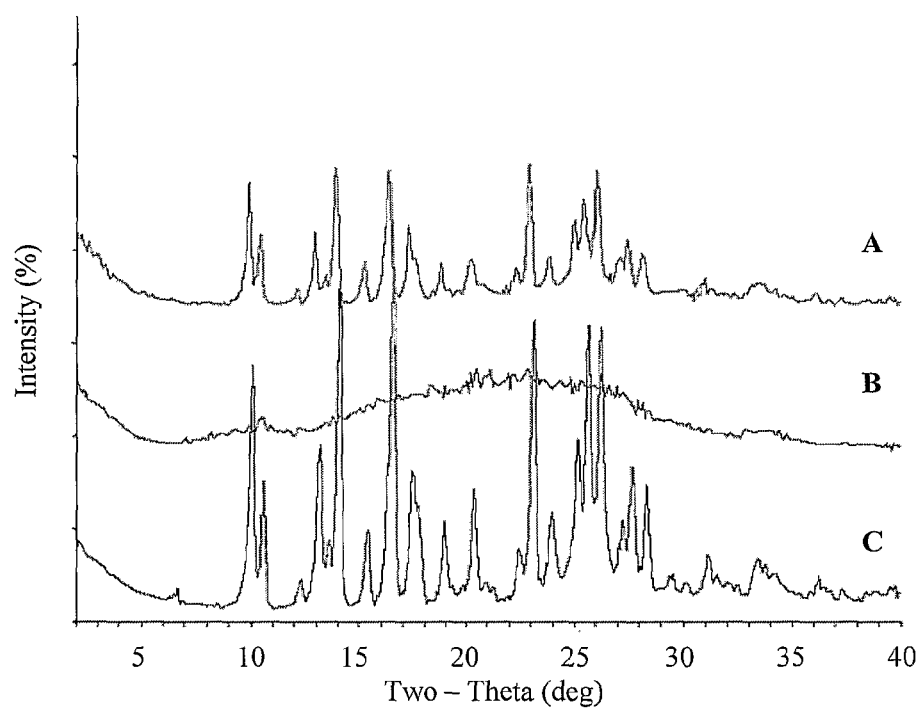
FIG. 36 illustrates a characteristic X-ray diffraction pattern of amorphous deferasirox, before (36B) and after drying at 160° C. for 5 minutes (36A). Also shown for comparison is the X-ray diffraction pattern of deferasirox Form I (36C), designated as "DFX-API".
Figure 37:
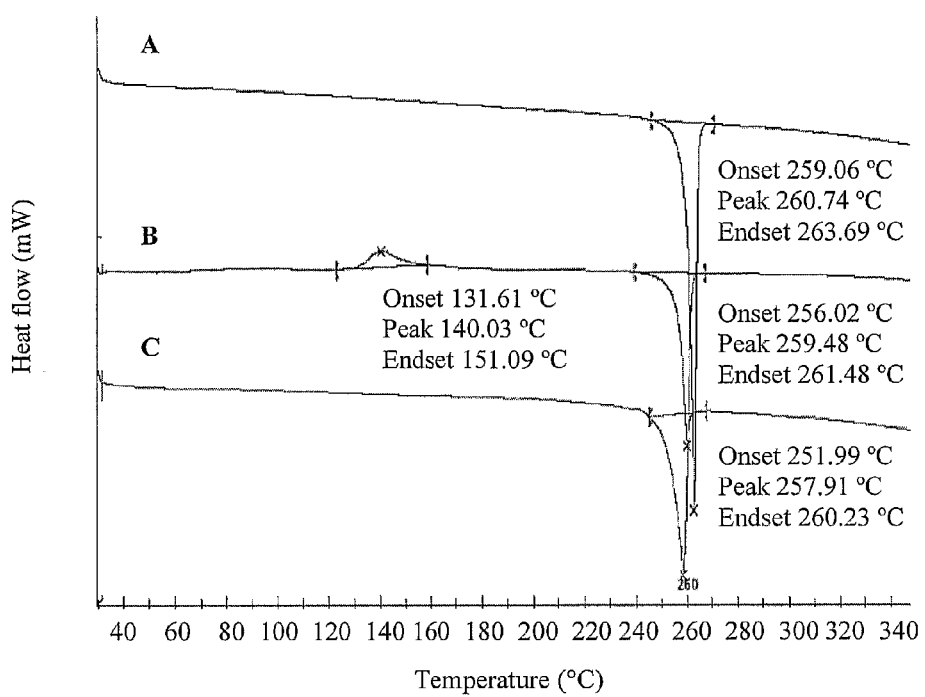
FIG. 37 illustrates a characteristic Differential Scanning calorimetry (DSC) profile of amorphous deferasirox, before (37B; weight 1.8250 mg) and after drying at 160° C. for 5 minutes (37C; weight 2.9020 mg). Also shown for comparison is the Differential Scanning calorimetry profile of deferasirox Form I (37A; weight 4.3050 mg), designated "DFX-API".

FIG. 33 illustrates a characteristic X-ray diffraction pattern of amorphous deferasirox. FIG. 34 illustrates a characteristic DSC profile of amorphous deferasirox. FIG. 35 illustrates a characteristic TGA profile of amorphous deferasirox. FIG. 36 illustrates a characteristic X-ray diffraction pattern of amorphous deferasirox, before and after drying at 160° C. for 5 minutes (also shown for comparison is the X-ray diffraction pattern of deferasirox Form I). FIG. 37 illustrates a characteristic Differential Scanning calorimetry (DSC) profile of amorphous deferasirox, before and after drying at 160° C. for 5 minutes (also shown for comparison is the DSC profile of deferasirox Form I).

CONCLUSION

Based on all the results, one amorphous, one hydrate and several solvates of deferasirox were found and characterized as set forth herein.

Those skilled in the art will recognize that various changes and/or modifications may be made to aspects or embodiments of this invention and that such changes and/or modifications may be made without departing from the spirit of this invention. Therefore, it is intended that the appended claims cover all such equivalent variations as will fall within the spirit and scope of this invention.

It is intended that each of the patents, applications, and printed publications, including books, mentioned in this patent document be hereby incorporated by reference in their entirety.

What is claimed is:

1. A process for the preparation of deferasirox, comprising the steps of:
   a) converting salicylic acid to its acyl chloride:

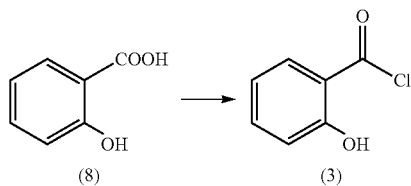 [SMILES: O=C(O)c1ccccc1O ; O=C(Cl)c1ccccc1O]

b) reacting salicyl chloride with an amidating reagent so as to produce a deferasirox intermediate of formula:

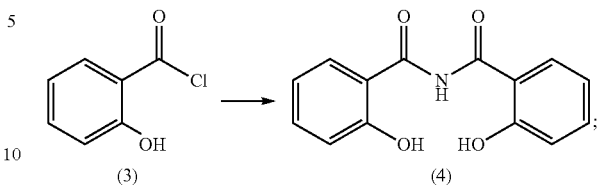

and
   c) reacting intermediate with 4-hydrazinobenzoic acid to form deferasirox:

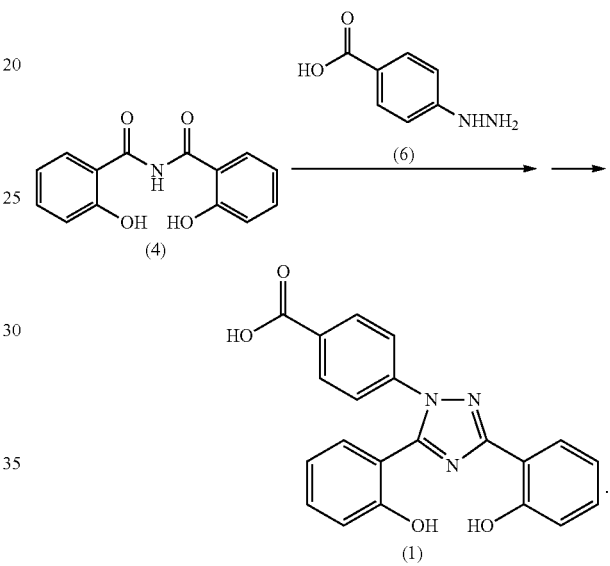

2. The process according to claim 1, wherein the amidating reagent in step (b) is selected from the group consisting of disilazanes of general formula $(R^1R^2R^3Si)_2NH$ and cyclosilazanes of general formula $(R^1R^2SiNH)_n$, wherein n is 3 or 4 and $R^1$, $R^2$ and $R^3$ are each independently alkyl or aryl.

3. The process according to claim 1, wherein in step (b) the reaction between salicyl chloride and the amidating reagent is conducted in the presence of catalyst, wherein the catalyst is selected from the group consisting of tertiary amine selected from the group consisting of triethylamine, diisopropylethylamine, N-methylmorpholine, pyridine, lutidine, DBU, DBN, DABCO and picoline.

4. The process according to claim 1, wherein step (a) and step (b) are combined as a one-pot synthesis.

5. The process according to claim 1, wherein step (c) is performed in a solvent in the presence of acid, wherein the solvent is selected from the group consisting of alcohols, ethers, DMF, NMP, DMSO, water and mixtures thereof; and wherein the acid is an inorganic acid selected from the group consisting of hydrochloric acid, hydrobromic acid, phosphoric acid and sulfuric acid; or an organic acid selected from the group consisting of formic acid, acetic acid, trifluoroacetic acid, methanesulfonic acid and propionic acid.

6. The process according to claim 1, wherein step (b) is conducted in a solvent selected from the group consisting of hydrocarbons and halogenated hydrocarbons, aromatic hydrocarbons and halogenated aromatic hydrocarbons, esters, ethers, carboxylic acid amides, acetonitrile, and mixtures of these solvents.

7. The process according to claim 6, wherein the solvent is DMF or toluene.

8. The process according to claim 2, wherein the amidating reagent is hexamethyldisilizane.

9. The process according to claim 3, wherein the catalyst in step (b) is pyridine or DMF.

10. The process according to claim 4, wherein step (a) and (b) are conducted in toluene.

* * * * *